United States Patent
Cawood et al.

(10) Patent No.: US 12,071,631 B2
(45) Date of Patent: Aug. 27, 2024

(54) ADENOVIRAL VECTORS

(71) Applicant: Oxford Genetics Limited, Oxford (GB)

(72) Inventors: Ryan Cawood, Oxford (GB); Weiheng Su, Oxford (GB)

(73) Assignee: Oxford Genetics Limited, Oxford (GB)

( * ) Notice: Subject to any disclaimer, the term of this patent is extended or adjusted under 35 U.S.C. 154(b) by 1142 days.

(21) Appl. No.: 16/634,024

(22) PCT Filed: Jul. 24, 2018

(86) PCT No.: PCT/GB2018/052083
§ 371 (c)(1),
(2) Date: Jan. 24, 2020

(87) PCT Pub. No.: WO2019/020992
PCT Pub. Date: Jan. 31, 2019

(65) Prior Publication Data
US 2020/0239909 A1    Jul. 30, 2020

(30) Foreign Application Priority Data

Jul. 25, 2017 (GB) .................................... 1711971
Apr. 19, 2018 (GB) .................................... 1806375

(51) Int. Cl.
*C12N 15/86* (2006.01)
(52) U.S. Cl.
CPC .... *C12N 15/86* (2013.01); *C12N 2710/10343* (2013.01); *C12N 2799/022* (2013.01); *C12N 2810/6018* (2013.01); *C12N 2830/005* (2013.01)

(58) Field of Classification Search
CPC .... C12N 2799/022; C12N 2710/10341; C12N 15/86
See application file for complete search history.

(56) References Cited

U.S. PATENT DOCUMENTS

| 5,658,776 A | 8/1997 | Flotte et al. |
| 5,837,484 A | 11/1998 | Trempe et al. |
| 5,856,152 A | 1/1999 | Wilson et al. |
| 6,113,913 A | 9/2000 | Brough et al. |

(Continued)

FOREIGN PATENT DOCUMENTS

| CN | 101035901 A | 9/2007 |
| CN | 102533657 A | 4/2012 |

(Continued)

OTHER PUBLICATIONS

Needham, P., et al., "Adeno-Associated Virus Rep Protein-Mediated Inhibition of Transcription of the Adenovirus Major Late Promoter In Vitro", (Jul. 2006), Journal of Virology, vol. 80, No. 13, p. 6207-6217. (Year: 2006).*

(Continued)

*Primary Examiner* — Neil P Hammell
*Assistant Examiner* — Jenna L Persons
(74) *Attorney, Agent, or Firm* — McDonnell Boehnen Hulbert & Berghoff LLP

(57) ABSTRACT

The present invention relates to an adenoviral vector comprising a regulatable Major Late Promoter and an exogenous transgene. The invention also provides cells comprising such adenoviral vectors, and processes using such vectors.

16 Claims, 24 Drawing Sheets
Specification includes a Sequence Listing.

(56) References Cited

U.S. PATENT DOCUMENTS

| | | | |
|---|---|---|---|
| 6,383,794 B1* | 5/2002 | Mountz | C12N 15/86 |
| | | | 435/235.1 |
| 10,647,999 B2 | 5/2020 | Cawood et al. | |
| 2015/0232880 A1 | 8/2015 | Hemminki et al. | |
| 2018/0127470 A1 | 5/2018 | Cawood | |
| 2020/0072820 A1 | 3/2020 | Cawood et al. | |
| 2020/0157567 A1 | 5/2020 | Cawood et al. | |
| 2020/0277629 A1 | 9/2020 | Cawood et al. | |
| 2021/0163987 A1 | 6/2021 | Cawood et al. | |
| 2022/0154174 A1 | 5/2022 | Lopez-Anton et al. | |
| 2022/0162636 A1 | 5/2022 | Cawood et al. | |
| 2023/0076955 A1* | 3/2023 | Cawood | C12N 7/00 |

FOREIGN PATENT DOCUMENTS

| | | |
|---|---|---|
| GB | 2496849 A | 5/2013 |
| WO | 1995/011984 A2 | 5/1995 |
| WO | 99/53085 A2 | 10/1999 |
| WO | 99/57296 A1 | 11/1999 |
| WO | 2000/22137 A2 | 4/2000 |
| WO | 01/36623 A2 | 5/2001 |
| WO | 2006-127956 A2 | 11/2006 |
| WO | 2016/189326 A1 | 12/2016 |
| WO | 2017/149292 A1 | 9/2017 |
| WO | 2018/167481 A1 | 9/2018 |
| WO | 2018/189535 A1 | 10/2018 |
| WO | 2019-058108 A1 | 3/2019 |
| WO | 2019-141993 A1 | 7/2019 |
| WO | 2020-161484 A1 | 8/2020 |
| WO | 2020-183133 A1 | 9/2020 |
| WO | 2021-156609 A1 | 8/2021 |
| WO | 2021-156611 A1 | 8/2021 |
| WO | 2021-234388 A1 | 11/2021 |
| WO | 2021-234389 A1 | 11/2021 |
| WO | 2022-038367 A1 | 2/2022 |
| WO | 2022-038368 A1 | 2/2022 |
| WO | 2022-038369 A1 | 2/2022 |

OTHER PUBLICATIONS

He, T., et al., "A simplified system for generating recombinant adenoviruses", (Mar. 3, 1998). PNAS, 95(5), p. 2509-2514. (Year: 1998).*

Lan, S., et al., "A suppressive effect of Sp1 recruitment to the first leader 5' splice site region on L4-22K-mediated activation of the adenovirus major late promoter", (Aug. 3, 2015), Virus Research, 210 (2015) p. 133-140. (Year: 2015).*

Ibrisimovic, M., et al., "An adenoviral vector-based expression and delivery system for the inhibition of wild-type adenovirus replication by artificial microRNAs", (Nov. 2, 2012), Antiviral Research. 97 (2013) p. 10-23. (Year: 2012).*

Young, A., et al., "Failure of Translation of Human Adenovirus mRNA in Murine Cancer Cells Can be Partially Overcome by L4-100K Expression In Vitro and In Vivo", (available online Jun. 26, 2012), Molecular Therapy, vol. 20, Iss. 9, p. 1676-1688. (Year: 2012).*

Mason, B., et al., "Adenovirus Vaccine Vectors Expressing Hepatitis B Surface Antigen: Importance of Regulatory Elements in the Adenovirus Major Late Intron", (Aug. 1990), Virology, 177(2), p. 452-461. (Year: 1990).*

Molin, M., et al., "Two Novel Adenovirus Vector Systems Permitting Regulated Protein Expression in Gene Transfer Experiments", (Oct. 1998), Journal of Virology, vol. 72, No. 10, p. 8358-8361. (Year: 1998).*

Uyehara, C. and McKay, D., "Direct and widespread role for the nuclear receptor EcR in mediating the response to ecdysone in *Drosophila*", (Apr. 24, 2019), PNAS, 116 (20), p. 9893-9902. (Year: 2019).*

Mei, Y., et al., "Comparative analysis of the genome organization of human adenovirus 11, a member of the human adenovirus species B, and the commonly used human adenovirus 5 vector, a member of species C", (Aug. 1, 2003), Journal of General Virology, vol. 84, Iss. 8, p. 2061-2071. (Year: 2003).*

Engler, J., et al., "Sequences of human adenovirus Ad3 and Ad7 DNAs encoding the promoter and first leader segment of late RNAs", (Mar. 1981), Gene, vol. 13, Iss. 2. p. 133-143. (Year: 1981).*

Young, C.S.H. "The Structure and Function of the Adenovirus Major Late Promoter", (2003), Adenoviruses: Model and Vectors in Virus-Host Interactions, p. 213-249. (Year: 2003).*

Brunet, L., et al., "Mutations in the Adenovirus Major Late Promoter: Effects on Viability and Transcription during Infection", (Mar. 1998). Molecular and Cellular Biology, vol. 7, No. 3, p. 1091-1100. (Year: 1998).*

Wang, J., et al., "Plasmids for the in vitro analysis of RNA polymerase II-dependent transcription based on a G-free template", (Apr. 29, 1998), Biochimica et Biophysica Acta, 1397 (1998), p. 141-145. (Year: 1998).*

Biasiotto, R. and Akusjarvi, G. "Regulation of Human Adenovirus Alternative RNA Splicing by the Adenoviral L4-33K and L4-22K Proteins", (Jan. 28, 2015), International Journal of Molecular Sciences, 16 p. 2893-2912. (Year: 2015).*

Ghochikyan, A., et al., "Arginine Operator Binding by Heterologous and Chimeric ArgR Repressors from *Escherichia coli* and Bacillus stearothermophilus", (Dec. 2002), Journal of Bacteriology, vol. 184, No. 23, p. 6602-6614. (Year: 2002).*

Blackstrom, E., et al., "Adenovirus L4-22K stimulates major late transcription by a mechanism requiring the intragenic late-specific transcription factor-binding site", (Jun. 4, 2010), Virus Research, 151 (2010), p. 220-228. (Year: 2010).*

Invitrogen by Life Technologies, "pcDNA4/TO Expression vector designed for use with the T-REx system", (Dec. 16, 2011), Cat. V1020-20, p. i-21. (Year: 2011).*

Patzer, E., et al., "Intracellular Assembly and Packaging of Hepatitis B Surface Antigen Particles Occur in the Endoplasmic Reticulum", (Jun. 1986), 58(3) p. 884-892. (Year: 1986).*

Biasiotto et al., "Regulation of Human Adenovirus Alternative RNA Splicing by the Adenovirus L4-33K and L4-22K Proteins", Int. J. Mol. Sci., 2015, vol. 16, pp. 2893-2912.

Green, M., et al., "The Transcription-Repression Domain of the Adenovirus E1A Oncoprotein Targets p300 at the Promoter", Oncogene, 2008, vol. 27, pp. 4446-4455.

Li, L., et al., "c-Myc Represses Transcription In Vivo by a Novel Mechanism Dependent on the Initiator Element and Myc Box II", The EMBO Journal, 1994, vol. 13(17), pp. 4070-4079.

Massie, B., et al., "Inducible Overexpression of a Toxic Protein by an Adenovirus Vector with a Tetracycline-Regulatable Expression Cassette", Journal of Virology, Mar. 1998, vol. 72(3), pp. 2289-2296.

McVoy, M.A., et al., "Tetracycline-Mediated Regulation of Gene Expression within the Human Cytomegalovirus Genome", Virology, 1999, vol. 258, pp. 295-303.

International Search Report and Written Opinion, from the International Searching Authority, for International Patent Application PCT/GB2018/052083, mailed Sep. 19, 2018, pp. 1-33.

UK Search Report, from the UK Intellectual Property Office, for International Patent Applicaiton GB1711971.0, dated Apr. 30, 2018, pp. 1-3.

Examination Report, pp. 1-4 and dated Jan. 5, 2021, for Canada Application No. 3070654.

Yongjing et al., "A Novel Triple-Regulated Oncolytic Adenovirus Carrying Human Tumor Necrosis Factor-Related Apoptosis-Inducing Ligand Gene Exerts Potent Antitumor Efficacy on Lung Cancer in Vitro", Chin. J. Exp. Surg., 2009, vol. 26, No. 3, pp. 327-330 (English Abstract Included).

Examination Report, pp. 1-5 and dated Jul. 29, 2020, for Canada Application No. 3070654.

Green, N.K., et al., "Extended Plasma Circulation Time and Decreased Toxicity of Polymer-Coated Adenovirus", Gene Therapy, Jun. 24, 2004, vol. 11(16), pp. 1256-1263.

Kärber, G., "50% End-Point Calculation", Arch. Exp. Pathol. Pharmak., 1931, vol. 162, pp. 480-483.

(56) References Cited

OTHER PUBLICATIONS

Mittereder, N., et al., "Evaluation of the Concentration and Bioactivity of Adenovirus Vectors for Gene Therapy", Journal of Virology, Nov. 1996, vol. 70(11), pp. 7498-7509.
Tollefson, A.E., et al., "The E3-11.6-kDa Adenovirus Death Protein (ADP) is Required for Efficient Cell Death: Characterization of Cells Infected with adp Mutants", Virology, Apr. 8, 1996, vol. 220(1), Article No. 0295, pp. 152-162.
Young, C.S.H., et al., "The Structure and Function of the Adenovirus Major Late Promoter", Curr. Top Microbiol. Immunol., 2003, vol. 272, pp. 213-249.
Examination Report, pp. 1-5 and dated Jul. 9, 2020, for Canada Application No. 3070654.
Office Action dated Nov. 21, 2022 issued in Indian Patent Application No. 201947052883.
Babiss, L.E., et al., "Adenovirus Type 5 Early Region 1b Gene Product is Required for Efficient Shutoff of Host Protein Synthesis", J. Virol., Apr. 1984, vol. 50(1), pp. 202-212.
Beaton, A., et al., "Expression from the Adeno-Associated Virus p5 and p19 Promoters is Negatively Regulated in Trans by the Rep Protein", J. Virol., Oct. 1989, vol. 63(10), pp. 4450-4454.
Concino, M., et al., "Point Mutations of the Adenovirus Major Late Promoter with Different Transcriptional Efficiencies In Vitro", J. Biol. Chem., Jul. 10, 1983, vol. 258(13), pp. 8493-8496.
Concino, M.F., et al., "The Adenovirus Major Late Promoter TATA Box and Initiation Site are both Necessary for Transcription In Vitro", Nucleic Acids Res., Oct. 11, 1984, vol. 12(19), pp. 7423-7433.
Cuesta, R., et al, "Structural Basis for Competitive Inhibition of eIF4G-Mnk1 Interaction by the Adenovirus 100-Kilodalton Protein", J. Virol., Jul. 2004, vol. 78(14), pp. 7707-7716.
El-Mogy, M., et al., "Transgene Expression Under the Adenoviral Major Late Promoter, Tripartite Leader Sequence and E1 Genes in Absence and Presence of Adenovirus Infection", Journal of Molecular Biology Research, 2012, vol. 2(1), pp. 12-23.
Garnier, A., et al., "Scale-up of the Adenovirus Expression System for the Production of Recombinant Protein in Human 293S Cells", Cytotechnology, 1994, vol. 15, pp. 145-155.
Honda, T.H., et al., "The Coxsackievirus-Adenovirus Receptor Protein as a Cell Adhesion Molecule in the Developing Mouse Brain", Molecular Brain Research, 2000, vol. 77(1), pp. 19-28.
Kelkar, S.A., et al., "Cytoplasmic Dynein Mediates Adenovirus Binding to Microtubules", Journal of Virology, Sep. 2004, vol. 78(18), pp. 10122-10132.
Li, J., et al., "Role for Highly Regulated rep Gene Expression in Adeno-Associated Virus Vector Production", J. Virol., Jul. 1997, vol. 71(7), pp. 5236-5243.
McConnell, M.J., et al., "Biology of Adenovirus and its Use as a Vector for Gene Therapy", Human Gene Therapy, Nov. 2004, vol. 15(11), pp. 1022-1033.
Molin, M., et al., "Two Novel Adenovirus Vector Systems Permitting Regulated Protein Expression in Gene Transfer Experiments", J. Virol., Oct. 1998, vol. 72(10), pp. 8358-8361.
Ogasawara, Y., et al., "Highly Regulated Expression of Adeno-Associated Virus Large Rep Proteins in Stable 293 Cell Lines Using the Cre/Loxp Switching System", J. Gen. Virol., 1999, vol. 80, pp. 2477-2480.
Rowe, W.P., et al., "Isolation of a Cytopathogenic Agent from Human Adenoids Undergoing Spontaneous Degeneration in Tissue Culture", Proceedings of the Society for Experimental Biology and Medicine, 1953, vol. 84(3), pp. 570-573.
Tomko, R.P., et al, "HCAR and MCAR: The Human and Mouse Cellular Receptors for Subgroup C Adenoviruses and Group B Coxsackieviruses", Proc. Nat. Acad. Sci., Apr. 1997, vol. 94(7), pp. 3352-3356.
Trotman, L.C., et al., "Import of Adenovirus DNA Involves the Nuclear Pore Complex Receptor CAN/Nup214 and Histone H1", Nature Cell Biology, 2001, vol. 3(12), pp. 1092-1100.
Wickham, T.J., et al., "Integrin-Alpha-V-Beta-3 and Integrin-Alpha-V-Beta-5 Promote Adenovirus Internalization but not Virus Attachment", Cell, Apr. 23, 1993, vol. 73(2), pp. 309-319.
Xi, Q., et al, "Tethering of eIF4G to Adenoviral mRNAs by Viral 100k Protein Drives Ribosome Shunting", Genes Dev., 2004, vol. 18(16), pp. 1997-2009.
Yang, Q., et al., "Characterization of Cell Lines that Inducibly Express the Adeno-Associated Virus Rep Proteins", J. Virol., Aug. 1994, vol. 68(8), pp. 4847-4856.
Zhang, H-G., et al., "Recombinant Adenovirus Expressing Adeno-Associated Virus Cap and Rep Proteins Supports Production of High-Titer Recombinant Adeno-Associated Virus", Gene. Ther., 2001, vol. 8(9), pp. 704-712.

\* cited by examiner

SEQUENCE LISTING

```
<160> NUMBER OF SEQ ID NOS: 18

<210> SEQ ID NO 1
<211> LENGTH: 107
<212> TYPE: DNA
<213> ORGANISM: Human adenovirus type 5

<400> SEQUENCE: 1
cgccctcttc ggcatcaagg aaggtgattg gtttgtaggt gtaggccacg tgaccgggtg    60
ttcctgaagg ggggctataa aaggggtgg gggcgcgttc gtcctca                  107

<210> SEQ ID NO 2
<211> LENGTH: 19
<212> TYPE: DNA
<213> ORGANISM: Artificial Sequence
<220> FEATURE:
<223> OTHER INFORMATION: TetR binding site

<400> SEQUENCE: 2
tccctatcag tgatagaga                                                 19

<210> SEQ ID NO 3
<211> LENGTH: 624
<212> TYPE: DNA
<213> ORGANISM: Artificial Sequence
<220> FEATURE:
<223> OTHER INFORMATION: TetR

<400> SEQUENCE: 3
atgtcgcgcc tggacaaaag caaagtgatt aactcagcgc tggaactgtt gaatgaggtg    60
ggaattgaag gactcactac tcgcaagctg gcacagaagc tgggcgtcga gcagccaacg   120
ctgtactggc atgtgaagaa taaacgggcg ctcctagacg cgcttgccat cgaaatgctg   180
gaccgccatc acacccactt ttgcccctg gagggcgaat cctggcaaga ttttctgcgg   240
aacaatgcaa agtcgttccg gtgcgctctg ctgtcccacc gcgatggcgc aaaagtgcac   300
ctgggcactc ggcccaccga gaacaatac gaaaccctgg aaaaccaact ggctttcctt   360
tgccaacagg gattttcact ggagaatgcc ctgtacgcac tatccgcggt cggccacttt   420
accctgggat gcgtcctcga agatcaggag caccaagtcg ccaaggagga aagagaaact   480
cctaccactg actcaatgcc tccgctcctg agacaagcca tcgagctgtt cgaccaccag   540
ggtgctgaac ctgcatttct gttcgggctt gaactgatta tctgcggcct ggagaaacag   600
ttgaagtgcg agtcgggatc ctag                                         624

<210> SEQ ID NO 4
<211> LENGTH: 207
<212> TYPE: PRT
```

<213> ORGANISM: Artificial Sequence
<220> FEATURE:
<223> OTHER INFORMATION: TetR

<400> SEQUENCE: 4

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 5
<211> LENGTH: 8
<212> TYPE: PRT
<213> ORGANISM: Artificial Sequence
<220> FEATURE:
<223> OTHER INFORMATION: Opposite TetR binding site

<400> SEQUENCE: 5

Glu Ser Leu Ser Leu Ile Gly Thr
1               5

<210> SEQ ID NO 6
<211> LENGTH: 107
<212> TYPE: DNA
<213> ORGANISM: Artificial Sequence
<220> FEATURE:
<223> OTHER INFORMATION: Modified MLP

<400> SEQUENCE: 6
cgccctcttc ggcatcaagg aaggtgattg gtttgtaggt gtaggccacg tgaccgggtg    60
ttcctgaagg ggggctataa aaggtcccta tcagtgatag agactca                 107

<210> SEQ ID NO 7
<211> LENGTH: 107
<212> TYPE: DNA
<213> ORGANISM: Artificial Sequence
<220> FEATURE:
<223> OTHER INFORMATION: Modified MLP

<400> SEQUENCE: 7
cgccctcttc ggcatcaagg aaggtgattg gtttgtaggt gtaggccacg tgactcccta    60
tcagtgatag agaactataa aaggtcccta tcagtgatag agactca    107

<210> SEQ ID NO 8
<211> LENGTH: 416
<212> TYPE: DNA
<213> ORGANISM: Artificial Sequence
<220> FEATURE:
<223> OTHER INFORMATION: Sequence in viral vector or other sequence

<400> SEQUENCE: 8
aggccagcac gaaggaggct aagtgggagg ggtagcggtc gttgtccact aggggggtcca    60 ctcgctccag ggtgtgaaga cacatgtcgc cctcttcggc atcaaggaag gtgattggtt    120
tgtaggtgta ggccacgtga ccgggtgttc ctgaagggg gctataaaag gtccctatca    180
gtgatagaga ctcactctct tccgcatcgc tgtctgcgag ggccagctgt tggggtgagt    240
actccctctg aaaagcgggc atgacttctg cgctaagatt gtcagtttcc aaaaacgagg    300
aggatttgat attcacctgg cccgcggtga tgcctttgag ggtggccgca tccatctggt    360
cagaaaagac aatcttttg ttgtcaagct tggtggcaaa cgacccgtag agggcg    416

<210> SEQ ID NO 9
<211> LENGTH: 21
<212> TYPE: DNA
<213> ORGANISM: Artificial Sequence
<220> FEATURE:
<223> OTHER INFORMATION: Ad5 fiber forward primer

<400> SEQUENCE: 9
tggctgttaa aggcagtttg g    21

<210> SEQ ID NO 10
<211> LENGTH: 23
<212> TYPE: DNA
<213> ORGANISM: Artificial Sequence
<220> FEATURE:
<223> OTHER INFORMATION: Ad5 fiber reverse primer

<400> SEQUENCE: 10
gcactccatt ttcgtcaaat ctt    23

<210> SEQ ID NO 11
<211> LENGTH: 33
<212> TYPE: DNA
<213> ORGANISM: Artificial Sequence
<220> FEATURE:
<223> OTHER INFORMATION: TaqMan probe

<400> SEQUENCE: 11
tccaatatct ggaacagttc aaagtgctca tct    33

<210> SEQ ID NO 12
<211> LENGTH: 173
<212> TYPE: PRT
<213> ORGANISM: Human adenovirus type 5

<400> SEQUENCE: 12

Ile Ala Lys Leu Leu Ser Asn Ala Leu Tyr Gly Ser Phe Ala Thr Lys
1               5                   10                  15

Leu Asp Asn Lys Lys Ile Val Phe Ser Asp Gln Met Asp Ala Ala Thr 20                  25                  30
Leu Lys Gly Ile Thr Ala Gly Gln Val Asn Ile Lys Ser Ser Ser Phe
             35                  40                  45

Leu Glu Thr Asp Asn Leu Ser Ala Glu Val Met Pro Ala Phe Gln Arg
 50                  55                  60

Glu Tyr Ser Pro Gln Gln Leu Ala Leu Ala Asp Ser Asp Ala Glu Glu
 65                  70                  75                  80

Ser Glu Asp Glu Arg Ala Pro Thr Pro Phe Tyr Ser Pro Pro Ser Gly
                 85                  90                  95

Thr Pro Gly His Val Ala Tyr Thr Tyr Lys Pro Ile Thr Phe Leu Asp
                 100                 105                 110

Ala Glu Glu Gly Asp Met Cys Leu His Thr Leu Glu Arg Val Asp Pro
             115                 120                 125

Leu Val Asp Asn Asp Arg Tyr Pro Ser His Leu Ala Ser Phe Val Leu
         130                 135                 140

Ala Trp Thr Arg Ala Phe Val Ser Glu Trp Ser Glu Phe Leu Tyr Glu
145                 150                 155                 160

Glu Asp Arg Gly Thr Pro Leu Glu Asp Arg Pro Leu Lys
                 165                 170

<210> SEQ ID NO 13
<211> LENGTH: 390
<212> TYPE: DNA
<213> ORGANISM: Human adenovirus type 5

<400> SEQUENCE: 13 cactagggggg tccactcgct ccagggtgtg aagacacatg tcgccctctt cggcatcaag      60
gaaggtgatt ggtttgtagg tgtaggccac gtgaccgggt gttcctgaag ggggctata       120
aaaggggggtg ggggcgcgtt cgtcctcact ctcttccgca tcgctgtctg cgagggccag     180
ctgttggggt gagtactccc tctgaaaagc gggcatgact tctgcgctaa gattgtcagt     240
ttccaaaaac gaggaggatt tgatattcac ctggcccgcg gtgatgcctt tgagggtggc     300
cgcatccatc tggtcagaaa agacaatctt tttgttgtca agcttggtgg caaacgaccc    360
gtagagggcg ttggacagca acttggcgat                                       390

<210> SEQ ID NO 14
<211> LENGTH: 390
<212> TYPE: DNA
<213> ORGANISM: Human adenovirus type 5

<400> SEQUENCE: 14
atcgccaagt tgctgtccaa cgccctctac gggtcgtttg ccaccaagct tgacaacaaa      60
aagattgtct ttctgaccag atggatgcgg ccacccctca aggcatcac cgcgggccag       120
gtgaatatca atcctcctcg ttttttggaa actgacaatc ttagcgcaga agtcatgccc     180
gcttttcaga gggagtactc accccaacag ctggccctcg cagacagcga tgcggaagag     240
agtgaggacg aacgcgcccc caccccctt tatagcccc cttcaggaac acccggtcac      300
gtggcctaca cctacaaacc aatcaccttc cttgatgccg aagagggcga catgtgtctt     360
cacacccttgg agcgagtgga ccccctagtg                                     390

<210> SEQ ID NO 15
<211> LENGTH: 160
<212> TYPE: PRT
<213> ORGANISM: Artificial Sequence
<220> FEATURE:

<223> OTHER INFORMATION: Modified MLP

<400> SEQUENCE: 15

```
Ala Lys Glu Arg Ala Asp Arg Asp Lys Asn Gln Thr Leu Arg Ser Ile
1               5                   10                  15

Ala Lys Leu Leu Ser Asn Ala Leu Tyr Gly Ser Phe Ala Thr Lys Leu
            20                  25                  30

Asp Asn Lys Lys Ile Val Phe Ser Asp Gln Met Asp Ala Ala Thr Leu
        35                  40                  45

Lys Gly Ile Thr Ala Gly Gln Val Asn Ile Lys Ser Ser Ser Phe Leu
    50                  55                  60

Glu Thr Asp Asn Leu Ser Ala Glu Val Met Pro Ala Phe Gln Arg Glu
65                  70                  75                  80

Tyr Ser Pro Gln Gln Leu Ala Leu Ala Asp Ser Asp Ala Glu Glu Ser
                85                  90                  95

Glu Ser Leu Ser Leu Ile Gly Thr Phe Tyr Ser Pro Pro Ser Gly Thr
            100                 105                 110

Pro Gly His Val Ala Tyr Thr Tyr Lys Pro Ile Thr Phe Leu Asp Ala
        115                 120                 125

Glu Glu Gly Asp Met Cys Leu His Thr Leu Glu Arg Val Asp Pro Leu
    130                 135                 140

Val Asp Asn Asp Arg Tyr Pro Ser His Leu Ala Ser Phe Val Leu Ala
145                 150                 155                 160
```

<210> SEQ ID NO 16
<211> LENGTH: 480
<212> TYPE: DNA
<213> ORGANISM: Artificial Sequence
<220> FEATURE:
<223> OTHER INFORMATION: Modified MLP

<400> SEQUENCE: 16

```
aggccagcac gaaggaggct aagtgggagg ggtagcggtc gttgtccact aggggggtcca    60
ctcgctccag ggtgtgaaga cacatgtcgc cctcttcggc atcaaggaag gtgattggtt   120
tgtaggtgta ggccacgtga ccgggtgttc ctgaaggggg gctataaaag gtccctatca   180
gtgatagaga ctcactctct tccgcatcgc tgtctgcgag ggccagctgt tggggtgagt   240
actccctctg aaaagcgggc atgacttctg cgctaagatt gtcagtttcc aaaaacgagg   300
aggatttgat attcacctgg cccgcggtga tgcctttgag ggtggccgca tccatctggt   360
cagaaaagac aatcttttg ttgtcaagct tggtggcaaa cgacccgtag agggcgttgg   420
acagcaactt ggcgatggag cgcagggttt ggttttttgtc gcgatcggcg cgctccttgg   480
```

<210> SEQ ID NO 17
<211> LENGTH: 480
<212> TYPE: DNA
<213> ORGANISM: Artificial Sequence
<220> FEATURE:
<223> OTHER INFORMATION: Modified MLP

<400> SEQUENCE: 17

```
ccaaggagcg cgccgatcgc gacaaaaacc aaaccctgcg ctccatcgcc aagttgctgt    60
ccaacgccct ctacgggtcg tttgccacca agcttgacaa caaaaagatt gtcttttctg   120
accagatgga tgcggccacc ctcaaaggca tcaccgcggg ccaggtgaat atcaaatcct   180
cctcgttttt ggaaactgac aatcttagcg cagaagtcat gcccgctttt cagagggagt   240
actcacccca acagctggcc ctcgcagaca gcgatgcgga agagagtgag tctctatcac   300
```

```
tgatagggac cttttatagc cccccttcag gaacacccgg tcacgtggcc tacacctaca      360
aaccaatcac cttccttgat gccgaagagg gcgacatgtg tcttcacacc ctggagcgag      420
tggaccccct agtggacaac gaccgctacc cctcccactt agcctccttc gtgctggcct      480
```

<210> SEQ ID NO 18
<211> LENGTH: 8
<212> TYPE: PRT
<213> ORGANISM: Artificial Sequence
<220> FEATURE:
<223> OTHER INFORMATION: DNA polymerase coding sequence between MLP TATA
      box and +1

<400> SEQUENCE: 18

Glu Asn Glu Arg Ala Pro Thr Pro
1               5

ADENOVIRAL VECTORS

CROSS-REFERENCE

This application is a 371 U.S. national phase of international application no. PCT/GB2018/052083, filed Jul. 24, 2018, which claims priority from GB patent application no. 1711971.0 filed Jul. 25, 2017 and GB patent application no. 1806375.0, filed Apr. 19, 2018, which applications are incorporated by reference in its entirety.

FIELD OF INVENTION

The present invention relates to an adenoviral vector comprising a regulatable Major Late Promoter and an exogenous transgene. The invention also provides cells comprising such adenoviral vectors, and processes using such vectors.

Adenoviruses are an attractive and versatile tool in biotechnology, having well understood genetics and the ability to grow to high yields in tissue culture. The replication cycle of Adenoviruses is highly complex, involving both early and late phases. The transition from early to late is considered to occur following DNA replication and the activation of the Major Late promoter (MLP) in the virus genome. The MLP drives the expression of all virus late transcripts, and can convert up to 30% of the cells' protein into virus structural proteins. Modification to the MLP in situ to provide inducible expression has not previously been demonstrated, primarily because the virus DNA polymerase coding sequence is in the opposing DNA strand.

Whilst adenoviruses are useful laboratory tools for a number of applications, the fact they are so productive represents a major problem if they are used in a manufacturing work flow, namely they generate substantial amounts of virus particles that must be removed during downstream processing. For example, when adenovirus has previously been used for protein expression purposes, or the production of other virus-like particles, or the large scale manufacture of Adeno-associated virus (AAV), the presence of intact Adenoviral particles at the end of the production process is highly undesirable.

The ability to manufacture proteins in mammalian cells is increasingly attractive, with many high value recombinant proteins now being produced in these systems, affording optimum protein processing, folding and glycosylation. This is frequently achieved using transient transfection of a plasmid encoding the required transgene under the control of a strong promoter, such as the Cytomegalovirus (CMV) immediate early promoter. However, compared to some viral systems in other organisms (such as Baculovirus in insect cells), this process is relatively inefficient, often demonstrating variable protein yields that rarely exceed 3% of the total cell protein mass.

The extensive characterisation of the Adenovirus genome, coupled with the wealth of knowledge regarding its gene expression and life cycle, makes this virus an ideal candidate platform on which to significantly improve recombinant protein yields. One major benefit is demonstrated by the virus' ability to actively hijack the mammalian cell's machinery, and to inhibit the production of cellular proteins.

However, in addition to inhibiting the production of cellular proteins, considerable cellular resources are used by the virus to produce viral structural proteins. The quantity of capsid proteins produced, for example, is vast and has been calculated to be up to 30% of total cell protein, and removing these proteins and the assembled virus particles after production is challenging.

Similar to recombinant proteins, the demand for adeno-associated virus particles is increasing significantly, owing to recent clinal successes in the treatment of retinal disorders and haemophilia. Traditionally, the production of AAV has been achieved through two different routes. Initially, AAV was generated using wild-type (WT) Adenovirus serotype 5 whilst transfecting cells with plasmids encoding the Rep and Cap genes and the AAV genome. This allowed the WT adenovirus to provide a number of factors in trans that facilitated virus replication. However, there a number of limitations to this approach: for example, each batch of AAV must be separated from the Ad5 particles to provide a pure product and ensuring that all Ad5 has been removed is challenging. Moreover, the fact that during production the cell is devoting huge resource to the production of Adenoviral particles rather than AAV is also undesirable.

More recently, the adenovirus-based systems have been replaced with plasmids encoding the sections of the Adenovirus genome required for AAV production. Whilst this has solved some of the concerns over Adenovirus particles being present in the final virus preparation, a number of issues remain. These include the requirement to pre-manufacture sufficient plasmid for transfection into the production cell line and the inherently inefficient process of transfection itself. The yields from these systems are also lower than those using Ad5 based approaches.

SUMMARY OF INVENTION

The inventors have now discovered that transcription of the late adenoviral genes can be regulated (e.g. inhibited) by the insertion of a repressor element into the Major Late Promoter. By "switching off" expression of the Late genes, the cell's protein-manufacturing capabilities can be diverted toward the production of a desired recombinant protein. Importantly, the strategic silencing of the Major Late promoter in the adenovirus genome in accordance with the current invention allows the virus to still replicate its DNA in the cell, providing thousands of DNA copies of the virus genome that can be transcribed for a range of applications.

This invention provides a range of advantages. For example, it can be used to direct a cell's protein production capability towards the production of specific recombinant proteins at increased yields compared to comparable systems wherein the viral Late genes are still expressed. Furthermore, the ability to "switch off" the production of viral structural proteins means that no or essentially no viral particles are produced during the protein-production process. Consequently, economic savings can be made due to a reduction in the need to remove virus particles from the purified protein.

The invention also has the advantage of providing a simple, cost-effective, way to manufacture AAV particles where the Rep and Cap proteins of AAV can be encoded within the Adenovirus to provide the high expression levels which are required to make the AAV particles by maintaining the replication of the Adenoviral genome, but also preventing the production Adenovirus particles in the final AAV preparation.

Some modifications of the MPL have previously been reported. These include making a copy of the MLP and placing it either in other plasmids for expression level analysis (El -Mogy, 2012) or within the E1 region of the Adenovirus genome subject to the insertion of sites to regulate its expression (Molin, 1998). Other work has included the mutation of the MLP TATA box for both basic research (Concino et al., 1983; Concino et al., 1984) and in order to allow the virus to be selectively grown only in cells which have a trans-complementing factor in a cell. Importantly, the latter approach provides for a system where the activity of the major late promoter is entirely dependent on a complementing protein factor being present in a cell, and therefore in a cell where this factor is absent the MLP is not active. The invention, however, provides the converse of this, where the MLP maintains it full expression activity level in cells where a repressor not bound, providing high level virus replication with minimal disturbance to the virus life cycle.

The virus of the invention described herein is therefore fully active when not repressed but is capable of being repressed, depending on the presence or absence of a repressor. A repressor binding site has not previously successfully been inserted into the MLP in situ for the regulation of its expression in an adenovirus genome. The current inventors have further improved this system to place the repressor protein coding sequence under the control of the Major Late Promoter itself. In this approach, the Major Late Promoter self-represses itself because when the Major Late Promoter tries to transcribe the structural proteins of the virus, it will also transcribe a repressor capable of repressing its own activity, thereby allowing for a negative feedback loop that prevents MLP activity and providing tight regulation of MLP expression.

It is therefore an object of the invention to provide an adenoviral vector system which provides increased yields of recombinant proteins, and can be used to provide non-adenovirus virus and virus-like particles.

It is also an object of the invention to provide a process of producing a transgene product in adenovirus-infected cells, which reduces the need to remove virus particles from the purified product which may be a protein, non-adenovirus particle or virus-like particle.

DESCRIPTION OF THE DRAWINGS

FIG. 10A) HEK293 cells were transduced with E1/E3 Ad5 or Ad5 TET1b MLP expressing EGFP under control of the CMV promoter at MOI 0.1 and in the presence doxycycline 0.2 µg/mL or DMSO. Image of day-6 post infection by fluorescence microscopy. HEK293 cells were also harvested for flow-cytometry analysis to determine the percentage of EGFP positive cell within the gated population (FIG. 10B). Data as mean ±SD of triple biological repetition.

FIG. 11A) Plasmid expression of EGFP encoding Ad5 TPL from the CMV promoter. HEK293 cells transfected with plasmid DNA expressing EGFP from a promoterless plasmid or under control of the CMV promoter with and without the Ad5 TPL. EGFP expression determined by flow cytometry 48 h post-transfection. FIG. 11B) MLP TET01b modified Ad5 expressing EGFP (with and without Ad5 TPL) under control of the CMV promoter in T-Rex Flp cells treated with DMSO or doxycycline 0.2 µg/mL. Cells analysis by flow cytometry 24 h, 48 h and 72 h post-infection. FIG. 11C) EGFP expression under control of the CMV promoter from plasmid DNA or MLP modified Ad5 in HEK293. HEK293 cells were transfected with plasmid expressing TETR prior to transduction with the CMV promoter plasmid expressing EGFP or MLP modified Ad5 expressing EGFP (with and without the Ad5 TPL) under control of the CMV promoter, in the presence of doxycycline or DMSO. Cells were harvested for flow cytometry 48 h post-transduction. FIG. 11D) Fluorescent microscopy image of pTETR transfected HEK293 cells transduced with MLP modified Ad5 expressing EGFP encoding Ad5 TPL, in the presence of DMSO or doxycycline 0.2 µg/mL. Image 48 h post-infection. MFI (median fluorescent intensity). Data as mean±SD.

FIG. 12A) TERA or E1/E3 Ad5 was used to transduce HEK293 at MOI 100 or 1000. Virus were harvested from cell lysate (left blot) or growth medium (right blot). FIG. 12B) Western blot analysis of growth media from HEK293 cells cultured in a dose escalation of doxycycline and transduced with TERA or E1/E3 deleted Ad5 at MOI 10 or MOI 100 (FIG. 12C). All virus samples harvested at 72 h post-infection and detected using anti-Ad5 antibodies with automated Western machine (Wes Simple Western).

FIG. 13A) HEK293 cells were infected with TERA or E1/E3 Ad5, encoding the CMV EGFP expression cassette, at MOI 1, 10 or 100, and total DNA was harvested at the indicated timepoint post-infection for qPCR analysis. FIG. 13B) TERA or E1/E3 Ad5, encoding the CMV EGFP expression cassette, was used to infect HEK293 at MOI 10 or 100, in the presence of doxycycline 0.5 µg/mL or DMSO. Total DNA was harvested at the indicated timepoint post-infection for qPCR analysis.

FIG. 14A) HEK293 cells were transduced with TERA (MOI 10) expressing EGFP from the CMV promoter (with and without Ad5 TPL), and E1/E3 Ad5 (MOI 10) or plasmid DNA (0.75 µg per ~7.0x 10$^4$ cell using Branch PEI) expressing the EGFP also under control of the CMV promoter. HEK293 cells were harvested at 24 h and 48 h post transduction for flow cytometry analysis. FIG. 14B) HEK293 cells, in the presence of DMSO or doxycycline 0.5 μg/mL, infected at MOI 100 with TERA expressing EGFP under the CMV promoter. Virus harvested from cell lysate 72 h post transduction and detected using anti-Ad5 and Anti-EGFP antibody by automated Western blot machine (Wes Simple Protein).

FIG. 15A) HEK293 cells were transduced with E1/E3 Ad5 or TERA expressing EGFP under control of the CMV (with and without the Ad5 TPL) at an MOI 10. Culture media harvested at 48 h post-transduction and (5 μL) probed with anti-6x His antibodies for BiTE® protein expression using automated Western (Wes Simple Protein). FIG. 15B) Chemiluminescence signals from each sample were further quantified and plotted to give relative expression intensity based on the detected peak and area under curve. FIG. 15C) Total DNA were harvested timepoint 0 h, 24 h, 48 h, 72 h from the virus infected HEK293 cells and genome quantified by qPCR. FIG. 15D) Detection of adenovirus protein from HEK293 cells transduced with E1/E3 Ad5 or TERA engineered to express BiTE® Protein. Culture media harvested at 48 h post-transduction and (5 μL) probed with anti-Ad5 antibodies for Ad5 major structural proteins using automated Western (Wes Simple Protein). FIG. 15E) HEK293 cells were transduced with plasmid DNA (0.75 μg per ~7.0x 10$^4$ cell using Branch PEI) or TERA expressing BiTE® protein encoding Ad5 TPL and under control of the CMV promoter at MOI 10. Growth media from transduced cells were harvested at the specified timepoint 24 h, 48 h, and 72 h post-transduction and (5 μL) probed for BiTE® protein expression using anti-6x His antibody.

FIG. 16A) HEK293 cells, in the presence of DMSO or doxycycline 0.5 μg/mL, were transfected with plasmid expressing AAV Rep and Cap genes prior to transduction with MOI 100 or 500 of E1/E3 Ad5 or TERA encoding the rAAV genome, a CMV-EGFP expression cassette flanked by AAV ITRs, or Helper-free production via triple plasmids transfection. Total recombinant viruses, from cell lysate and growth media, were extracted 72 h post-transduction and DNase I resistant genomes were quantified by qPCR primer and probe sets directed against the Fiber sequence of the adenovirus genome or the CMV promoter sequence, shared by both rAAV and adenovirus. Total genome encapsulated adenovirus per well is plotted alongside total genome encapsulated rAAV per well determined by subtraction of genome encapsulated adenovirus from each sample. FIG. 16B) Culture media (5 μL) from each specified rAAV production method were probed for adenovirus capsid proteins with anti-Ad5 antibodies using automated Western blot machine (Wes Simple Protein). FIG. 16C) rAAV capsids or viral particles (VP) produced by Helper-free transfection method or TERA-AAV transduction at MOI 500, in the presence of DMSO, were determined by ELISA. Data presented as viral particles produced per cell at point of transduction and plotted alongside total encapsulated rAAV genomes determined by qPCR analysis. FIG. 16D) Significant levels of recombinant viruses from all samples were detected by qPCR assay using primer and probe sets directed against the encoded CMV promoter, present in both adenoviruses and rAAVs. FIG. 16E) shows total rAAV2 capsids and DNase-I resistant genome encapsulated particles determined by ELISA directed toward formed-AAV2 viral capsids and quantification of rAAV genome by qPCR, respectively. FIG. 16F) Percentage of genome encapsulated rAAV determined from rAAV capsids are shown. FIG. 16G) Infectious culture media harvested from rAAV production using TERA-AAV transduction of HEK293 cells at MOI 500, in the presence of DMSO or doxycycline 0.5 μg/mL, was used for infection of fresh HEK293, in the presence of doxycycline 0.5 μg/mL, at 1:100 dilution. Cell monolayer imaged by fluorescence microscopy 24 h and 96 h post infection. FIG. 16H) Contaminating infectious adenoviruses were determined from rAA samples produced by method of Helper-free transfection, or E1/E3 Ad5 or TERA transduction at MOI 100 and 500, in the presence of DMSO, by Tissue Culture Infectious Dose 50 (TCID50) assay. Contaminating adenovirus from use of TERA in AAV production, at MOI 100 or 500, is presented as percentage infectious adenovirus determined relative to E1/E3 Ad5 control.

DETAILED DESCRIPTION OF THE INVENTION

Figure 1:
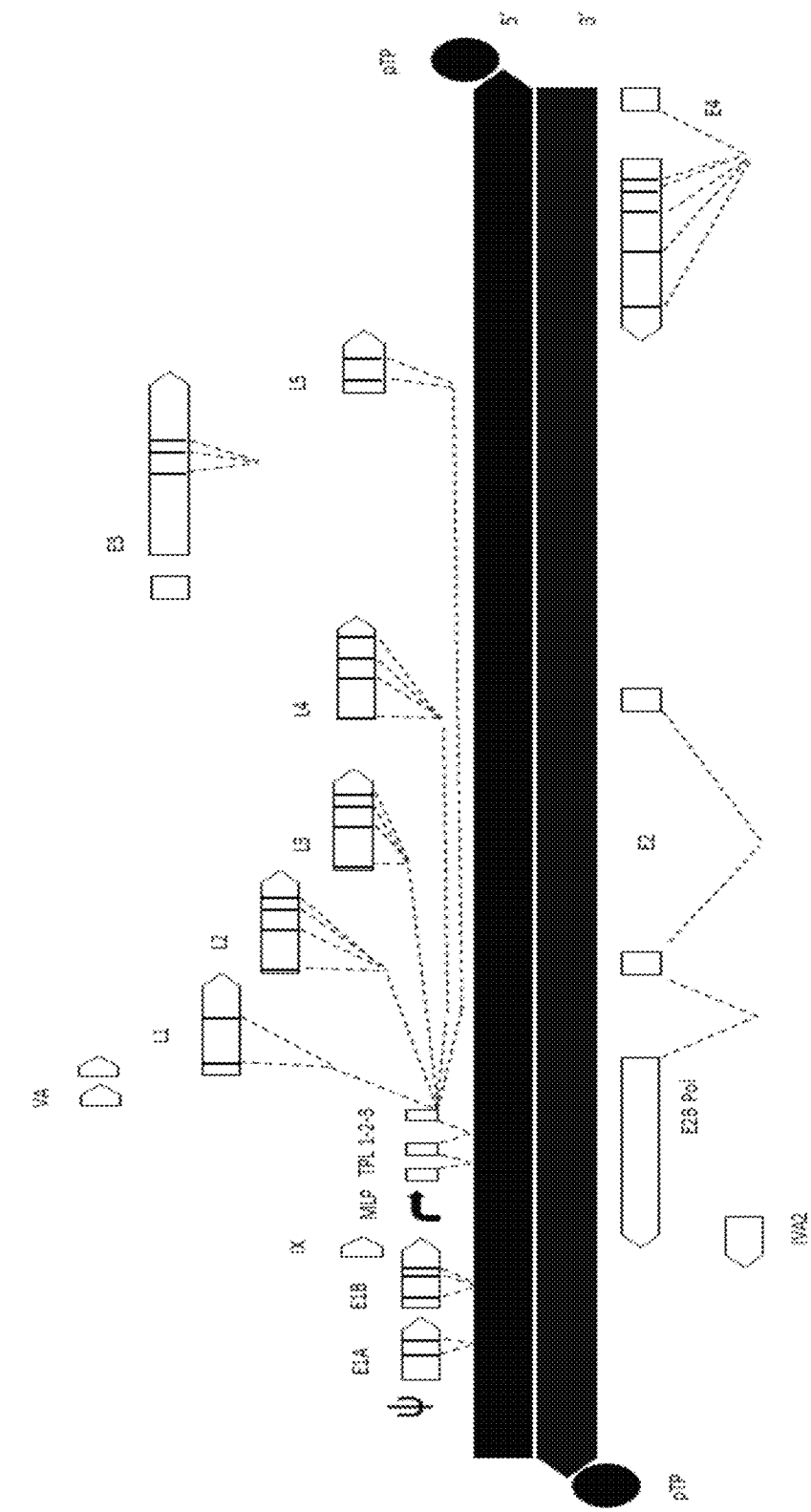
FIG. 1 shows a schematic diagram of the adenovirus genome and shows the main early and late expression regions. The MLP is also shown. Splice patterns are denoted by dotted lines.

In one embodiment, the invention provides an adenoviral vector comprising a repressible Major Late Promoter (MLP), wherein the MLP comprises one or more repressor elements which are capable of regulating or controlling transcription of the adenoviral late genes, and wherein one or more of the repressor elements are inserted downstream of the MLP TATA box.

In another embodiment, the invention provides an adenoviral vector comprising a repressible Major Late Promoter and an exogenous transgene.

In another embodiment, the invention provides an adenoviral vector comprising:
(a) a plurality of adenoviral early genes, and
(b) a plurality of adenoviral late genes under the control of a Major Late Promoter (MLP), and
(c) a transgene,
wherein the MLP comprises one or more repressor elements which are capable of regulating or controlling transcription of the adenoviral late genes.

Preferably, a gene encoding a repressor protein which is capable of binding to the repressor element is encoded within the adenoviral genome.

Preferably, the transgene comprises a Tripartite Leader (TPL) in its 5'-UTR.

Preferably, the presence of the repressor element does not affect production of the adenoviral E2B protein.

Preferably, the repressor protein is transcribed from the MLP.

Preferably, the one or more repressor elements are inserted between the MLP TATA box and the +1 position of transcription.

Adenovirus is the most commonly investigated and exploited virus in modern scientific research. It has found utility in the fields of vaccination, gene therapy, virotherapy, and also as complex tools for understanding biological systems (McConnell et al., 2004).

The adenoviridae family of viruses are double stranded DNA viruses which were first isolated from the adenoids of infected children in 1953 (Rowe et al., 1953). The family consists of many species infecting a broad variety of hosts including humans, birds and amphibians and is divided into four genuses to reflect the wide variety of hosts they infect.

The mastadenoviridae consists of 25 unique adenovirus species infecting mammalian hosts. Within this genus there are currently seven distinct species of adenovirus that infect humans. They are denoted by a letter as human adenoviruses A-G. Within these species multiple serotypes have been identified that are numbered from 1-57 and are all recognised as independent strains by the International Committee on the Taxonomy of
Viruses:
Species A: 12, 18, 31
Species B: 3, 7, 11, 14, 16, 21, 34, 35, 50, 55
Species C: 1, 2, 5, 6, 57
Species D: 8, 9, 10, 13, 15, 17, 19, 20, 22, 23, 24, 25, 26, 27, 28, 29, 30, 32, 33, 36, 37, 38, 39, 42, 43, 44, 45, 46, 47, 48, 49, 51, 53, 54, 56
Species E: 4
Species F: 40, 41
Species G: 52

Adenoviruses are small (approximately 90 nm in diameter) non-enveloped viruses with an icosahedral capsid with 12 fibres projecting from the icosahedron vertices. The virus consists of 240 hexon trimers, 12 penton pentamers, 60 IIIa monomers, 12 fiber trimers, 60 VII hexamers, 80 IX trimers as well as two terminal repeat proteins and multiple core proteins. Many of the latter are essential for intracellular trafficking and proteolytic cleavage of endocytosed viral capsids.

The DNA genome of adenovirus varies in length dependent on serotype but is typically 34-36 kilobases in length. The adenovirus serotype five genome is usually 35938 base pairs with a 103 base pair terminal repeat at each end and a 58% GC content. The genome is linear within the capsid structure and for the majority of the replication cycle but can form pan-handle circular structures within the nucleus during genome replication.

The process of cell attachment for adenoviruses varies dependent on the serotype. Adenovirus species C (including serotypes two and five) have been shown to attach to cells via their fibre domain binding to the cell surface coxsackie and adenovirus receptor (CAR) (Tomko et al., 1997) which is a component of cellular tight junctions (Honda et al., 2000). This initial interaction is high affinity and is followed by a lower affinity interaction between the virus penton base and cell surface integrins (αVβ3 & αVβ5) which are abundant on epithelial cells (Wickham et al., 1993). Following absorption to the cell surface virions are endocytosed and in a poorly defined step the virus capsid escapes from the endosome into the cytosol. Within the cytosol adenoviral capsids bind to the microtubule network and are transported via a Dynein dependent mechanism to the nucleus where the DNA is delivered into the nuclear lumen following capsid interaction with the nuclear pore complex (Trotman et al., 2001; Kelkar et al., 2004).

Our understanding of adenovirus genetics, transcription and translation is primarily derived from virological studies using adenovirus species C serotype five. The sequential process of gene transcription from the adenovirus genome reflects the protein requirements of the virus at each stage of the replication process. The transcription from the adenovirus genome is therefore divided into early and late events dependent on the timing of initiation of transcription from each viral promoter (FIG. 1). The first proteins produced from the virus genome are the E1A proteins. The E1A transcription unit produces multiple mRNA molecules through alternative splicing which in turn produce multiple proteins ranging from 6-36 kDa. The E1A proteins have two major roles within an infected cell. Firstly, they induce the cell to enter the S phase of the cell cycle to allow the efficient replication of the viral genome. Secondly, they induce transcription of the other early promoters within the viral genome through transactivation. These promoters control the production of the E1B, E2, E3, E4 and E5 proteins. E1A expression is immediately followed by VA RNA and E1B and E3 protein production. These proteins and RNA molecules help to prevent the development of an anti-viral response. These early events in viral replication help to shape the intracellular environment to allow the replication of the viral genome before packaging. Later transcription events involve the production of structural proteins and proteins essential for cell lysis which are derived primarily from a single promoter (the major late promoter) which transcribes the late regions 1-5. Cell lysis is dependent on the E3-11.6K protein (also termed the adenovirus death protein) which despite its labelling as an early gene is only produced late in infection and from the major late promoter (Tollefson et al., 1996).

Adenovirus genes are divided into early (E1-4) and late (L1-5) transcripts, with multiple protein isoforms driven from a range of splicing events. The early regions are divided into E1, E2, E3 and E4. E1 is essential for transitioning the cell into a phase of the cell cycle that is conducive to virus replication and inhibiting apoptosis and promoting cell division. The E2 region is largely responsible for the replication of the DNA genome, containing the DNA binding protein (E2A), the terminal protein and the DNA polymerase (E2B). E3 contains genes involved in immune regulation of host responses and E4 contains a range of genes involved in regulating cell pathways such as non-homologous end joining (NHEJ) and complexing with E1B-55K to mediate p53 degradation.

The adenovirus late genes are all transcribed from the same promoter, the Major Late Promoter and all share the same 5' mRNA terminus which contains three exons that collectively form the tri-partite leader sequence. The late genes are expressed by a series of splice events that allow the expression of approximately 13 proteins that either form a part of the virus particle (e.g. Hexon and Fibre) or involved in its assembly (e.g. 100K protein).

Adenoviral vectors are vectors which are based on or derived from the genome of a virus of the family *Adenoviridae*. Preferably, the adenovirus is a human adenovirus from group A, B, C, D, E, F or G. More preferably, the adenovirus is a human adenovirus from group B or C or D. Even more preferably, the adenovirus is a human adenovirus from groups B or C.

The adenoviral vector comprises a plurality of adenoviral early genes (FIG. 1).

The E1A proteins are the translation products of the first gene transcription events from the adenovirus genome within the nucleus at the E1A region. This initial transcription is driven by a strong constitutively active enhancer element within the E1A promoter and allows significant quantities of E1A mRNA to be produced. They are one of two sets of proteins in the adenovirus genome which are capable of inducing transformation with E1B proteins also able to induce cell cycle progression. E1A and E1B genes are essential for virus replication.

The E2 genes are divided into two sections in the adenovirus genome: the E2A and the E2B regions, and both are required for virus replication. E2B contains the DNA polymerase gene which is fundamentally required for the amplification of the virus genomic DNA. Similarly, this region also contains the Terminal protein which is required for the initiation of virus genome replication. The terminal protein is covalently attached to the end of the virus genomic DNA. The E2A region contains a DNA binding protein that is required for DNA replication. All E2 genes are fundamentally required for virus replication.

The E3 genes are primarily involved in regulating cell and host immune responses to virus infection, however, as the majority of viruses used for biotechnology applications are in vitro many, if not all, of these virus genes can be removed without reducing virus replication efficiency. The majority of the E3 genes are not essential for virus replication. However, some genes such as the Adenovirus Death Protein (ADP) are required for efficient replication and virus production.

The E4 region of the adenovirus genome is similar to the E1 region in that it is primarily involved in producing proteins that help the virus control and regulate the cell to ensure efficient virus replication and production. The region includes 6 open reading frames (ORFs) that are able to aid in preventing non-homologous end joining and apoptosis amongst a number of other discrete functions. The relative importance of each E4 transcript to virus replication is variable with some being essential whilst others can be deleted or modified with little to no effect on virus growth kinetics and production.

The adenoviral vector of the invention preferably comprises sufficient adenoviral early genes in order for the adenovirus to be capable of replicating the viral genome in the nucleus of a cell in which it is placed.

The adenoviral vector comprises a plurality of adenoviral late genes (FIG. 1).

The virus late genes are divided into five main transcript families named L1-L5. These transcripts primarily encode proteins that are involved in virus assembly and the structural proteins of the virus. During virus replication they can represent as much as 30-40% of the cells protein content (Garnier, 1994; Ginsberg, 1984).

The L1 series of transcripts encode for the 13.6 K, 52 K, and PIIIa proteins. These proteins are all involved in virus assembly and particle production. L1 genes are required for successful virus assembly but not genomic DNA replication.

The L2 series of transcripts encode for the penton base, pVII, V, pX proteins. These form structural parts of the virus capsid and are required for the particle to assemble correctly. Penton base contains an RGD motif that is important for virus attachment to the cell surface during infection. L2 genes are required for successful virus assembly but not genomic DNA replication The L3 series of transcripts encode for the pVI, hexon, and protease proteins. The Hexon protein is a major component of the virus capsid and is antigenically diverse between serotypes. The protease protein is involved in cellular entry and the virus capsid maturation. L3 genes are required for successful virus assembly but not genomic DNA replication The L4 series of transcripts encode the 100K, 33K, 22K, pVII proteins. These proteins are involved in a range of functions. 100K protein is involved in both aiding virus hexon assembly and nuclear import but may also play a role in shifting cell mRNA translation to cap-independent translation. In one embodiment of the invention, the 100K protein may be provided in trans within a cell rather than from within the virus genome. The 22K protein is involved in virus encapsidation. L4 genes are required for successful virus assembly but not genomic DNA replication. However, the 100K protein may aid in shifting cellular protein translation towards those transcripts that contain a tripartite leader (TPL) sequence.

As such, in one embodiment of the invention, the expression of the 100 K protein may not be controlled by the MLP. The 100 K protein in one embodiment may be transferred to another position in the virus genome not under the control of the MLP. In another embodiment, the 100 K protein may be transferred to a separate virus. In another embodiment, the 100 K protein may be transferred to the chromosome of a cell or provided in trans by DNA transfection or electroporation.

L5 encodes the Fibre gene. Fibre is a virus structural protein involved in attachment to cell surfaces and in mediating virus cellular infection. The Fibre protein is produced in significant excess of its requirement for virus particle formation. An embodiment of the invention may silence a minimum of one of either Fibre or Hexon (L3) proteins as these are some of the most abundant proteins produced during virus replication. L5 genes are required for successful virus assembly but not genomic DNA replication The adenoviral vector of the invention comprises sufficient adenoviral late genes in order for the adenovirus to be capable of being packaged in a cell to produce virus particles capable of infecting another mammalian cell. The virus genome will contain at least one late transcript generated from the Major Late promoter. Some proteins may be removed and provided in trans and others may be transferred into a host cell chromosome.

In the wild-type adenoviral genome, a single Major Late Promoter (MLP) is responsible for promoting the parallel transcription of the adenoviral late transcripts, L1-L5 (FIG. 1). The adenoviral vector of the invention also comprises a MLP. The MLP is situated at the 5'-end of these late transcripts.

Multiple mRNAs are produced from the late transcripts via differential use of 3'-splice and poly(A) sites. All of these transcripts contain the tripartite leader (TPL) sequence.

Figure 2:
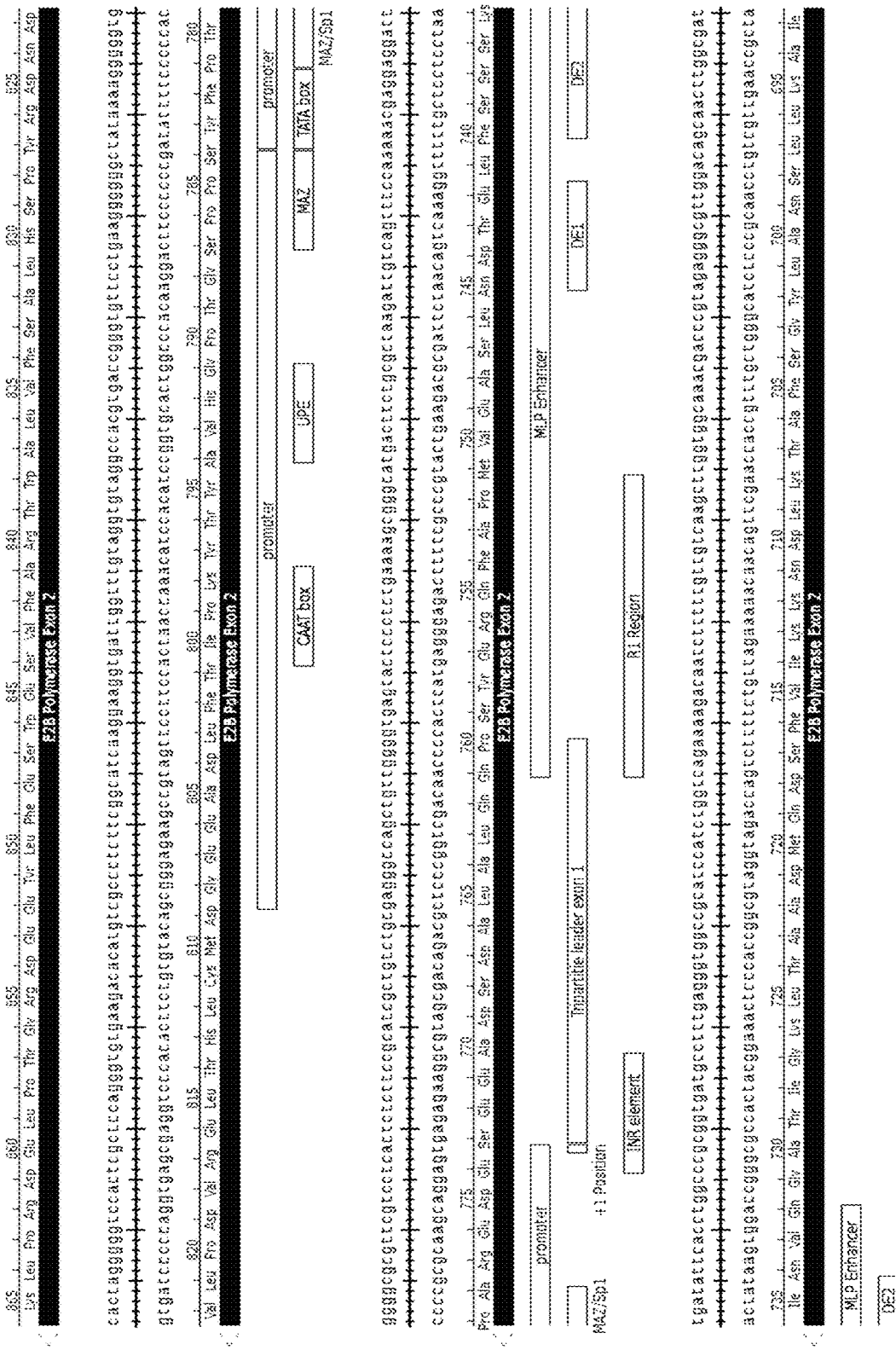
FIG. 2 shows annotated sequences (SEQ ID NOs: 12-14) of the major late promoter region of wild type adenovirus serotype 5.

FIG. 2 shows an annotated sequence of the major late promoter. Key features in the promoter include a number of transcription factor binding sites. This includes a CAAT box, a UPE box, a TATA box, a MAZ/SP1 binding site, a +1 position of transcription, and INR element, and an enhancer region containing an R1 region, DE1 and DE2 sub-region. These features have been shown to be important to varying degrees for major late promoter activity. Key features that are known to significantly reduce promoter activity if modified or deleted are the TATA box, INR element, the R region and DE1 and DE2 regions. The TATA box is considered the single most important feature, with transcription initiation occurring at the $28^{th}$ base pair after the last base of the TATA sequence itself.

The nucleotide sequence of the wild-type Ad5 MLP is given below:

(SEQ ID NO: 1)
cgccctcttcggcatcaaggaaggtgattggtttgtaggtgtaggccacg tgaccgggtgttcctgaagggggg<u>ctataaaagggggtgggggcgcgttc</u> gtcctca

The TATA box is underlined in the above sequence and the final base (in bold) denotes the position of transcription initiation (i.e. the +1 position).

In the adenoviral vector of the invention, the MLP comprises one or more repressor elements. The repressor element(s) are capable of regulating or controlling transcription of the adenoviral late genes. Preferably, the repressor element(s) are capable of repressing transcription of the downstream adenoviral late genes.

One or more repressor elements may be present in the MLP. Preferably, there are 1, 2, 3 or 4 repressor elements; more preferably 1 or 2.

In some embodiments, one or more (preferably one) repressor elements are located downstream of the MLP's TATA box. In other embodiments, one or more (preferably one) repressor elements are located upstream of the MLP's TATA box. In other embodiments, one or more (preferably one) repressor elements are located upstream of the MLP's TATA box and one or more (preferably one) repressor elements are located downstream of the MLP's TATA box.

Preferably, the one or more repressor elements are all placed upstream of the +1 transcription start site. More preferably, the one or more repressor elements are inserted between the MLP TATA box and the +1 position of transcription. Even more preferably, the start of one or more repressor elements is placed less than 27 nucleotides, more preferably less than 20 nucleotides, and even more preferably less than 10 nucleotides downstream of the TATA box.

The repressor is a DNA binding protein. The repressor will either bind to DNA and directly inhibit the recruitment of transcription factors required for transcription initiation, or the repressor will sterically hinder the initiation of transcription by occupying a key footprint on the DNA that prevents transcription factors that are required for transcription initiation from binding. The repressor may be regulated by a small molecule that causes a conformational shift in the repressor protein that either enables, or prevents, its DNA binding. The repressor is not an activator.

Promoters regulated by a repressor are typically induced by the presence or absence of biotic or abiotic factors.

Examples of proteins that could be used as repressors in the context of this invention include the tetracycline repressor, the lactose repressor, the ecdysone repressor, rat glucocorticoid receptor, human estrogen receptor, alcohol dehydrogenase I (alcA), metallothionein (proteins that bind and sequester metal ions), salicylic acid, ethylene and benzothiadiazole (BTH).

Preferably, the repressor is the tetracycline repressor, the lactose repressor or the ecdysone repressor. Most preferably, the repressor is a Tet repressor protein (TetR).

The TetR binding site may have a wild-type sequence. Preferably, the TetR binding site has been subject to one or more improvements by incorporating minor sequence changes. A preferred version that can be used in an embodiment of the invention has the sequence:

(SEQ ID NO: 2)
tccctatcagtgatagaga

Alternative versions of the repressor element that bind the TetR protein or derivatives of the TetR protein may also be used in an embodiment of the invention provided that the TetR repressor protein binds to the TetR binding sequence variant used. Some repressor/binding site variants will have higher than wild-type affinity for each other; these are preferable in an embodiment of the invention.

In one embodiment of the invention, the DNA sequence of the TetR protein is:

(SEQ ID NO: 3)
Atgtcgcgcctggacaaaagcaaagtgattaactcagcgctggaactgtt gaatgaggtgggaattgaaggactcactactcgcaagctggcacagaagc tgggcgtcgagcagccaacgctgtactggcatgtgaagaataaacgggcg ctcctagacgcgcttgccatcgaaatgctggaccgccatcacacccactt ttgcccctggagggcgaatcctggcaagattttctgcggaacaatgcaa agtcgttccggtgcgctctgctgtcccaccgcgatggcgcaaaagtgcac ctgggcactcggcccaccgagaaacaatacgaaaccctggaaaaccaact ggctttccttttgccaacagggattttcactggagaatgccctgtacgcac tatccgcggtcggccactttaccctgggatgcgtcctcgaagatcaggag caccaagtcgccaaggaggaaagagaaactcctaccactgactcaatgcc tccgctcctgagacaagccatcgagctgttcgaccaccagggtgctgaac ctgcatttctgttcgggcttgaactgattatctgcggcctggagaaacag ttgaagtgcgagtcgggatcctag or a sequence having at least 80%, more preferably at least 85%, 90% or 95% sequence identity thereto and which codes for a TetR protein.

In one embodiment of the invention, the amino acid sequence of the TetR protein is:

(SEQ ID NO: 4)
MSRLDKSKVINSALELLNEVGIEGLTTRKLAQKLGVEQPTLYWHVKNKRA

LLDALAIEMLDRHHTHFCPLEGESWQDFLRNNAKSFRCALLSHRDGAKVH

LGTRPTEKQYETLENQLAFLCQQGFSLENALYALSAVGHFTLGCVLEDQE

HQVAKEERETPTTDSMPPLLRQAIELFDHQGAEPAFLFGLELIICGLEKQ

LKCESGS or a sequence having at least 80%, more preferably at least 85%, 90% or 95% sequence identity thereto and which encodes a TetR protein.

When TetR is bound to the repressor element (e.g. repressor binding site), tight suppression of transcription is obtained. However, in the presence of doxycycline, suppression is alleviated, thus allowing the associated promoter to regain full transcriptional activity. Doxycycline is preferable over tetracycline.

The repressor element may be introduced into the MLP by modification of the MLP sequence. The repressor element may be introduced by insertion of a repressor element into the MLP sequence; by substitution of one or more nucleotides in the MLP sequence to create a repressor element sequence; or by a combination of insertion/deletion of a new sequence.

In one embodiment of the invention, the distance between the TATA box and the +1 position of DNA transcription of the MLP is maintained (+/−5%), but a repressor binding site is inserted between the two. Within this region, there is a MAX/SP1 binding site.

Figure 3:
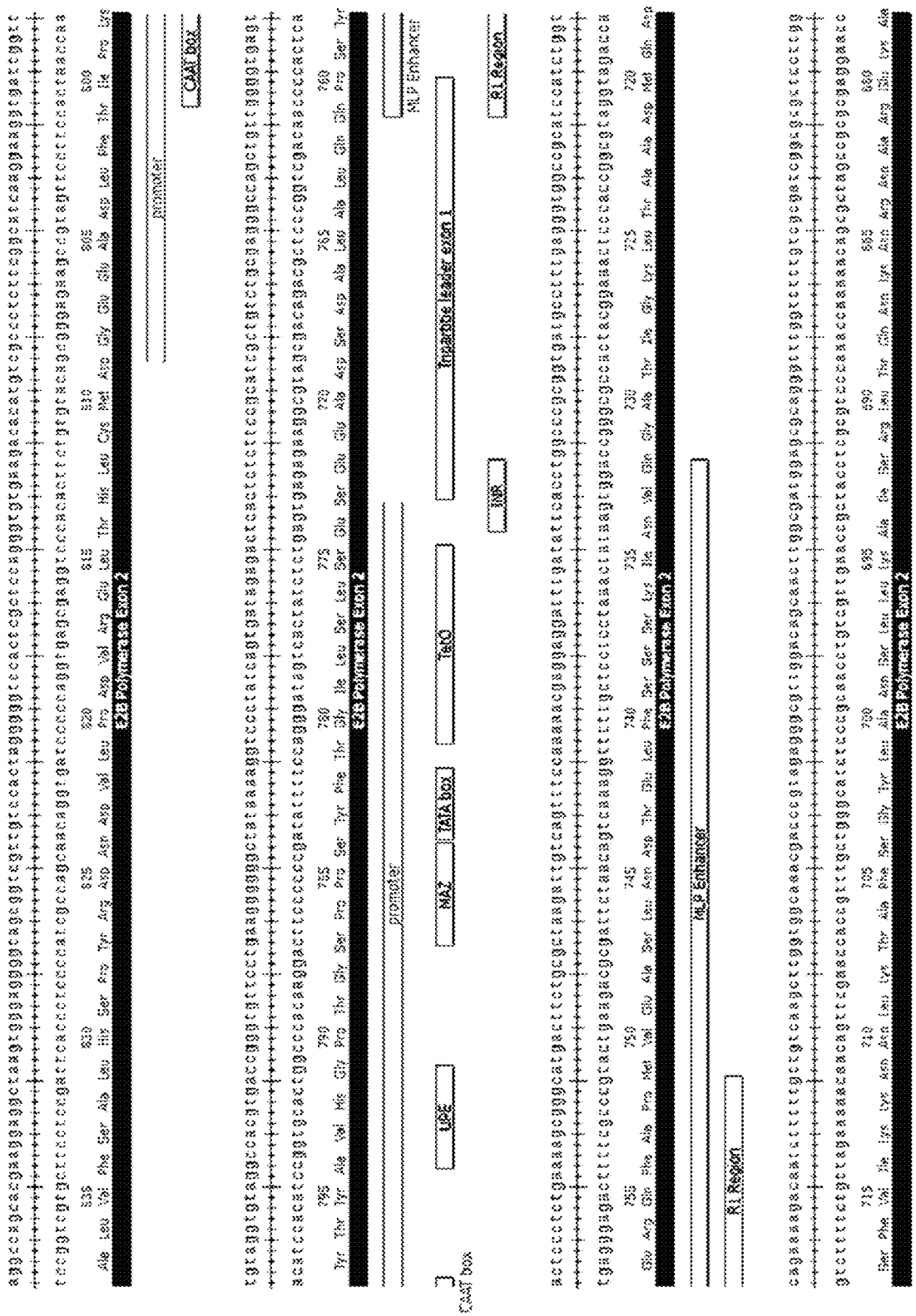
FIG. 3 shows annotated sequences (SEQ ID NOs: 15-17) of the modified major late promoter region of adenovirus serotype 5.

This site is not fundamental to MLP expression and therefore, in one embodiment of the invention, it can be replaced. FIG. 3 shows an embodiment of the invention where the region between the TATA box and the +1 position of transcription has been replaced with a binding site for the tetracycline repressor protein (TetR).

In some adenoviral vectors, the section of the DNA strand which is opposite to that of the MLP sequence encodes the early viral protein E2B (which encodes the viral DNA polymerase). In order to maintain the ability of such adenoviral vectors to replicate their genomes, it is necessary to ensure that the modifications which are made to the MLP sequence do not significantly adversely affect the production, stability or efficacy of the E2B protein.

In Adenovirus serotype 5, the MLP resides in the middle of the E2B polymerase Exon 2. As such, in one embodiment of the invention, the insertion of a repressor element (e.g. repressor binding site) into the MLP must maintain the coding frame of the DNA polymerase coding sequence in the opposing DNA strand or ensure that the modifications which are made to the MLP sequence do not significantly adversely affect the production, stability or efficacy of the E2B protein.

Preferably, some or all of the changes to the MLP sequence are silent changes, i.e. they do not change the E2B codons. In other embodiments, some or all of the changes to the MPL are conservative changes, i.e. one or more E2B codons are changed such that they encode an amino acid having a similar side chain.

Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the E2B protein can be replaced with other amino acid residues from the same side chain family and the altered E2B protein can be tested for any significant loss in function or activity.

In one embodiment of the invention, a TetR binding site is positioned into the MLP between the TATA box and the +1 position. FIG. 2 shows the coding sequence of the DNA polymerase. In the region between the MLP TATA box and the +1 position, the amino acid coding sequence of the DNA polymerase is ENERAPTP (SEQ ID NO: 18). FIG. 3 shows that the strategic placing of a TetR binding site into this region creates a sequence ESLSLIGT (SEQ ID NO: 5). This sequence maintains the reading frame of the DNA polymerase but also allows for more than 60% of the wild type amino acids to be exchanged for those with similar side chains. Importantly, the sequence of the TetR binding site contains stop codons in the opposing DNA strand if positioned incorrectly which would likely create a non-functional DNA polymerase.

In one embodiment of the invention, therefore, the sequence on the opposite strand of the TetR binding site is or comprises a sequence encoding ESLSLIGT (SEQ ID NO: 5). Preferably, the DNA polymerase comprises a sequence of SEQ ID NO: 5.

Some loss in amount of E2B mRNA or protein produced may be tolerated, as may some changes in the amino acid sequence of the E2B protein. The skilled person will readily be able to assess the effect of changes on the E2B gene sequence on the ability of the virus to replicate simply by assessing the viral titre of a modified adenoviral vector under standard conditions in comparison to the original unmodified virus. Changes which reduce the viral titre by less than 25%, preferably less than 10% and more preferably less than 1% may be considered to be ones which do not significantly adversely affect the production, stability or efficacy of the E2B protein.

In other adenoviral vectors of the invention, the E2B gene is positioned elsewhere in the adenoviral vector such that modifications in the MLP do not affect the production of the E2B protein.

An example of a modified MLP which contains one TetR binding site between the TATA box and the +1 position of transcription is given below:

(SEQ ID NO: 6)
Cgccctcttcggcatcaaggaaggtgattggtttgtaggtgtaggccacg tgaccgggtgttcctgaagggggg<u>ctataaaagg</u>tccctatcagtgatag agactca

The TATA box is underlined and the TetR binding site is shown in bold.

An example of a modified MLP which contains one TetR binding site between the TATA box and the +1 position of transcription and a second site upstream of the TATA box between the UPE element and the TATA box is shown below:

(SEQ ID NO: 7)
Cgccctcttcggcatcaaggaaggtgattggtttgtaggtgtaggccacg tgactccctatcagtgatagagaac<u>tataaaagg</u>tccctatcagtgatag agactca

The TATA box is underlined and the TetR binding site is shown in bold.

The repressor which binds to the repressor element(s) may be applied exogenously (to the cells); it may be encoded within the cellular or mitochondrial genome (or a plasmid or vector within the cell); or it may be encoded within the adenoviral genome. Preferably, the repressor is encoded by a gene within the adenoviral genome.

More preferably, the repressor gene is located within one or more of the viral early expression regions or the late gene expression regions. Even more preferably, the repressor gene is located in the virus late region. Even more preferably the repressor is located in a late transcript that is transcribed from an MLP that is regulated by the repressor. The system is thereby self-repressing.

In one embodiment, the gene encoding the repressor protein is under the control of an independent promoter (i.e. a promoter which is not the adenoviral major early promoter or major late promoter). Preferably, the gene encoding the repressor protein is under the control of a strong promoter (e.g. the cytomegalovirus (CMV) promoter). Even more preferably, the repressor protein is under the control of the MLP to which it binds.

Preferably, the mRNA encoding the repressor protein comprises a Tripartite Leader (TPL) sequence in its 5'-UTR. TPL is a 5' untranslated sequence which is present in all of the late, but none of the early, viral mRNA. TPL facilitates mRNA transport and accumulation in the cytoplasm and is responsible for the selective translation of the late viral proteins in preference to the cellular proteins.

The Ad5 leader sequence is 201 bp formed by the splicing of three exons during the post-translational modifications.

The adenoviral vector of the invention comprises at least one transgene. A key function of the adenoviral vector of the invention is to facilitate production of the transgene product.

During adenoviral infection up to 90% of the mRNAs can be from the viral genome and these can be preferentially translated to maximise virus output. The selective production of virus specific mRNA is down to a combination of the amplification of the virus DNA polymerase and a shift towards the production of late mRNA transcripts. The replication of the virus DNA genome allows for thousands more copies of the DNA template for transcription to occur from. This activity, coupled with the presence of the tri-partite leader at the 5' end of late transcripts, allows the selective expression of late mRNA. This is because the tripartite leader, whilst highly active in normal translation processes, is also selectively translated when cap-independent translation is turned on within a cell. Multiple virus proteins are involved in this process.

Preferably, the transgene is inserted within one of the adenoviral early regions. More preferably, the transgene is inserted within the adenoviral E1 region. Even more preferably, the E1A and E1B genes are deleted from the Adenovirus genome and the transgene is inserted into this region. Preferably, the transgene comprises a TPL sequence in its 5'UTR. This ensures that the transgene is expressed in a cap-independent manner.

The transgene may be any desired DNA sequence. There may be more than one transgene (e.g. 2, 3, 4, or 5 transgenes). The DNA sequence of the transgene(s) may be a coding or non-coding sequence. It may be genomic DNA or cDNA. Preferably, the DNA sequence encodes a polypeptide, more preferably a therapeutic polypeptide. In some cases, the transgene will encode multiple proteins. Preferably, the transgene is operably associated with one or more transcriptional and/or translational control elements (e.g. an enhancer, promoter, terminator sequence, etc.).

A polypeptide encoded by a transgene could be a human gene or modified form thereof or encode a protein from a virus that infects human cells.

Examples of preferred therapeutic polypeptides include antibodies, CAR-T molecules, scFV, BiTEs, DARPins and T-cell receptors and antigens from human viral pathogens.

In some embodiments, the therapeutic polypeptide is a G-protein coupled receptor (GPCR), e.g. DRD1. In some embodiments, the therapeutic polypeptide is an immunotherapy target, e.g. CD19, CD40 or CD38. In some embodiments, the therapeutic polypeptide is a functioning copy of a gene involved in human vision or retinal function, e.g. RPE65 or REP. In some embodiments, the therapeutic polypeptide is a functioning copy of a gene involved in human blood production or is a blood component, e.g. Factor IX, or those involved in beta and alpha thalassemia or sickle cell anaemia. In some embodiments, the therapeutic polypeptide is a functioning copy of a gene involved in immune function such as that in severe combined immunedeficiency (SCID) or Adenosine deaminase deficiency (ADA-SCID). In some embodiments, the therapeutic polypeptide is a protein which increases/decreases proliferation of cells, e.g. a growth factor receptor. In some embodiments, the therapeutic polypeptide is an ion channel polypeptide. In some preferred embodiments, the therapeutic polypeptide is an immune checkpoint molecule. Preferably, the immune checkpoint molecule is a member of the tumour necrosis factor (TNF) receptor superfamily (e.g. CD27, CD40, OX40, GITR or CD137) or a member of the B7-CD28 superfamily (e.g. CD28, CTLA4 or ICOS). In some embodiments the polypeptide encoded is an immune checkpoint molecule, e.g. PD1, PDL1, CTLA4, Lag1 or GITR.

In some embodiments the transgene encodes a virus polypeptide or multiple thereof such as the antigenically important CMV pentamer.

In other embodiments, the transgene or transgenes will encode proteins involved in the replication or structure of viruses other than Adenovirus.

Most vaccines are composed of a collection of viral proteins: either a virus-like particle (VLP), inactivated virus particle or a live attenuated virus. VLPs have the advantage of typically being composed entirely of protein and as such have none of the potential pathogenicity of the original virus. They also have the advantage over inactivated virus particles that their structure is the same as the original virus and has not been altered by the inactivation process. A number of VLPs have been shown to be successful vaccines including HPV, Hepatitis B and the Malaria vaccine RTSS. However, production in mammalian systems is often lower than required to make the VLP a commercially-viable product. An example of this is the observation that the Hepatitis B vaccine VLP is manufactured in Yeast. A system to generate VLPs in large quantities in mammalian cells is therefore desirable to ensure proper folding and glycosylation.

In some embodiments, the transgene of the invention will encode proteins that will assemble in, or outside, of the cell to produce VLPs. These VLPs may make useful vaccine products.

In a preferable embodiment, the transgenes will encode proteins from Parvoviridae (e.g. adeno-associated virus), Retroviridae (e.g. HIV), Flaviviridae (e.g. Hepatitis C virus) and Orthomyxoviridae (e.g. Influenza virus), and/or Caliciviridae (e.g. Norovirus). In a preferred embodiment, the transgene will encode Norovirus VP1 or Hepatitis B HBsAG.

Recombinant adeno-associated viruses (rAAV) are in many ways ideal vectors for the delivery of transgenes to cells for recombinant protein production or gene therapy applications. They are able to infect a wide range of hosts, elicit a robust and sustained transgene expression profile, whilst exerting minimal toxicity to the host cell. AAV is a helper-dependent DNA parvovirus that requires helper function for completion of its natural life cycle. These helper functions may be provided by many agents that include co-infection with vaccinia viruses, herpesviruses or adenoviruses. In the absence of helper agents and functions, AAV infection enters a latent phase wherein the AAV viral genome is integrated into the host cell chromosome. Subsequently, in the presence of a helper virus, the integrated AAV provirus is rescued allowing viral replication, packaging in preformed protein capsids and production of infectious virions.

In current approaches to using AAV as a biotechnology tool for DNA delivery, AAV is engineered to replace the viral rep and cap coding sequence region with the transgene of interest for delivery into target cells. The rep and cap gene sequences required for replication, integration and expression of viral capsids are supplied in trans by DNA expression plasmids, viral vectors or cell lines which are engineered to stably express these genes from the host genome.

A traditional method of rAAV production involves cotransfection of two DNA vectors: 1) a plasmid containing the rAAV sequences; and 2) a plasmid containing AAV rep and cap sequences. Subsequently, helper functions can be provided in trans by infection with an adenovirus or herpes virus. The amount of rep proteins required for efficient rAAV production is unclear. While it was reported that attenuation of the translation initiation codon for Rep78/68 led to high levels of rAAV production (Li et al., 1997 J. Virol. 71:5236-5243), others have reported the exchange of the p5 promoter responsible for transcription of AAV rep with strong viral promoters, such as the human immunodeficiency virus long terminal repeat (HIV LTR) have resulted in the production of high levels of rAAV (see U.S. Pat. No. 5,658,776). Since the discussed methods required the co-transfection of two plasmids and co-infection with a helper virus e.g. adenovirus, to produce rAAV, reproducibility and batch variation are significantly problematic. Additionally, rAAV are required to be purified from helper agents (e.g. adenoviruses) for downstream and industrial application. The final preparation also has to be free from the helper virus proteins, particularly those that are antigens from the helper virus as this could affect the human response to such an AAV product.

A second method required for production of rAAV involves the co-transfection of three DNA plasmid vectors into producer cell lines. The cis plasmids contain: the 1) rAAV ITRs and transgene; 2) a trans DNA plasmid encoding the AAV rep and cap; and 3) a trans DNA plasmid encoding sequences from a helper virus (e.g. adenovirus). While this method has the advantage of being free of contamination from helper virus particles, co-transfection of three DNA plasmids with significantly large sizes results in poor reproducibility and substantial drop in rAAV viral titre yield.

A third method involves the construction of rAAV packaging cell lines where the rep and cap gene sequences are integrated into host cell genome. Typically, rAAV is produced from this method by transfection of the DNA cis plasmid encoding the AAV ITRs and transgene, followed by introduction of the helper agent (e.g. infection with helper adenoviruses). Alternatively, the helper viruses carrying the cis DNA AAV ITRS and transgenes (e.g. hybrid Ad/AAV) can be introduced into producer cell lines for production of rAAV (see U.S. Pat. No. 5,856,152).

The disadvantage of this method is that it requires complex engineering of producer cell lines wherein the AAV rep and cap are stably integrated and expressed to a sufficient amount. Additionally, use of helper viruses for delivery of the cis DNA sequence (e.g. AAV ITRS and transgenes) results in contamination from helper viruses and requires downstream purification. Furthermore, toxicity of the AAV rep protein in cell lines have been reported and constitutive expression results in anti-proliferation and cell death (Yang et al., 1994 J. Virol. 68(8), 4847-4856). Additionally, the Rep protein was also reported to induce a negative feedback loop for repression of its own transcription (Beaton et al., 1989 J. Virol. 63,450-4454). Other attempts to circumvent AAV rep toxicity by modification of packaging cell lines to expressed Rep have used an inducible transcription system (see U.S. Pat. No. 5,837,484 and Ogasawara et al., 1999 J. Virol. 80, 2477-2480). Typically, these stable systems have failed to yield the required level of AAV to make them commercially scalable systems.

A fourth method of producing rAAV involves the use of helper agents (e.g. helper adenoviruses) for delivery of the AAV rep and cap genes. In this method, the recombinant adenoviruses comprise rep and cap genes which are inserted into the genome of the helper virus (typically, in the E1 region of a recombinant adenovirus). These are subsequently used for infection into packaging cell lines that may contain the cis AAV DNA sequence (e.g. AAV ITRs and transgene) or the cis DNA plasmids can be introduced by methods of transfection (Zhang et al., 2001 Gene. Ther. 8(9), 704-712). The significant disadvantages of this method are similar to those of the traditional method of rAAV production, where difficult and costly purification steps are required for removal of contamination from the helper virus and any proteins (particularly structural proteins) from the final product.

In one embodiment of the invention, one or more transgenes in the adenoviral vector of the invention encodes an AAV Rep-Cap polypeptide. In another embodiment of the invention, one or more of the transgenes encodes an AAV genome. Preferably, the AAV genome comprises or consists of a 5' and 3' ITR sequence from AAV with intervening sequences. In another embodiment of the invention, one or more of the transgenes encodes a Rep-Cap polypeptide from an AAV and an AAV genome with ITRs flanking a sequence of interest. Rep or Cap or sub-transcripts or regions thereof may be encoded individually in an embodiment of the invention.

The adenoviral viral vector may additionally comprise, but not limited to, one or more other elements, selected from the group consisting of reporter genes, restriction enzyme sites, promoters, poly-adenylation signals, un-translated regions, enhancers and insulators.

In some embodiments, the adenoviral vector additionally comprises one or more multiple-restriction enzyme sites. These sites will most preferably be Type II and either 6 or 8 base pairs in length.

The invention also provides a composition comprising an adenovirus particle comprising an adenoviral vector of the invention, together with one or more physiologically-acceptable carriers, excipients or diluents. Examples of suitable physiologically-acceptable carriers, excipients or diluents for use with virus particles are well known in the art. Preferably, the composition comprises an adenovirus particle comprising an adenoviral vector of the invention in an aqueous buffer solution. Preferably, the aqueous buffer solution comprises $MgCl_2$ and/or glycerol.

The invention also provides a kit comprising an adenoviral vector of the invention, wherein the kit additionally comprises one or more additional components selected from the group consisting of (i) a cell line that allows the viral vector to infect the cells and replicate its genome, wherein the cell line will repress the viral vector's MLP and (ii) one or more DNA plasmids for aiding in the construction of the viral vector.

Preferably, the kit will comprise a plasmid containing the viral vector that contains sites for insertion of a transgene. More preferably there will be two plasmids: the viral vector plasmid and a shuttle plasmid to allow the easy manipulation of the viral vector. The shuttle plasmid will contain either regions of homology to the viral vector to allow homologous recombination to create a final viral vector, or restriction sites that are compatible with the viral vector to allow shuttling of DNA from the shuttle plasmid to the viral vector plasmid.

The kit may also contain materials for the purification of the viral particles such as those involved in the density banding and purification of viral particles, e.g. one or more of centrifuge tubes, benzonase, dialysis buffers, dialysis cassettes.

In other embodiments, the invention provides a viral vector (preferably an adenoviral vector) or a nucleic acid molecule comprising the nucleotide sequence:

```
                                              (SEQ ID NO: 8)
Aggccagcacgaaggaggctaagtgggaggggtagcggtcgttgtccact aggggggtccactcgctccagggtgtgaagacacatgtcgccctcttcggc atcaaggaaggtgattggtttgtaggtgtaggccacgtgaccgggtgttc ctgaagggggggctataaaaggtccctatcagtgatagagactcactctct tccgcatcgctgtctgcgagggccagctgttggggtgagtactccctctg aaaagcgggcatgacttctgcgctaagattgtcagtttccaaaaacgagg aggatttgatattcacctggcccgcggtgatgcctttgagggtggccgca
```

-continued tccatctggtcagaaaagacaatcttttgttgtcaagcttggtggcaaa
cgacccgtagagggcg or nucleotide sequence having at least 80%, more preferably at least 85%, 90% or 95% sequence identity thereto.

In some embodiments, the above-mentioned nucleotide sequence or sequence having identity thereto comprises the sequence tccctatcagtgatagaga (SEQ ID NO: 2)(i.e. the repressor element is not altered).

In other embodiments, the above-mentioned nucleotide sequence or sequence having identity thereto comprises a different repressor element to that shown in bold above.

The invention also provides a mammalian cell comprising an adenoviral vector of the invention. The cells may be isolated cells, e.g. they are not present in a living animal. Examples of mammalian cells include those from any organ or tissue from humans, mice, rats, hamsters, monkeys, rabbits, donkeys, horses, sheep, cows and apes. Preferably, the cells are human cells. The cells may be primary or immortalised cells. Preferred human cells include HEK293, HEK293T, HEK293A, PerC6, 911, HeLa and COS cells.

HEK-293 cells have been modified to contain the E1A and E1B proteins and this allows the creation of viruses that have a deletion of the E1A and E1B regions to be grown in this cell line by trans-complementation. Similarly, PerC6 and 911 cells contain a similar modification and can also be used. Most preferably, the human cells are HEK293, HEK293T, HEK293A, PerC6 or 911. Other preferred cells include CHO and VERO cells.

Adenoviral vectors may be produced by several methods, the most common of which involves homologous recombination of adenovirus plasmids in either mammalian cells or microorganisms, including bacteria and yeast. Two plasmids, termed a shuttle plasmid and an adenoviral (also called backbone) plasmid, are recombined into a DNA molecule that incorporates sequences from both plasmids. This DNA molecule can then be transfected into mammalian packaging cell lines to generate adenovirus particles.

In an embodiment of the invention wherein the MLP is regulated by a TetR protein, the virus is recovered in the presence of doxycycline which will inhibit the repressor protein and thereby prevent it from binding to the repressor element/site in the MLP promoter. This should allow for production of the adenovirus at high titres.

For protein production or the expression of virus proteins, infecting with the virus into any cell line that can be infected by adenovirus (e.g. HEK-293 cells), in the absence of doxycycline, will allow the expressed TetR repressor protein to bind to the MLP repressor element and thereby shutting down the production of virus late gene expression and preventing virus particle production.

The TetR protein can be provided within the cell line infected, either transiently or stably, or encoded within the virus itself. If under the control of the MLP then with each genome replication, activation of the MLP will provide a feedback loop, further shutting down any potential new virus late gene expression.

In a further embodiment, the invention provides a process for producing a modified mammalian cell, the process comprising the step:
(a) infecting a mammalian cell with an adenoviral vector of the invention, whereby the mammalian cell then comprises the adenoviral vector.

In yet a further embodiment, the invention provides a process for producing a transgene product, the process comprising the steps:
(a) infecting mammalian cells with an adenoviral vector of the invention;
(b) culturing the infected mammalian cells in a culture medium under conditions such that the transgene is expressed; and
(c) isolating or purifying transgene product from the cells or from the cell culture medium.

Suitable conditions for the culturing of infected mammalian cells are well known in the art.

Transgene product expression levels may be improved by the co-expression of the 100 kDa L4/eIF48 protein. Furthermore, the repressor protein needs to be active as a repressor (e.g. doxycycline is not present if the repressor protein is TetR).

The processes of the invention are preferably carried out in vitro or ex vivo.

The disclosure of each reference set forth herein is specifically incorporated herein by reference in its entirety.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Materials and Methods

The methods used for cloning and production of the adenoviral vectors were as follows.

Plasmid Amplification in Prokaryotic Systems

Transformation of *Escherichia coli* (*E. coli*) allowed amplification of plasmids and subsequent screening for desired final DNA clones. DNA transformation was performed by thawing *E. coli* cells on ice, followed by the addition of 5-100 ng of DNA per transformation. Cells were incubated in ice for 20 minutes followed by 3 minutes heat-shock at 37° C. LB medium (0.9 mL per sample) was added to each tube and incubated for a further 15 minutes at 37° C. Samples were either poured into nutrient agar plates containing selection antibiotic or 100 μL of each sample was streaked out to allow individual colony isolation.

Successfully transformed clones were amplified and selected using antibiotic resistance using the appropriate antibiotic in growth media. Bacterial culture broth and plates containing either Kanamycin (50 μg/mL, Kanamycin Sulfate, Invitrogen, UK) or Ampicillin (50 μg/mL, Ampicillin Sodium salt, Sigma Aldrich) were prepared using Lennox LB Broth Base (20 g/L) and Lennox LB Agar (32 g/L) (Invitrogen, UK), respectively. Single bacterial colonies obtained on culture plates after transformation were picked and grown overnight in broth (5 mL mini-prep or 250 mL maxi-prep) at 37° C. with agitation (200 rpm) using a Sanyo orbital incubator (SANYO Electric Biomedical Co. Ltd, USA).

Plasmids were purified by mini-prep using the QIAprep Spin Miniprep Kit (Qiagen, UK) or maxi-prep using the Qiagen High Speed Maxi-prep kit (Qiagen, UK). Plasmid clones were selected and confirmed by diagnostic restriction digestion and DNA sequencing.

Bacterial Cells

For the majority of small (<10 Kb) DNA constructs, DH5α *E. coli* bacteria (Invitrogen) were used to amplify plasmids. For larger (>10 Kb) constructs, XL10 Gold Ultra-competent *E. coli* bacteria (Stratagene) were used to amplify DNA. These cells have been engineered in order to allow the efficient delivery of large DNA plasmids via heat-shock treatment and reduce bias towards selecting for small plasmids libraries. For growing DNA which was free of DAM and DMC methylation at key restriction sites, JM110 *E. coli* (Stratagene) were used. These cells are deficient in methyl transferase enzymes and allow high purity methyl deficient DNA to be amplified. For recombination of DNA molecules, BJ5183 *E. coli* cells were used. These cells allow the recombination between two DNA molecules due to both the mutation of Endonuclease I and the expression of a RecET homologue which allows the efficient repair of double-strand breaks at homologous regions. All strains were grown in Lennox LB media or on LB agar plates at 37° C.

DNA Restriction Digests (Preparative and Qualitative)

Restriction endonucleases were used to generate diagnostic digestion patterns or to produce DNA molecules with sticky (non-blunt) ends or blunt ends, allowing subsequent ligation of DNA fragments with other DNA molecules with either blunt or compatible overhangs. All digestions were performed according to conditions specified by the manufacturer (enzymes were purchased from New England Biolabs, UK or Promega, UK). Where digestions were performed for molecular engineering purposes, DNA fragments of correct sizes were visualised by gel electrophoresis and purified either from excised gel bands using the QIAEX II Gel Extraction Kit for large fragments (>8 Kb) (Qiagen, UK) and the MinElute Gel Extraction Kit for small fragments (Qiagen, UK), or, where it was unnecessary to resolve fragments of different sizes, purified directly from the digestion reaction (QIAquick PCR Purification Kit). HyperLadder™ I (Bioline Ltd, UK) was used as a molecular weight marker for fragments ranging from 1-10 Kb. For larger DNA fragments a Lambda Hind3 digest ladder was used (New England Biolabs, UK). For fragments less than 1 Kb a 100 base pair ladder was used (New England Biolabs, UK).

DNA Ligation

Donor (insert) and recipient (vector) DNA were digested with single or double (for directional cloning) restriction enzyme(s) generating compatible overhangs for complementary base-pairing. Digested insert was gel-purified or cleaned up, while the vector was de-phosphorylated by treatment with 2 µL of calf intestinal alkaline phosphatase (37° C., 1 h) (Invitrogen, UK) to reduce background contamination resulting from vector re-ligation. Vectors were then purified using the MinElute Gel Extraction Kit (Qiagen, UK) or the QIAquick PCR Purification Kit (Qiagen, UK) using the manufacturer's protocols. All purified DNA was eluted in nuclease-free water. Ligation reactions were prepared using T4 DNA Ligase (New England Biolabs, UK) according to the manufacturer's protocol.

Heat Shock Competent Cells

Heat shock DNA competent *E. coli* cells were produced by inoculating a single colony of *E. coli* into 5 mL 2×YT broth media (16 g/L Bacto Tryptone, 10 g/L Yeast Extract, 5 g/L NaCl, pH 7.0 with 5M NaOH) which was shaken at 37° C. for 4 hours. This was transferred to 200 mL pre-warmed 2×YT media. When the culture reached OD 480 the cells were pelleted at 3000 rpm in a swing out centrifuge at 4° C. for 10 minutes. Cells were re-suspended in a total of 80 mL cold TFBI1 (30 mM $KC_2H_3O_2$ (Potassium acetate), 100 mM RbCl, 10 mM $CaCl_2.2H_2O$, 50 mM $MnCl_2.4H_2O$, 15% v/v glycerol, adjusted to pH 5.8 using 0.2 M $CH_3COOH$, filter sterile). Cells were spun as above and re-suspended in 8 mL of TFBI2 (10 mM MOPS, 10 mM RbCl, 75 mM $CaCl_2.2H_2O$, 15% v/v glycerol, adjusted to pH 6.6 using 5 M KOH, filter sterile). 100 µl of cells were pipette into pre-chilled 1.5 mL microfuge tubes and frozen on dry ice. Tubes were then transferred to −80° C. for long term storage.

Polymerase Chain Reaction (Cloning)

Polymerase chain reactions (PCR) were performed using oligonucleotide primers designed according to the requirements for molecular manipulation, sequencing or screening procedures (purchased from Sigma-Genosys, UK). Primer sequences employed for vector engineering and molecular characterisation purposes are described below.

For sub-cloning of DNA fragments generated by PCR amplification from DNA templates, high fidelity AccuPrime™ Pfx proofreading DNA polymerase (Invitrogen, UK) was used. For routine screening for the presence of specific DNA sequences by PCR, PCR SuperMix (Invitrogen, UK) was used. Primers were dissolved in de-ionised, nuclease-free water at 10 µM; 0.8-1 µL of each of the forward and reverse primers were used per PCR reaction. Reactions were carried out according to recommended protocols provided by the suppliers of enzymes and reagents. Where necessary, primer concentrations were varied and a gradient of annealing temperatures was run to determine optimal reaction conditions. PCRs were performed using a PTC-225 Peltier Thermal Cycler DNA Engine Tetrad (MJ Research, USA).

Agarose Gel Electrophoresis

Size fractionation of DNA on 1% (w/v) agarose (Invitrogen, UK) gels containing ethidium bromide (Sigma-Aldrich, UK) (0.5 µg/mL) in 0.5×TAE buffer (4.84 g Tris-base, 1.09 g glacial acetic acid, 0.29 g EDTA in 1 L) enabled visualisation of DNA and size estimation, by relative comparison to commercially available molecular weight markers described above. DNA molecules from purified plasmids or fragments from PCR reactions or restriction digestions were subjected to gel electrophoresis (10 volts per cm gel length, 30-120 minutes) in horizontal DNA electrophoresis gel tanks (Bio-Rad Laboratories Ltd, UK). DNA bands were visualised using a gel and fluorescent imaging system (Alphalmager, Alpha Innotech Corporation, USA) under ultra-violet light.

Double Stranded Deoxyribonucleic Acid Quantitation

DNA was quantified using a Nanodrop (Thermo Scientific, UK) spectrophotometer. Prior to analysis equipment was blanked using distilled water and then background readings were performed using the solution in which the DNA was dissolved (TE, EB or $H_2O$). Samples were tested in triplicate and data was interpreted using the ND-1000v 3.1.0 software according to the manufacturer's instructions. The final quantity of DNA was expressed as nanograms/microlitre.

Calcium Phosphate Transfection for Adenovirus Recovery

SwaI-linearised adenoviral plasmids containing either recombinant adenoviral genomic DNA or the wild-type adenovirus genome were transfected into HEK-293 cells using Lipofectamine 2000 transfection. HEK-293 cells were seeded in wells of a 6-well plate 24 h prior to transfection so that they were 70-80% confluent at the time of transfection.

For each well, lipofectamine 2000 suspended in 100 ul Opti-MEM Reduced Serum Media (Thermo Fisher Scientific) was mixed with DNA solution (2.5 µg in 100 µL Opti-MEM Reduced Serum Media) at a 1:2 ratio of total DNA mass to lipofectamine 2000 and incubated at room temperature before being added drop-wise to adherent HEK-293 which were growing in DMEM with 10% Fetal Bovine Serum (FBS) from Gibco® (Thermo Fisher Scientific UK).

The culture media containing the lipofectamine 2000 transfection complex was removed at 4 h post-transfection. Fresh DMEM media containing 2% FCS was added to each well. Cytopathic effects (CPE) were observed in wells containing successfully transfected cells between 12 and 15 days post-transfection. Virus stocks were serially 10-fold diluted into 96 well plates. Single clones were picked and amplified in 10 cm dishes from which infectious supernatants were collected and stored as seed stock for further amplification and virus production.

Virus Production and Purification by Banding on Caesium Chloride Gradients

Single virus clones were amplified in HEK-293 cells cultured in DMEM media containing 5% FCS, using approximately 15-25 confluent 175 cm$^2$ monolayers for each purification. HEK-293 monolayers containing virus-packed cells were harvested (72 hours post-infection, when CPE was observable but infected cells were not lysed) by gentle agitation and pelleted cells were re-suspended in infectious supernatant (16 mL, volume accommodated in three banding columns), then lysed by three freeze-thaw cycles to release virus particles. The mixture containing lysed cells and free virus particles was centrifuged at 245 g (10 min, 4° C.). The mixture was incubated on ice for 60 min, followed by centrifugation at 800 g (10 min, 4° C.). The pellet was discarded and the supernatant (containing virus particles) was loaded onto centrifuge tubes (Ultra-Clear™ Beckman Centrifuge tubes, Beckman Coulter UK Ltd) containing a caesium chloride (CsCl) gradient. The gradients were centrifuged (25,000 rpm, 10° C., 120 min without deceleration using a Beckman L8-70M Ultracentrifuge with rotor type SW40 TI) (Beckman Coulter, Inc, USA). Two discrete bands were obtained after centrifugation: a faint band higher in the column containing 'empty' viral particles, and a thicker, opaque lower band containing intact infectious viral particles. The virus was harvested by puncturing the tube below the level of the virus band with an 18-gauge needle and extracting the desired band into a syringe. CsCl was subsequently removed by consecutive dialyses in buffers (500 mL, 4° C.) containing 50 mM HEPES, 1×PBS, 0.1 g/L CaCl$_2$, 0.2 g/L (initial dialysis) or 0.1 g/L (final dialysis) MgCl$_2$ and 10% glycerol at pH 7.8, using a 3-15 mL dialysis cassette for the initial dialysis (Pierce Slide-A-Lyzer® Dialysis Cassette, Pierce Biotechnology, Inc., USA) after which the virus was recovered and treated with Benzonase DNA nuclease (6 µL/m L, Novagen, UK) for 30 minutes at room temperature. The virus was subsequently re-banded by CsCl gradient centrifugation and dialysed overnight in the final dialysis buffer using a 0.5-3 mL cassette (Pierce Slide-A-Lyzer® Dialysis Cassette, Pierce Biotechnology, Inc., USA). For each dialysis, the buffer was changed and replaced with fresh buffer after 1 hour and 2 hours, followed by an overnight dialysis. Virus obtained after the final dialysis was aliquoted and stored immediately at −80° C.

Double-Stranded DNA Measurement for Adenovirus Quantitation

Adenoviral DNA concentrations were determined using the PicoGreen assay (Quant-iT™ PicoGreen® dsDNA Reagent, Molecular Probes, Invitrogen). The assay contains a fluorescent nucleic acid probe for double-stranded DNA (dsDNA), allowing quantification of adenoviral genome content. Appropriate dilutions of virus stock solutions (10 to 100-fold) were made and were transferred (15 µL) to a solution containing 1×TE buffer (255 µL) and 0.5% sodium dodecyl sulphate (SDS) in 1×TE (30 µL). Samples were incubated at 56° C. (30 min) to disrupt virus particles. Six four-fold serial dilutions of known concentrations of the bacteriophage lambda DNA provided in the Quant-iT™ PicoGreen® Kit were carried out (highest concentration at 1 µg/mL), allowing the construction of a standard curve (last standard blank) from which the DNA content in unknown samples were calculated. The PicoGreen reagent was diluted 200-fold in 1×TE buffer. 100 µL of the diluted reagent was placed in wells of a black 96-well plate (Corning, UK) for each standard or unknown sample. 50 µL of appropriately diluted standards and samples were added to the wells in duplicate. The plate was read in a Wallac 1420 Victor2 multi-label counter, using the 'Fluorescein 485/535 nm, 1 second' program for analysis. The number of viral particles present in each sample was calculated on the basis that 1 µg of DNA is approximately equal to $2.7 \times 10^{10}$ adenoviral particles.

Calculation of Plaque Forming Units of Adenoviral Preparations Using the Tissue Culture Infectious Dose 50 (TCID50) Method The tissue culture infectious dose 50 (TCID50) method (Karber, 1931) was used to estimate the number of infectious virus particles, or plaque forming units (pfu), and is based on the development of cytopathic effects (CPE) in HEK-293 cells after infection with 10-fold serially diluted samples of virus preparation. This method is described in full in the manual for the AdEasy non-replicating virus platform available from QBiogene (France).

Adenovirus Preparations

All adenoviruses were grown in HEK-293 cells, purified by double banding in CsCl gradients as described above. Viral particle (vp) number was determined by measuring DNA content using a modified version of the PicoGreen assay (Invitrogen, Paisley, UK) (Mittereder et al. 1996). Infectivity was calculated using the TCID50 system with the KÄRBER statistical method (Karber, 1931) and was used to estimate the adenovirus titer (TCID50 units/mL) and corrected to determine plaque forming units/mL (pfu/mL).

Maintenance of Cell Lines

HEK293 human embryonic kidney cells were obtained from the European Collection of Cell Cultures (Porton Down, UK), and maintained in DMEM media with 10% FCS (PAA Laboratories, Yeovil, UK) including penicillin (25 U/mL) and streptomycin (10 mg/mL) at 37° C. in 5% CO$_2$ in a humidified incubator.

Real time (quantitative) PCR qPCR) for Ad5

The qPCR methodology for measurement of adenoviral particles has been previously described (Green et al., 2004). Briefly, viral DNA from infected cells or tissue samples was extracted using a mammalian genomic Genelute DNA extraction kit (Sigma). Reactions were performed using Applied Biosystems master mix following the manufacturer's protocol. The cycles were as follows: 94 degrees Celsius 10 min, then 40 times at 94° Celsius 30 s, 60° Celsius 1 min. Primers sequences for targeting Ad5 fiber were: Forward primer—5' TGG CTG TTA AAG GCA GTT TGG 3' (SEQ ID NO: 9) (Ad5 32350-32370 nucleotides) and reverse primer—5' GCA CTC CAT TTT CGT CAA ATC TT 3' (SEQ ID NO: 10) (Ad5 32433-32411 nt) and the TaqMan probe—5' TCC AAT ATC TGG AAC AGT TCA AAG TGC TCA TCT 3' (SEQ ID NO: 11) (Ad5 32372-32404 nt), dual labelled at the 5' end with 6-carboxyfluorescein and the 3' end with 6-carboxytetramethylrhodamine. The results were analyzed with the Sequence Detection System software (Applied Biosystems). Standard curves for tissues and cells were prepared by spiking samples of cell lysate or tissue homogenate with serial dilutions of known concentrations of virus particles followed by extraction and analysis of each sample separately by qPCR as described above.

Viral Genomic DNA Extraction

Where determination of adenoviral genome numbers was necessary, viral DNA was extracted from culture supernatants or cell lysates prepared in either lysis solution C (Sigma, UK) or lysis solution from the luciferase assay system (Promega, UK). Samples were treated with proteinase K (1 mg/mL) and incubated at 56 degrees Celsius for 20 minutes to degrade viral capsid proteins, followed by a 20 minute incubation at 70 degrees Celsius. Total cellular DNA extraction was then performed using the Genelute mammalian DNA extraction kit (Sigma-Aldrich, UK) according to the manufacturer's instructions.

Measuring MLP Activity by Luminometry

Cells were seeded in triplicate in 12 well plates. After 24 h plasmid DNA (0.5 μg) was added to 50 μL of HBS buffer and mixed with 2.5 μL DOTAP reagent (Roche) also in 50 μL sterile HBS. The complex was incubated at room temperature for 30 min. 100 μL of transfection mixture was added to each well and incubated at 37° C. for 4 h. Cells were washed with PBS and incubated with DMEM containing 2% fetal calf serum (FCS) (PAA Laboratories, Yeovil, UK). 24 h following transfection media was removed and 150 μL of reporter cell lysis buffer (Promega) was added to the cells. Cells were then frozen at −80° C. for 1 h before thawing. Luciferin (25 μL) (Promega, Southampton, UK) was added to 25 μL aliquots of cell lysate and relative luminescence was measured by luminometry (Lumat LB9507, Berthold Technologies, Redbourn, UK).

Virus Infections

Cells are cultured using the conditions described above, or conditions favourable for any such cell line, in which a transgene within the virus of the invention is to be expressed. Virus is added to the culture supernatant of the cells at an MOI from 1-1000, more preferably an MOI of 1-100 and more preferably still an MOI of 10-100.

Measuring Protein Expression

Transgene expression level or the level of expression of late proteins within a cell is measured via Western blot or an Enzyme-linked Immunosorbant Assay (ELISA). The method taken depends on whether the product being measured is intracellular or secreted outside of the cell. For the former, the level of protein is measured by lysing the cells to create a cell lysate followed by western blot or ELISA. For secreted material, the supernatant is analysed immediately by western blot or ELISA.

If a western blot protocol is used, the following approach is taken. 30 μg of protein is loaded onto a 10% polyacrylamide gel after quantitation using a QuantiPro BCA assay (Sigma Aldrich, cat: QPBCA-1KT). The gel is run at 160 V for 1 h and then protein is blotted onto to a nitrocellulose membrane overnight at 4 degrees Celsius at 30V. Nitrocellulose membrane is stained with Ponceau solution (described below) to confirm equal loading and transfer of samples and then blocked using 5% milk powder (Fluka, Sigma Aldrich) for 2 h (E1A) or overnight (Aldolase A). Membranes are then washed twice with PBS, 0.1% Tween 20, and then once with PBS. For detecting repression levels of adenovirus late proteins, an anti-Hexon western blot is used. A primary antibody recognising Hexon (AbCam, Cambridge, UK, cat number: Ab8249) is added at 1:500 dilution in 2.5% milk powder in PBS for 1 hr. Membrane is washed as above. Secondary anti-rabbit HRP labelled antibody is added at 1:1000 dilution in 2.5% milk powder for 1 h. The membranes are washed as above and then bathed in ECL western blotting detection reagent (Amersham, GE Healthcare) at 0.125 mL/cm$^2$ for 1 minute. Blot is visualised in an Alpha Innotech gel documentation system for 1, 5 and 10 minutes using chemi-luminescence detection. Molecular weights are calculated against a dual colour molecular weight ladder (Bio-Rad).

Ponceau Staining

To confirm successful transfer of protein from polyacrylamide gels onto nitrocellulose membranes and to ensure equal loading and transfer, membranes are stained for 2 minutes with Ponceau S solution (0.1% w/v Ponceau S in 5% v/v acetic acid made up with de-ionised distilled H$_2$O) prior to blocking. The stain is then poured off and membranes washed briefly in PBS twice before imaging. Membranes are then washed twice with PBS 0.1% Tween 20 and then once with PBS to remove all residual stain prior to blocking.

Rather than assessing protein levels by western blot, an ELISA may be used. To do this, a sample to be studied is first diluted in coating buffer (cat. 28382 Thermofisher). Typically, samples are coated onto the plates at different concentrations such as 1:10; 1:100; 1:500 to determine optimal detection range. A standard curve is created by using a pre-made quantity of the protein to be detected and coating wells the highest standard point of 4 μg/ml by dilution followed by 2-fold serial dilution into adjacent wells. For example, a standard protein at 0.2 mg/ml requires 4 μl with 196 μl of non-transfected culture media and 1.8 ml of coating buffer. This is used to generate an 8-point standard curve by performing 2-fold serial dilution by adding 1 ml of reconstituted standard and 1 ml of coating buffer in 1.5 ml tubes. 100 microliters of each standard is then added in duplicate to the ELISA plate. 100 microlitres of each sample is added to a well of the immuno-microplate. 100 microlitres of coating buffer is added to one well as a no-antigen control. 100 microlitres of a positive control sample is included, if available. The plate is incubated at 4 degrees Celsius overnight. The plate is washed with PBS-T (0.1% Tween) three times. 200 μL of blocking buffer is added (the original coating buffer with 2% BSA) per well and the plate is incubated at 37° C. for 1 hr. The plate is washed with PBS-T (0.1% tween) three times). The Primary antibody (1#) is added to the diluent solution at the required dilution and 50 μL is added to each well. The plate is incubated at room temperature for 1-2 hours. The plate is washed with PBS-T (0.1% tween) three times. A HRP-labelled secondary antibody is added to the diluent solution at the required dilution. 50 microlitres is added to each well. The plate is incubated at room temperature for 1 hour. The plate is washed with PBS-T (0.1% tween) three times. The plate is washed with PBS once. 50 microlitres of 3,3'5,5'-Tetramethylbenzidine (TMB) is added to each well. It is then necessary to wait for the colour to develop and to record the time taken. 50 microlitres of the stop solution (1 M HCl) is added. Data acquisition is achieved by reading the plates absorbance in a plate reader at 450 nm.

Measuring VLP Production

The levels of VLP production from a cell Transgene expression level or the level of expression of late proteins are measured via Western blot or ELISA as described above but using antibodies recognising an epitope on the VLP surface.

Figure 4:
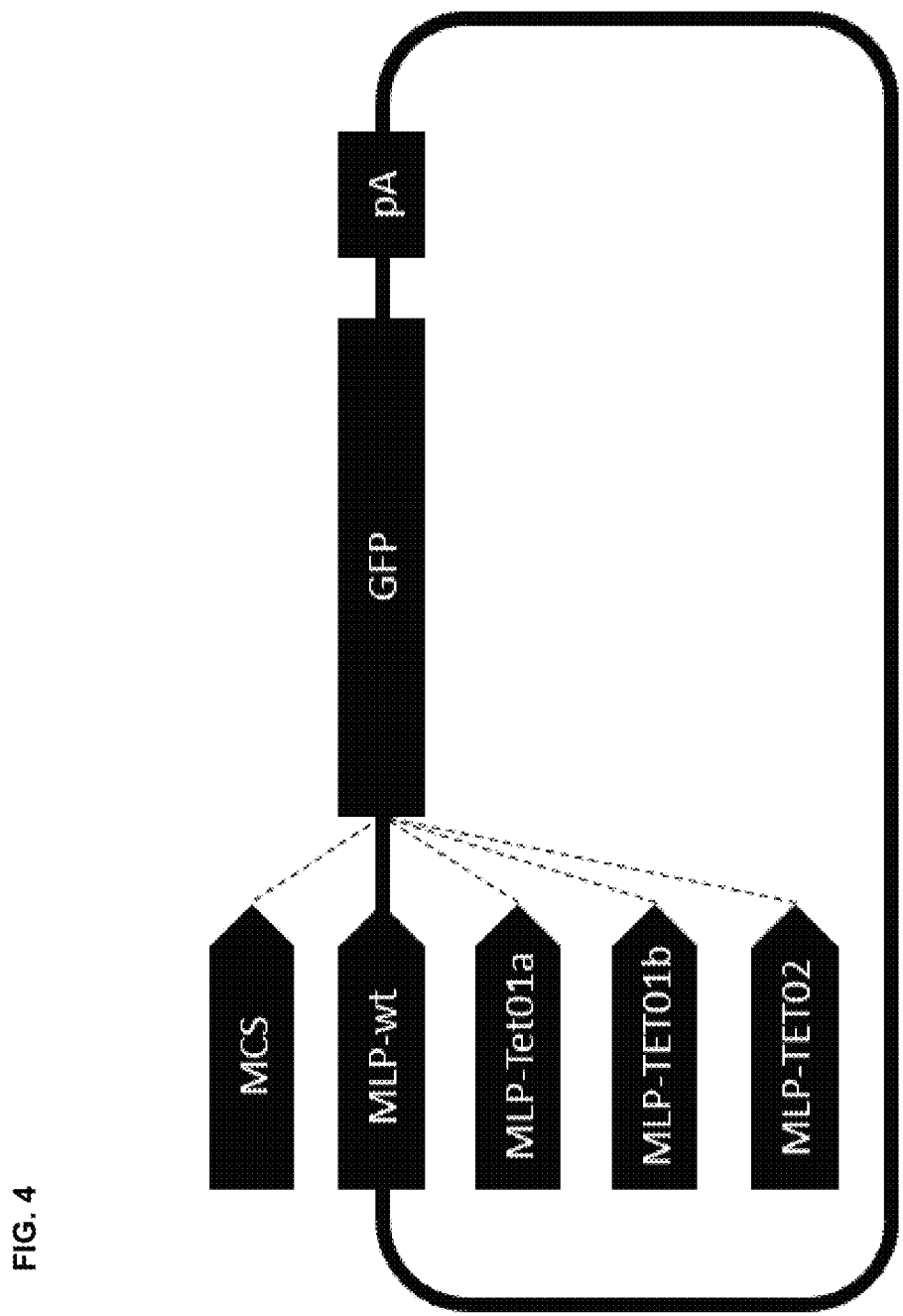
FIG. 4 shows schematic diagrams of plasmid vectors constructed for expression of the GFP reporter from the Ad5 repressor mutant Major late promoters.

Example 1: Construction of Plasmid Vectors for Expression of the GFP Reporter from the Ad5 Repressor Mutant Major Late Promoters Five expression constructs were created wherein the GFP reporter gene was transcribed by the wildtype Ad5 MLP (pMLPwt-GFP), repressor mutant MLPs (pMLP-TET01a-GFP; pMLP-TET01b-GFP; pMLP-TET02-GFP) or the control construct in which no internal promoter was present (pMCS-GFP) for determining low level baseline transcription. The vectors are shown in FIG. 4.

Example 2: Expression of the GFP Reporter Gene from MLP Promoters

Figure 5:
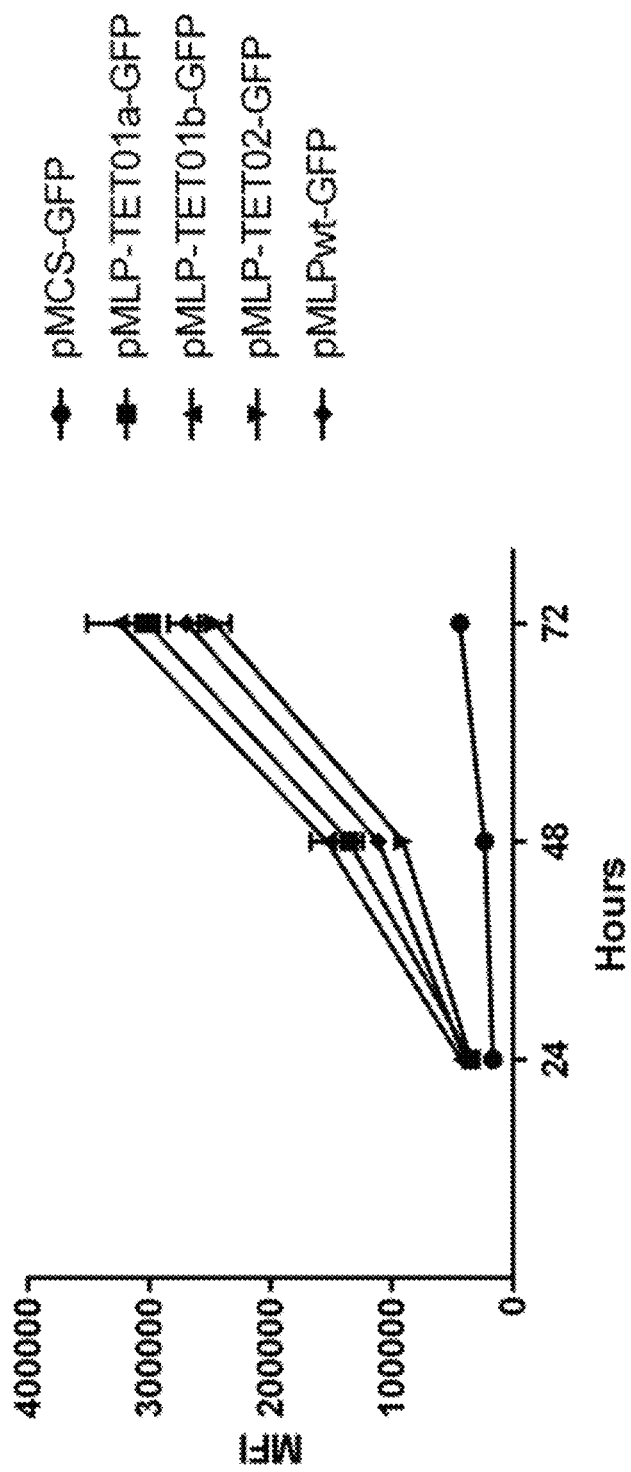
FIG. 5 shows plasmid vectors expressing the GFP reporter gene from MLP promoters.

Five expression constructs were created wherein the GFP reporter gene was transcribed by the wildtype Ad5 MLP (pMLPwt-GFP), repressor mutant MLPs (pMLP-TET01a-GFP; pMLP-TET01b-GFP; pMLP-TET02-GFP) or the control construct in which no internal promoter was present (pMCS-GFP) for determining low level baseline transcription. HEK293 cells were seeded in tissue culture treated 48-well plates at a density of 3e4 cells/well, 24-hours before transfection. HEK293 cells were transfected with the plasmids pMLPwt-GFP; pMLP-TET01a-GFP; pMLP-TET01b-GFP; pMLP-TET02-GFP; pMCS-GFP using branched PEI (25 kDA) at a 1:3 ratio of total DNA mass to PEI. Transfection was carried out in triplicates and cells were harvested at 24 hours, 48 hours and 72 hours post transfection for analysis by flow cytometry. Data is presented in FIG. 5 as MFI (mean fluorescent intensity) of GFP positive cells. Error bars indicate SD of triple biological replicates. Data NS p>0.05 by Student's t-test.

Figure 6:
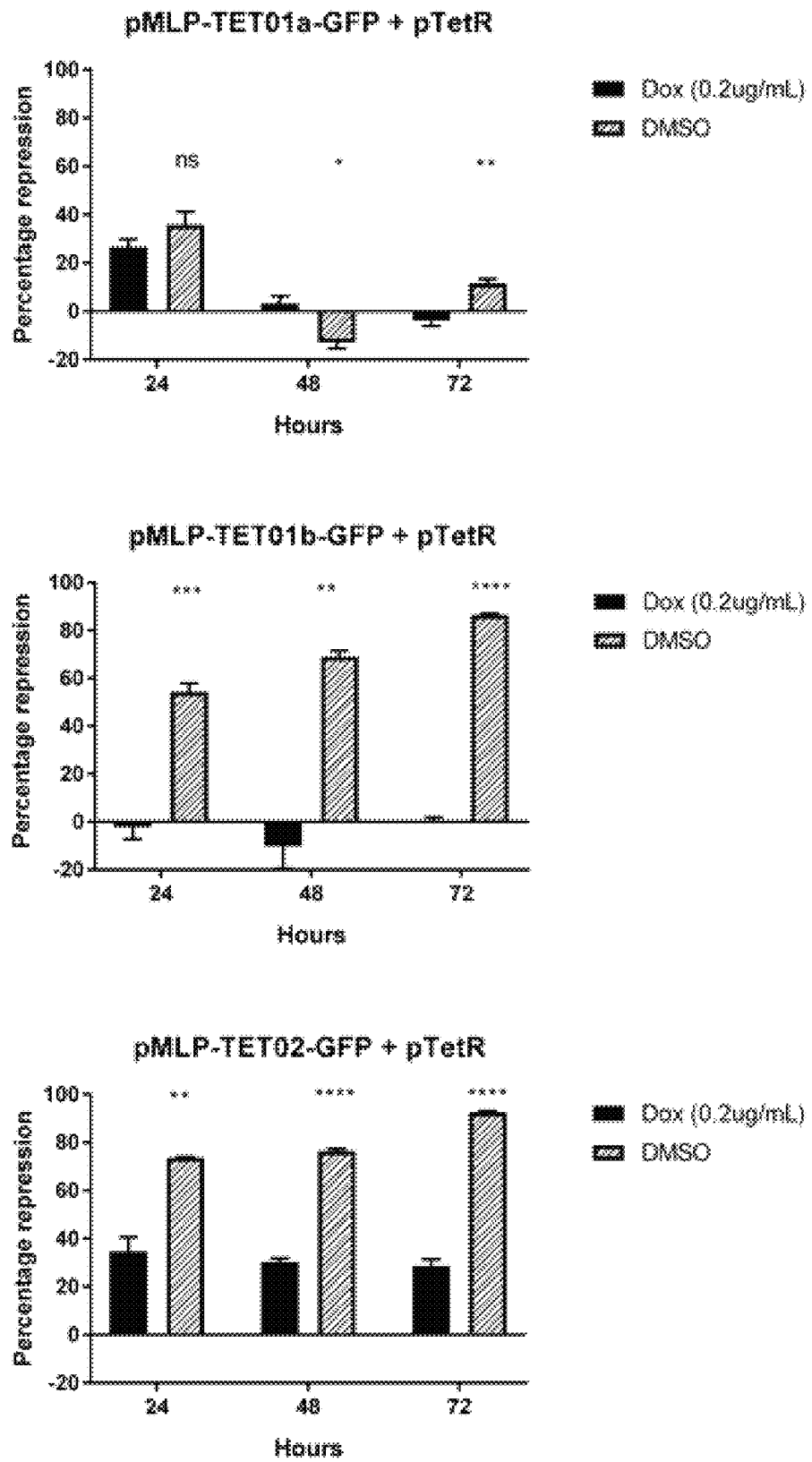
FIG. 6 shows transcriptional repression of the repressor mutant MLP by the TETR protein.

Example 3: Transcriptional Repression of the Repressor Mutant MLP by the TETR Protein Five expression constructs were created wherein the GFP reporter gene was transcribed by the wildtype Ad5 MLP (pMLPwt-GFP), repressor mutant MLP (pMLP-TET01a-GFP; pMLP-TET01b-GFP; pMLP-TET02-GFP) or the control construct in which no internal promoter was present (pMCS-GFP) for determining low level baseline transcription. Wildtype Ad5 MLP (pMLPwt-GFP), repressor mutant MLP (pMLP-TET01a-GFP; pMLP-TET01b-GFP; pMLP-TET02-GFP) or the control construct expressing the GFP reporter was co-transfected with a TETR expression plasmid (pTETR), under the control of the constitutive CMV (cytomegalovirus) promoter, at a 1:1 ratio of total DNA mass, in HEK293 cells treated with doxycycline 0.2 µg/ml or DMSO. HEK293 cells were seeded in tissue culture treated 48-well plates at a density of 3e4 cells/well, 24-hours before transfection. Transfection was carried out in triplicates using branched PEI (25 kDA) at a 1:3 ratio of total DNA mass to PEI and cells were analysed by flow cytometry at 24, 48 and 72 hours post transfection. Data is presented in FIG. 6 as percentage repression of MFI (mean fluorescent intensity) in GFP positive cells compared against the activity of the Ad5 MLP wildtype (pMLPwt-GFP) and normalised against the promoterless control construct for background expression signal. Data as mean±SD NS p>0.05; *p≤0.05; p≤0.01; *p≤0.001; ****P≤0.0001; unpaired, two tailed Student's.

Example 4: Ad5 MLP Repressor in Repression in HEK293 T-Rex Flp Cells

Figure 7:
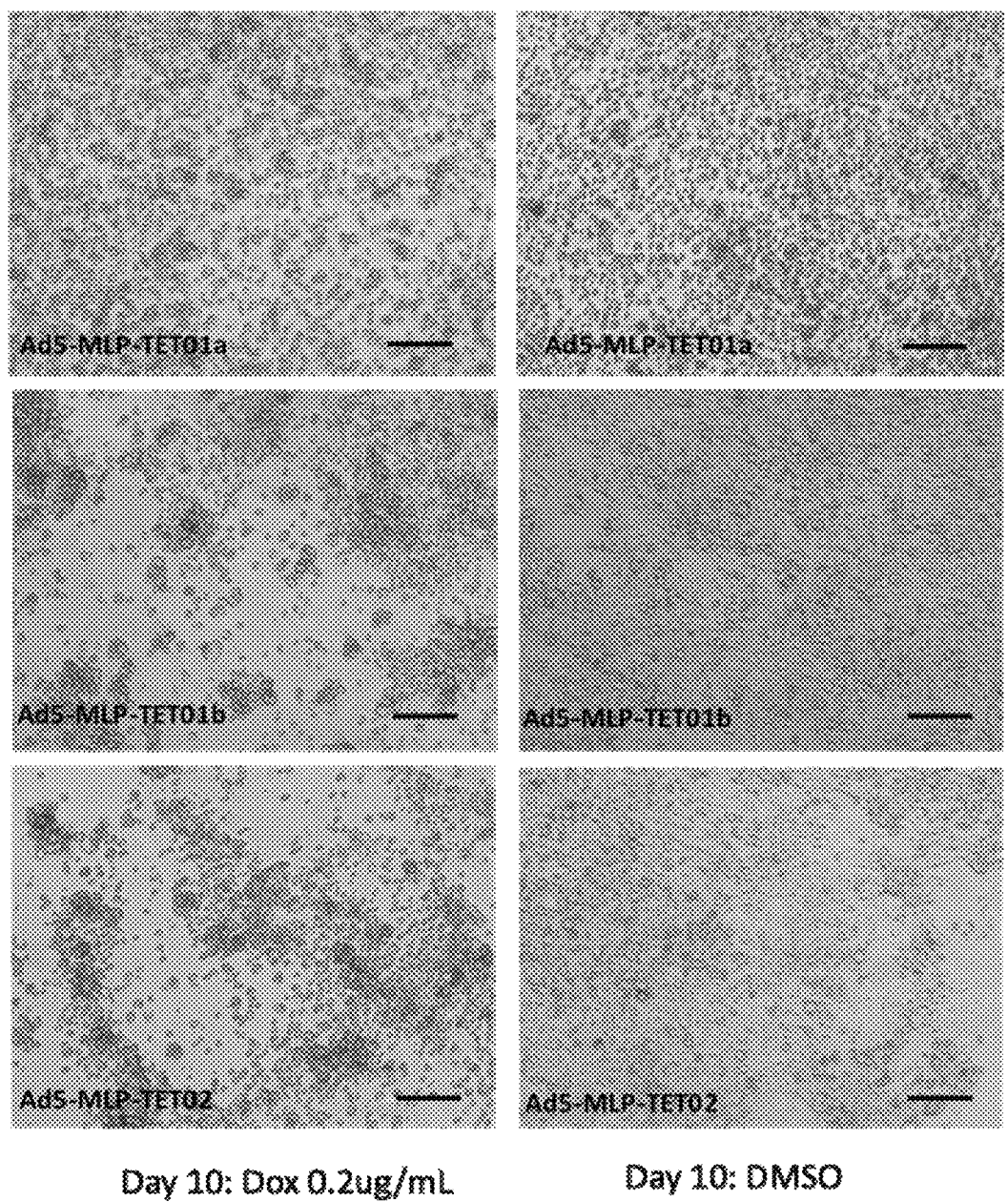
FIG. 7 shows examples of MLP repressor Ad5 in repression in HEK293 T-Rex Flp cells, a cell line stably expressing the TETR protein.

Adenoviruses engineered by molecular cloning methods to incorporate the repressor sequences were recovered in HEK293 cells. Ad5 genome with the MLP repressor sequence MLP-TET01a, MLP-TET01b, TET02 or wildtype MLP were excised away from bacterial plasmid DNA by restriction digest with SwaI restriction enzymes to release the 5' and 3' flanking Ad5 ITR sequences. HEK293 cells were seeded in 10-cm tissue culture plates at a density of 1e5 cells/plate for 24-hours and transfected with 10 µg of DNA containing MLP repressor Ad5 or Ad5 MLPwt genomes, using lipofectamine 2000 at a 1:2 ratio of total DNA mass to lipofectamine 2000. Viruses were harvested following observation of viral infection and cytoplasmic effect, typically, 10-15 days post transfection. 293 T-Rex Flp cells were seeded in 48-well tissue culture treated plates at a density of 4e4 cells/well for 24-hours and transduced with adenoviruses Ad5-MLP-TET01a, Ad5-MLP-TET01b, Ad5-MLP-TET02 or standard E1-E3 deleted Ad5 (Ad5-MLPwt) in the presence of doxycycline 0.2 µg/ml or DMSO and imaged by light miscopy 10-days post infection. Data shown in FIG. 7 is representative of triplicate biological replicates. Bar=250 µm.

Figure 8:
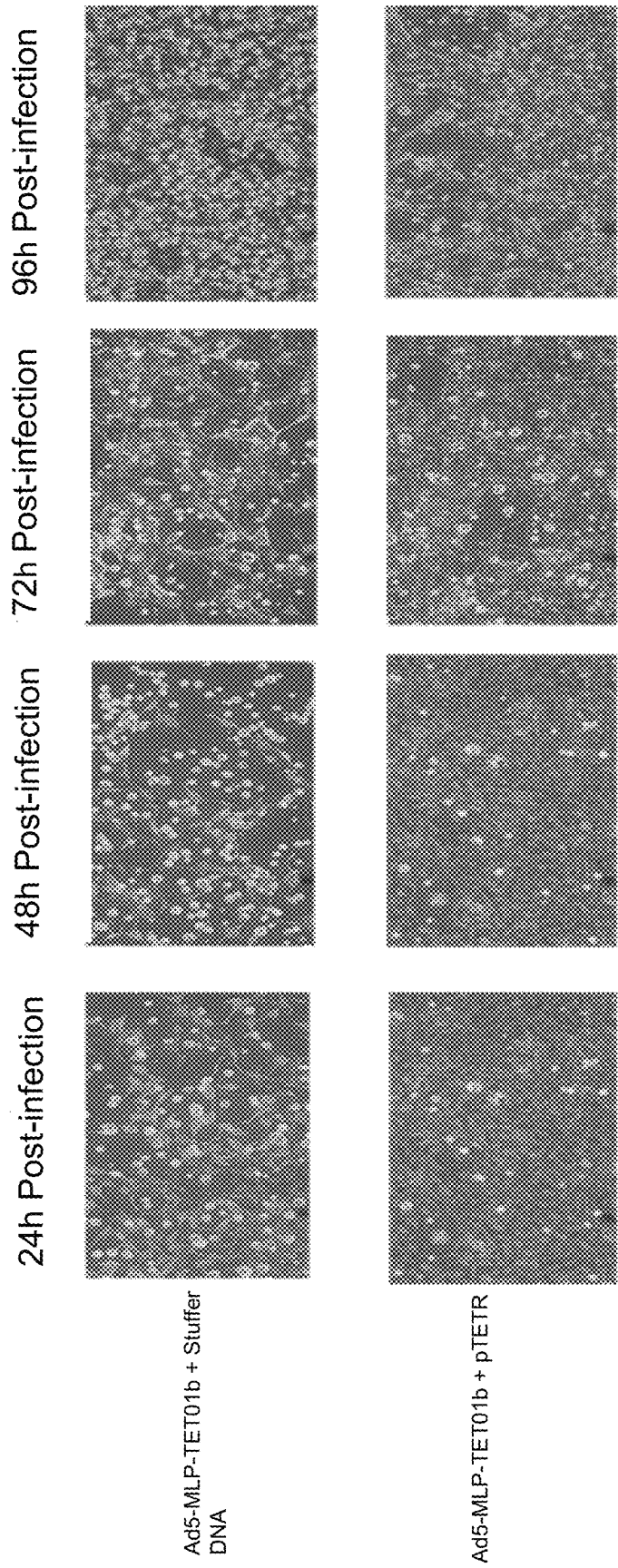
FIG. 8 shows examples of MLP repressor Ad5 in repression in 293Ad cells transfected with a TETR expression plasmid (pTETR), under the control of the constitutive CMV (cytomegalovirus) promoter.

Example 5: Ad5 MLP Repressor in Repression in 293Ad Cells Transfected with a TETR Expression Plasmid (pTETR), Under the Control of the Constitutive CMV (Cytomegalovirus) Promoter Adenoviruses engineered by molecular cloning methods to incorporate the repressor sequences MLP-TET01b were recovered in HEK293 cells. Ad5 genome with the MLP repressor sequence MLP-TET01b were excised away from bacterial plasmid DNA by restriction digest with SwaI restriction enzymes to release the 5' and 3' flanking Ad5 ITR sequences. HEK293 cells were seeded in 10-cm tissue culture plates at a density of 1e5 cells/plate for 24-hours and transfected with bug of DNA containing MLP repressor Ad5, using lipofectamine 2000 at a 1:2 ratio of total DNA mass to lipofectamine 2000. Viruses were harvested following observation of viral infection and cytoplasmic effect, typically, 10-15 days post transfection. HEK293 cells were seeded in 10-cm tissue culture plates were transfected with pTETR (5 µg) or stuffer DNA, using lipofectamine 2000 at a 1:2 ratio of total DNA mass to lipofectamine 2000, prior to infection with adenoviruses Ad5-MLP-TET01b. The results are shown in FIG. 8. Data imaged by light microscopy 24, 48, 72 and 96 hours post-infection.

Figure 9:
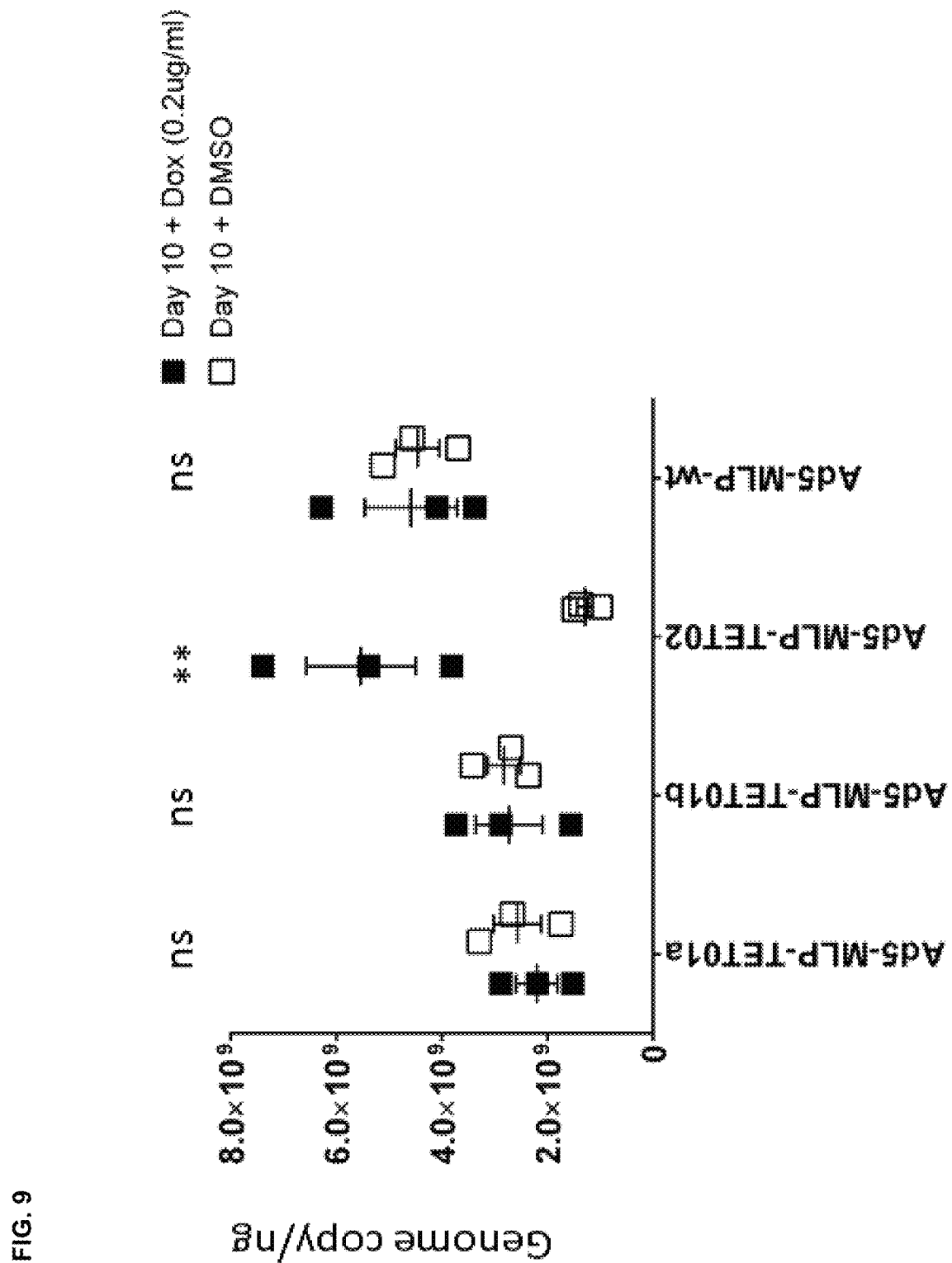
FIG. 9 shows viral genome replication of repressed MLP mutant Ad5 in 293 T-Rex Flp cells, a cell line stably expressing the TETR protein.

Example 6: Viral Genome Replication of Repressed MLP Mutant Ad5 in 293 T-Rex Flp cells Adenoviruses engineered by molecular cloning methods to incorporate the repressor sequences were recovered in HEK293 cells. Ad5 genome with the MLP repressor sequence MLP-TET01a, MLP-TET01b, TET02 or wildtype MLP were excised away from bacterial plasmid DNA by restriction digest with SwaI restriction enzymes to release the 5' and 3' flanking Ad5 ITR sequences. 293 T-Rex Flp cells were seeded in 10-cm tissue culture plates at a density of 1e5 cells/plate for 24-hours and transfected with 10 µg of DNA containing MLP repressor Ad5 or Ad5 MLPwt genomes, using lipofectamine 2000 at a 1:2 ratio of total DNA mass to lipofectamine 2000. Viruses were harvested following observation of viral infection and cytoplasmic effect, typically 10-15 days post transfection. 293 T-Rex Flp cells were seeded in 48-well tissue culture treated plates at a density of 4e4 cells/well for 24-hours and transduced with adenoviruses Ad5-MLP-TET01a, Ad5-MLP-TET01b, Ad5-MLP-TET02 or standard E1-E3 deleted Ad5 (Ad5-MLPwt)

in the presence of doxycycline 0.2 µg/ml or DMSO 293 T-Rex Flp cells were infected with MLP mutant or MLP-wt Ad5 in the presence of doxycycline or DMSO. Total viral and cellular DNA was harvested 10-days post infection. Viral genome copy was quantified by qPCR using TaqMan® probes. Ad5 of known titres were used for generating the standard curve and data is presented (FIG. 9) as increase in genome copy above the initial viral load used for infection. Data representative of triplicate biological replicates and presented as mean±SEM **P≤0.01; unpaired, two tailed Student's.

Example 7: MLP Repression Blocks Adenovirus Spread Across HEK293 Cell Monolayer

Figure 10A:
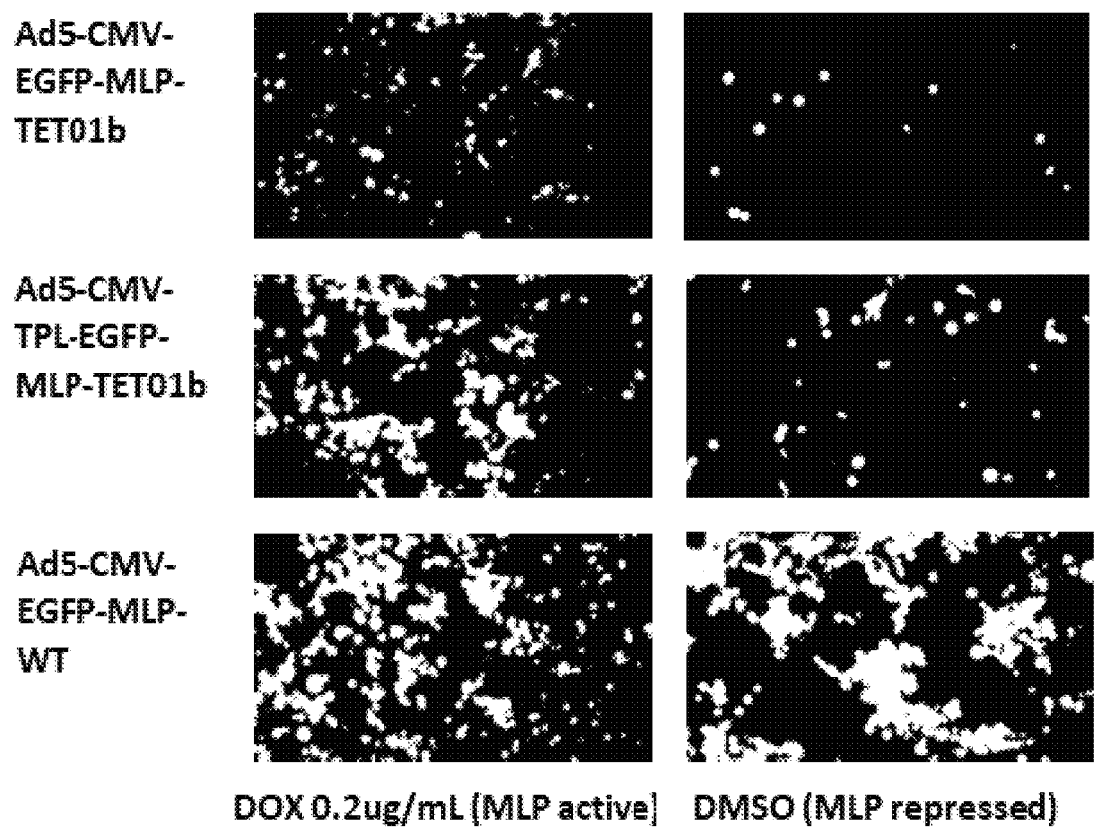
FIGS. 10A and B show Ad5 with TET1b modified MLP variants infection of HEK293 cells at low MOI.

To determine the effect of MLP repression on inhibiting adenovirus production and virus spreading, adenovirus with wild-type MLP or TET01b modification was engineered to express the EGFP reporter, with and without Ad5 TPL fused to the EGFP initiation codon. EGFP reporter was expressed from the virus E1 deleted region and under control of the CMV promoter. Adenoviruses expressing EGFP were used to infect a monolayer of Flp-In T-REx 293 cells treated with doxycycline or DMSO at MOI 1 and EGFP expression was monitored at 6-days by fluorescence microscopy and flow cytometry. While viral spreading i.e EGFP expression across the cell monolayer was not inhibited in the control adenovirus with wild-type MLP, virus spreading of adenoviruses with MLP TET01b was blocked in Flp-In T-REx 293 cells in the absence of doxycycline, indicating repression of virion replication (FIG. 10A).

Figure 10B:
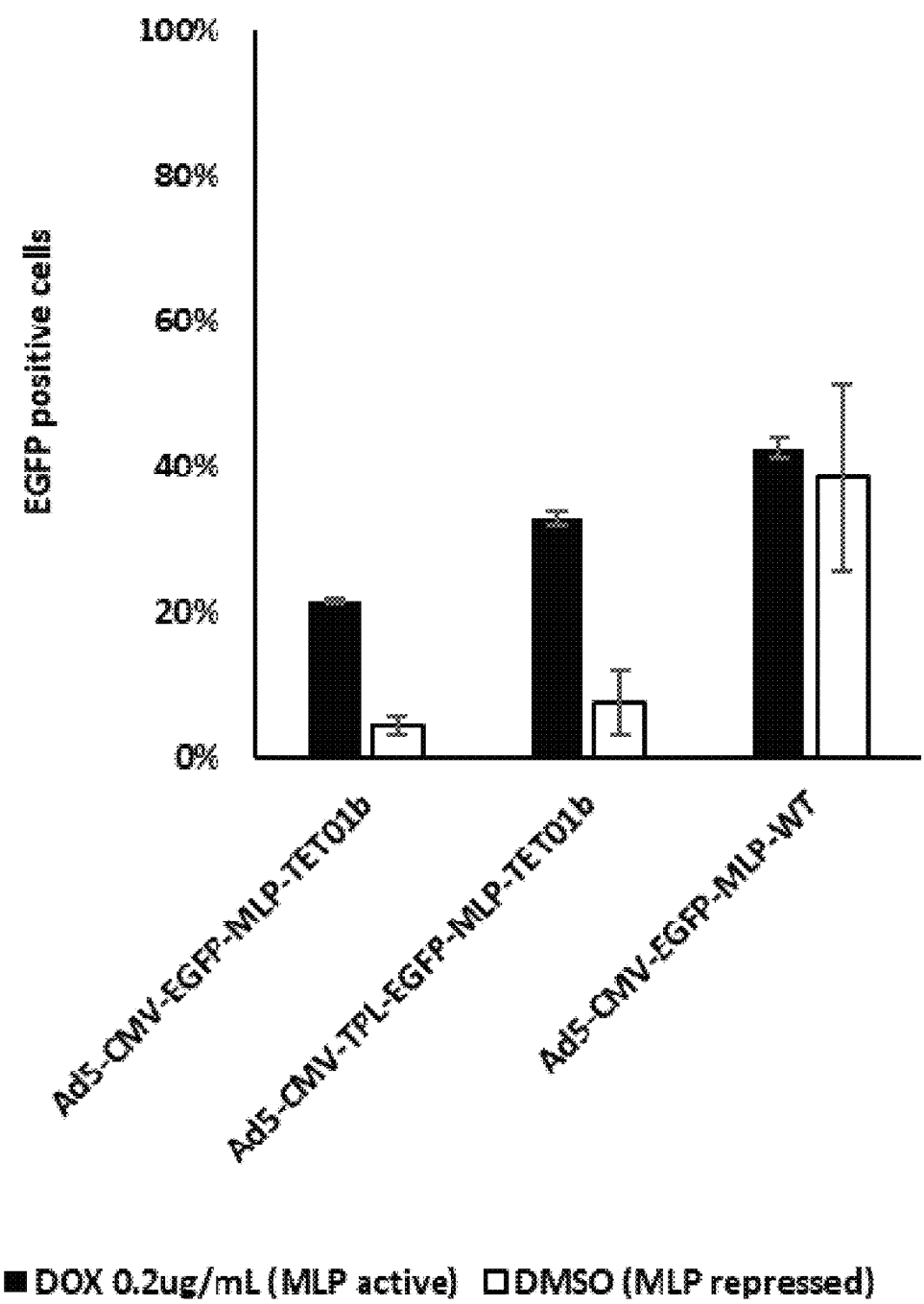

Following 6-days post infection, cells were harvested for flow cytometry to determine the relative proportion of EGFP expressing cells within the gated population. In line with results from fluorescent microscopy, the proportion of cells expressing EGFP was comparable in Flp-In T-REX 293 cells treated with doxycycline or DMSO following infection with the control adenovirus (FIG. 10B). However, whilst the population of EGFP positive cells were lower from infection with MLP TET01b modified adenoviruses in cells treated with doxycycline compared to the control virus, presumably due to variation in infectivity and replication, cells treated with DMSO showed a significantly lower population of EGFP expressing cells, indicating that EGFP is only expressed from cells transduced by viruses from the first-round infection.

Example 8: MLP Repression Enhanced Expression of EGFP Containing Ad5 TPL Exon 1-2-3

Figure 11B:
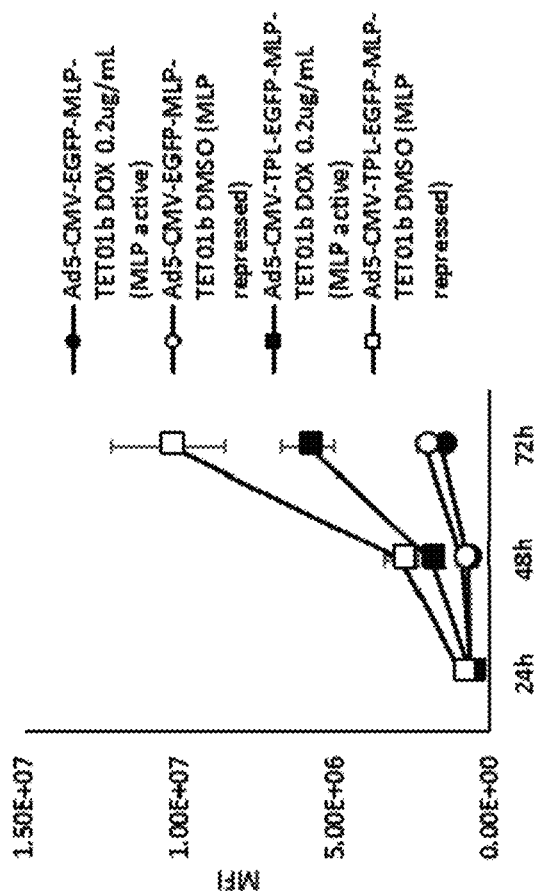
FIGS. 11A to 11D show EGFP expression from Ad5 with TET01b modified MLP.
Figure 11A:
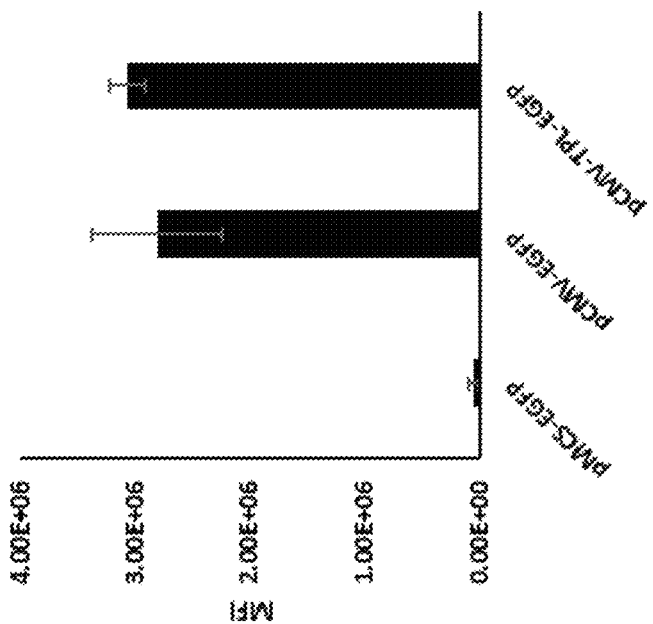

To determine whether fusion of Ad5 TPL exons to the initiation codon of EGFP affected gene expression, plasmids engineered to express EGFP, with and without the leader sequence, under the control of the CMV promoter were transfected into HEK293 cells and EGFP expression determined by flow cytometry at 48 hours post-transfection. The results are shown in FIG. 11A. Whilst the promoter-less control plasmid showed background levels of EGFP, there were no significant differences in the levels of EGFP expression from plasmid containing the TPL sequence.

To assess whether protein expression is increased following MLP repression, MLP TET01b modified adenoviruses expressing the EGFP reporter from the CMV promoter, with and without Ad5 TPL, were infected into Flp-In T-REx 293 cells treated with doxycycline or DMSO at an MOI 10, and EGFP expression was measured by flow cytometry 24, 48 and 72-hours post-infection. The results are shown in FIG. 11B. While MLP TET01b adenovirus expressing EGFP containing the TPL showed an increase in median fluorescence intensity (MFI) compared to EGFP lacking the TPL sequence, repression of the adenovirus MLP from infection in the DMSO treated cells resulted in a further ~2-fold increase in EGFP expression compared to virus infection into cells treated with doxycycline, which enables virion production.

Figure 11C:
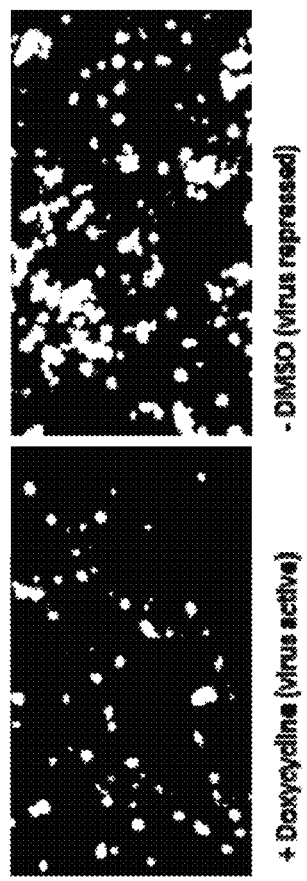
Figure 11D:
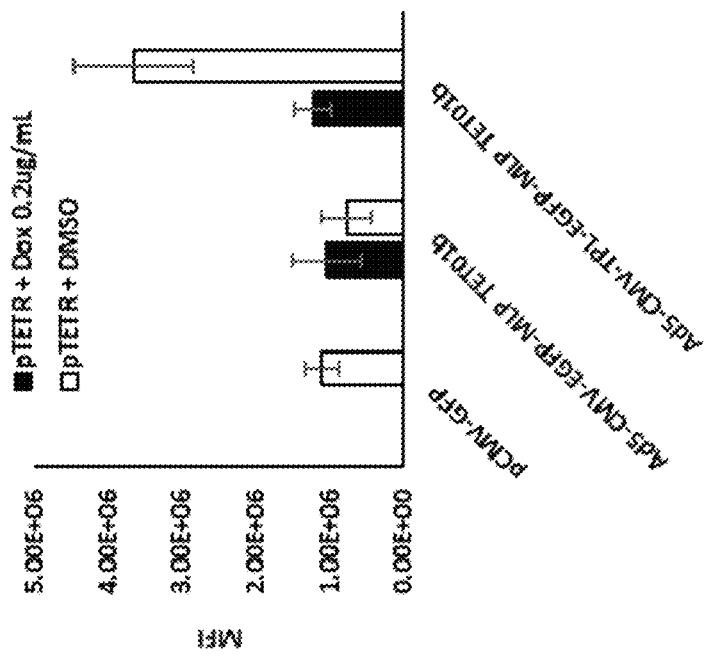

Similarly, a ~3-fold increase in EGFP expression was observed in HEK293 cells when adenovirus MLP was repressed by transient expression of the repressor TETR (see FIGS. 11C and 11D). Plasmid expressing TETR from the CMV promoter was transfected into HEK293 cells treated with doxycycline or DMSO. Subsequently, cells were infected with adenovirus containing MLP TET01b modification and expressing EGFP (with and without the TPL exons) from the CMV promoter or transfected using Lipofectamine with a CMV expression plasmid that transcribed EGFP. EGFP expression was determined by flow cytometry 48-hours post transduction with the virus and plasmid. results showed comparable levels of EGFP expression, as determined by MFI, from HEK293 cells transduced with the EGFP expressing adenoviruses or plasmid DNA. However, ~3-fold increase in EGFP expression was only observed from infection with the MLP TET01b modified adenovirus expression EGFP with the TPL exons in cells treated with DMSO, which allowed repression of Ad MLP TET01b by TETR, indicating enhance protein production by cap-independent translation as this effect was not observed in the EGFP coding sequence without the TPL exons.

Figure 12A:
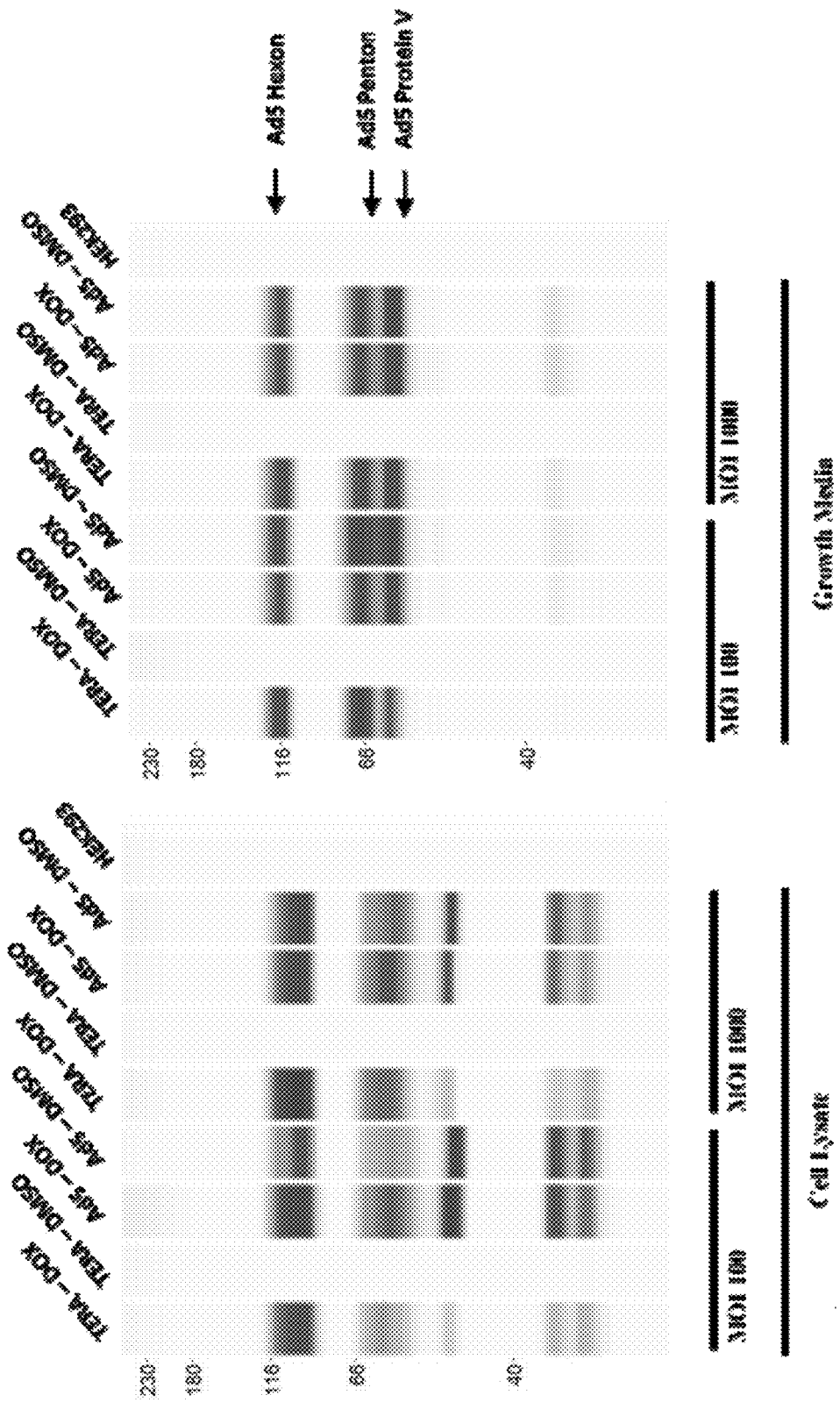
FIGS. 12A to 12C show Western blot detection of adenovirus structural proteins from TERA-CMV-EGFP or E1/E3 Ad5-CMV-EGFP infection in HEK293 cells.
Figure 12B:
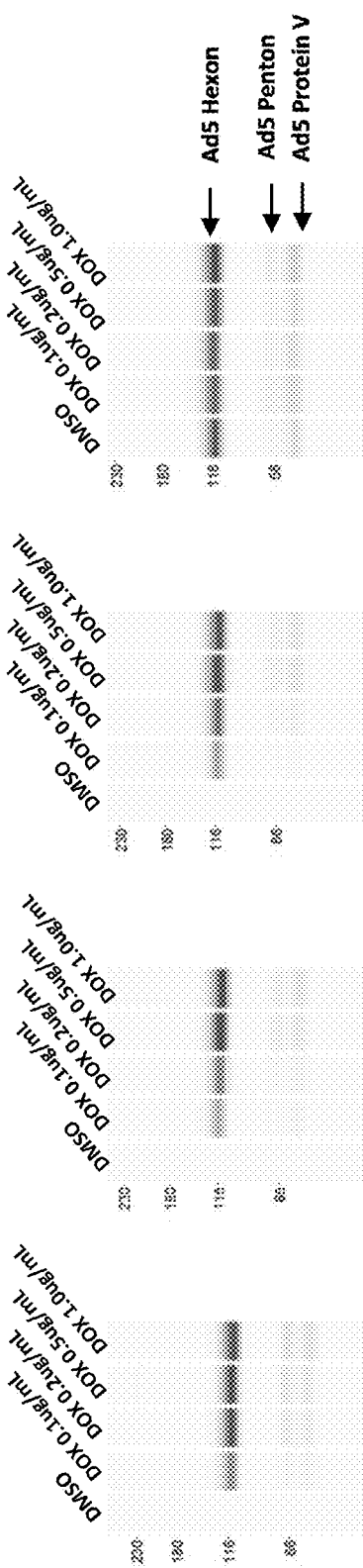
Figure 12C:
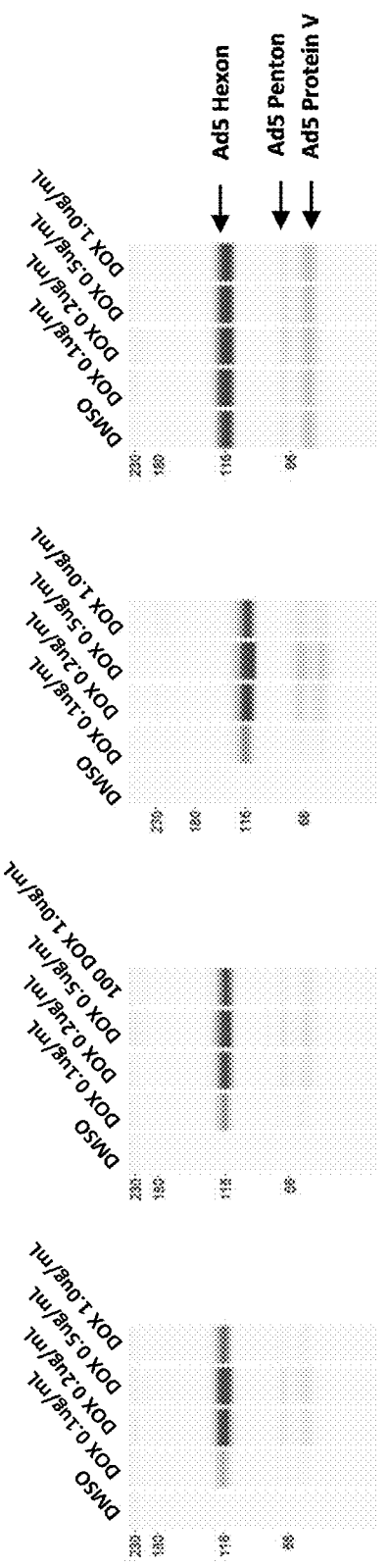

Example 9: MLP Self-Repression by Tetracycline-Enabled Repression Adenovirus (TERA) Inhibits Production of Adenoviral Structural Proteins Adenoviruses with MLP TET01b modification was further engineered to express the repressor TETR from a splice acceptor sequence under direct control of the virus internal MLP, position at the E3-deleted region of the virus, to construct TERA. The results are shown in FIGS. 12A to 12C.

To assess repression of viral structural proteins from TERA, control adenovirus E1/E3 deleted or TERA was used for infection of HEK293 cells in the presence of doxycycline or DMSO, at an MOI 100 or 1000. Adenovirus capsid proteins from cellular lysate and growth medium were probed using anti-Ad5 antibodies by Western blot 72-hours post infection. Comparable levels of adenovirus structural proteins were detected from TERA and the control virus when doxycycline was present in the growth medium, from both cell lysates and culture media. However, in the treated DMSO group, structural proteins from TERA were undetectable from the blot. Presumably, in the absence of doxycycline, TERA infection into HEK293 cells enabled production of viral MLP transcribed TETR to self-repression of its own MLP and blockade in the production of capsid proteins.

In a doxycycline dose-escalation study to assess production of TERA in HEK293 cells, control adenovirus with the wildtype MLP or TERA was used for infection of HEK293 cells at MOI 10 and 100, treated with DMSO or doxycycline dose of 0.1, 0.2, 0.5 and 1.0 µg/mL. The results are shown in FIGS. 12B and 12C. Comparable levels of Ad5 major structural proteins were detected for the control adenovirus infection in cells treated with DMSO or doxycycline, while capsid proteins expressed from TERA increased with increasing doses of doxycycline up to 0.5 μg/mL, consistent for both MOI assessed.

Figure 13B:
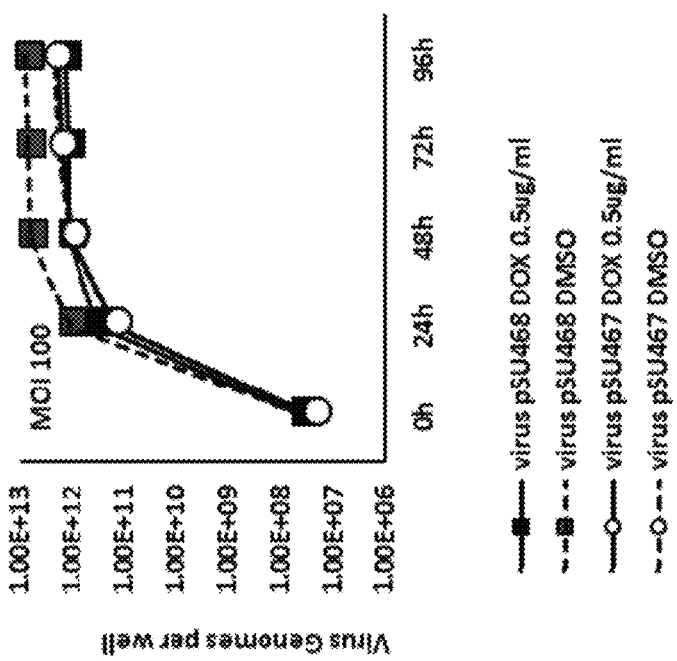
FIGS. 13A and 13B show DNA and virus replication of TERA in HEK293 cells.
Figure 13A:
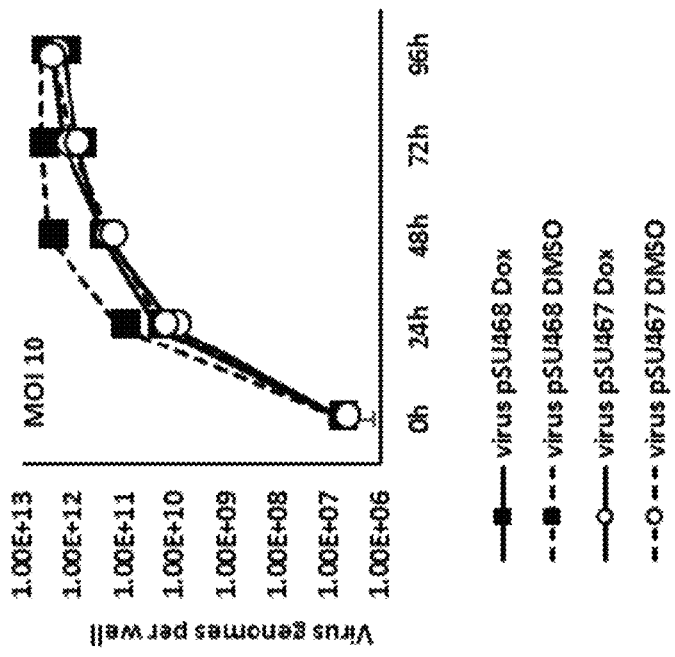

Example 10: TERA Viral Replication is Comparable to E1/E3 Deleted Adenovirus and MLP Repression Enhanced DNA Replication To assess virus replication of TERA, control E1/E3 deleted adenovirus or TERA was used to infect a monolayer of HEK293 cells at MOI 1, 10 and 100, in the presence of doxycycline, and total genomic DNA was extracted from growth media and cellular lysate at time-point 0, 24, 48 and 72-hours post viral infection. Abundance of adenovirus genomic DNA was determined by qPCR. The results are shown in FIGS. 13A and 13B.

For all three infection MOI assessed, virus replication of TERA was comparable to the control adenovirus, where the relative abundance of viral genome increased sharply at 24 h, with >4-log increases in total viral genomes at 72 h post-infection.

Genome replication of TERA during MLP repression was further assessed by qPCR. The virus TERA or control E1/E3 deleted adenovirus was used for infecting HEK293 cells in the presence of doxycycline or DMSO at an MOI of 10 and 100 and total genomic DNA was harvested at time-point 0, 24, 48, 72, and 96-hours post infection viral genome quantification by qPCR. Similarly, while virus replication of TERA was comparable to the control virus, DNA replication from TERA significantly increased after 24-hours post infection in HEK293 cells treated with the DMSO control group compared to infection into cells cultured with doxycycline. Presumably, repression of the virus MLP inhibited TERA from completion of its replicative life-cycle, thereby enabling exponential viral genome amplification.

Example 11: TERA Enhanced Expression of the EGFP Reporter

Figures 14A, 14B:
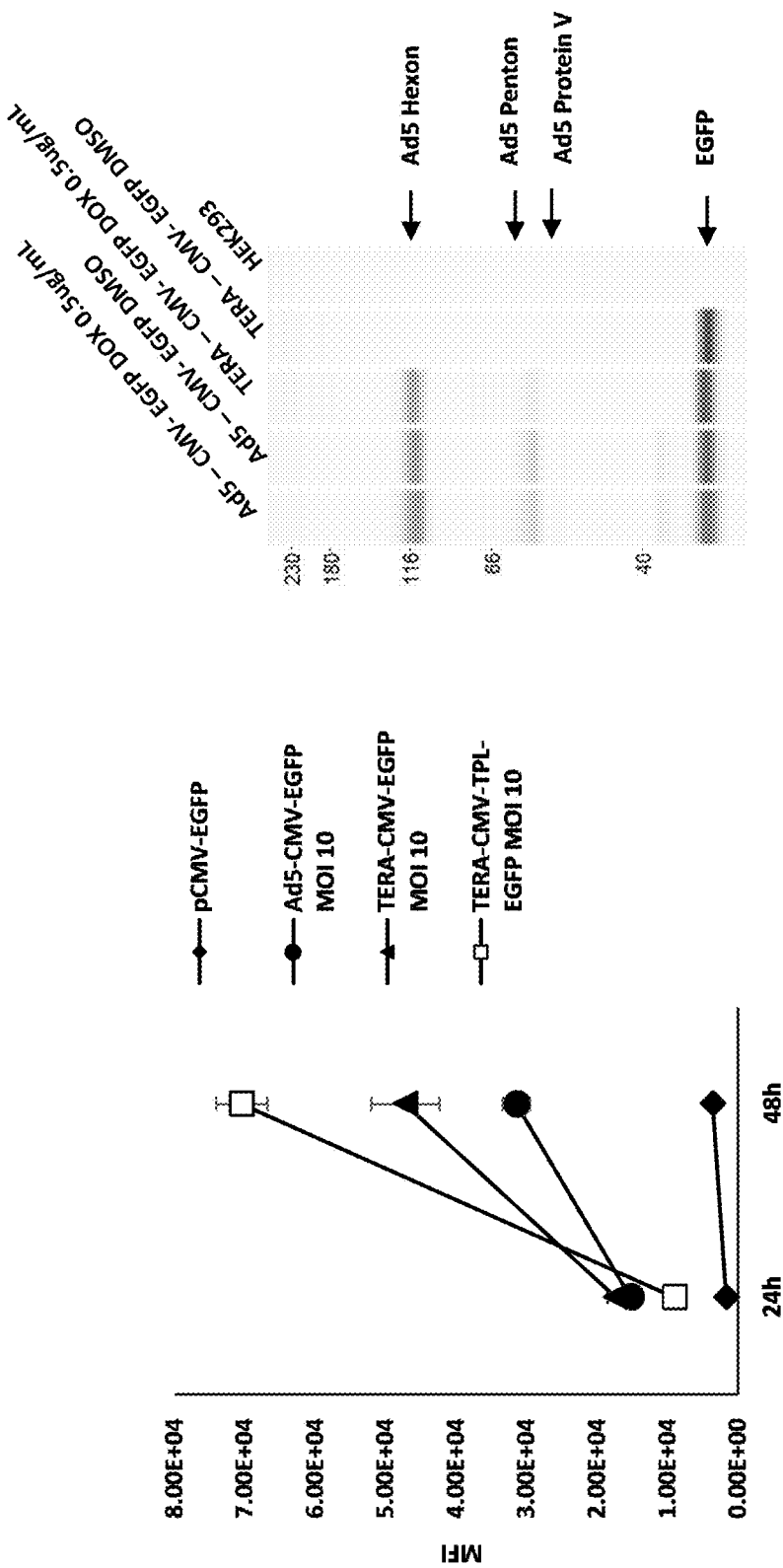
FIGS. 14A and 14B show reporter EGFP expression from TERA in HEK293 cells.

To assess EGFP reporter expression from TERA under control of the CMV promoter, TERA engineered to express EGFP, with and without the Ad5 TPL exons, were used to infect HEK293 cells and EGFP expression is compared to expression from E1/E3 control adenovirus and method of transient transfection with a CMV expression plasmid. The results are shown in FIGS. 14A and 14B.

While E1/E3 adenovirus and TERA exhibited increase EGFP expression compared to expression from a CMV plasmid vector, TERA expressing EGFP containing Ad5 TPL exons enhanced production above levels observed from both E1/E3 control vector and TERA without the TPL exons. Presumably, self-repression of TERA MLP by the virally encoded TETR resulted in repression of Ad5 late mRNA transcripts and enabling cap-independent translation of the prevailing TPL EGFP mRNAs.

Additionally, Western blot confirmed that EGFP expression using the control E1/E3 adenovirus and TERA, in the presence of doxycycline, was accompanied with contaminating adenovirus proteins. In contrast, the absence of doxycycline enabled repression of Ad5 structural proteins in TERA while EGFP expression was maintained.

Example 12: TERA Enhanced Production of a Bi-Specific T-Cell Engager (BiTE)

Figures 15A, 15B, 15C:
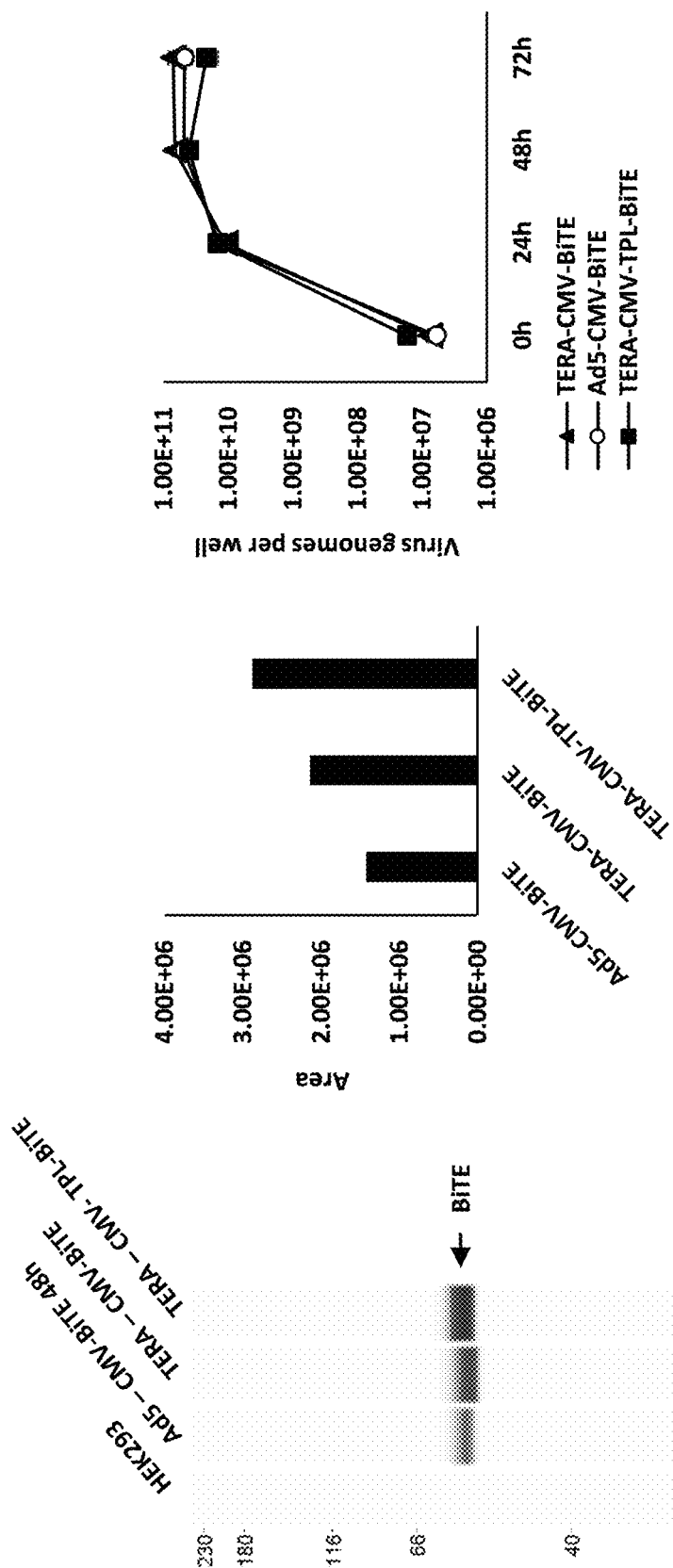
FIGS. 15A to 15E show TERA expression of BiTE® protein in HEK293 cells.

To compare production of a model secretory protein using TERA against a method of transient expression from plasmid DNA, TERA and plasmid vector (pCMV-BiTE) were engineered to express a Bi-Specific T-Cell Engager (BiTE) against tumour specific antigen EpCAM under the control of the CMV promoter. The results are shown in FIG. 15, parts A-E.

Virus TERA expressing BiTE® protein containing the Ad5 TPL exons or plasmid pCMV-BITE® protein was used to transduce HEK293 cells at MOI 10 or 0.75 μg DNA per well, respectively, and protein harvested from growth media at time-point 24, 48 and 72-hours post-transduction and probed using anti-6x His antibodies. Western blot showed significant increase in BiTE® protein expressing from TERA compared to production from using the CMV expression plasmid in all three time-point of harvest.

Figures 15D, 15E:
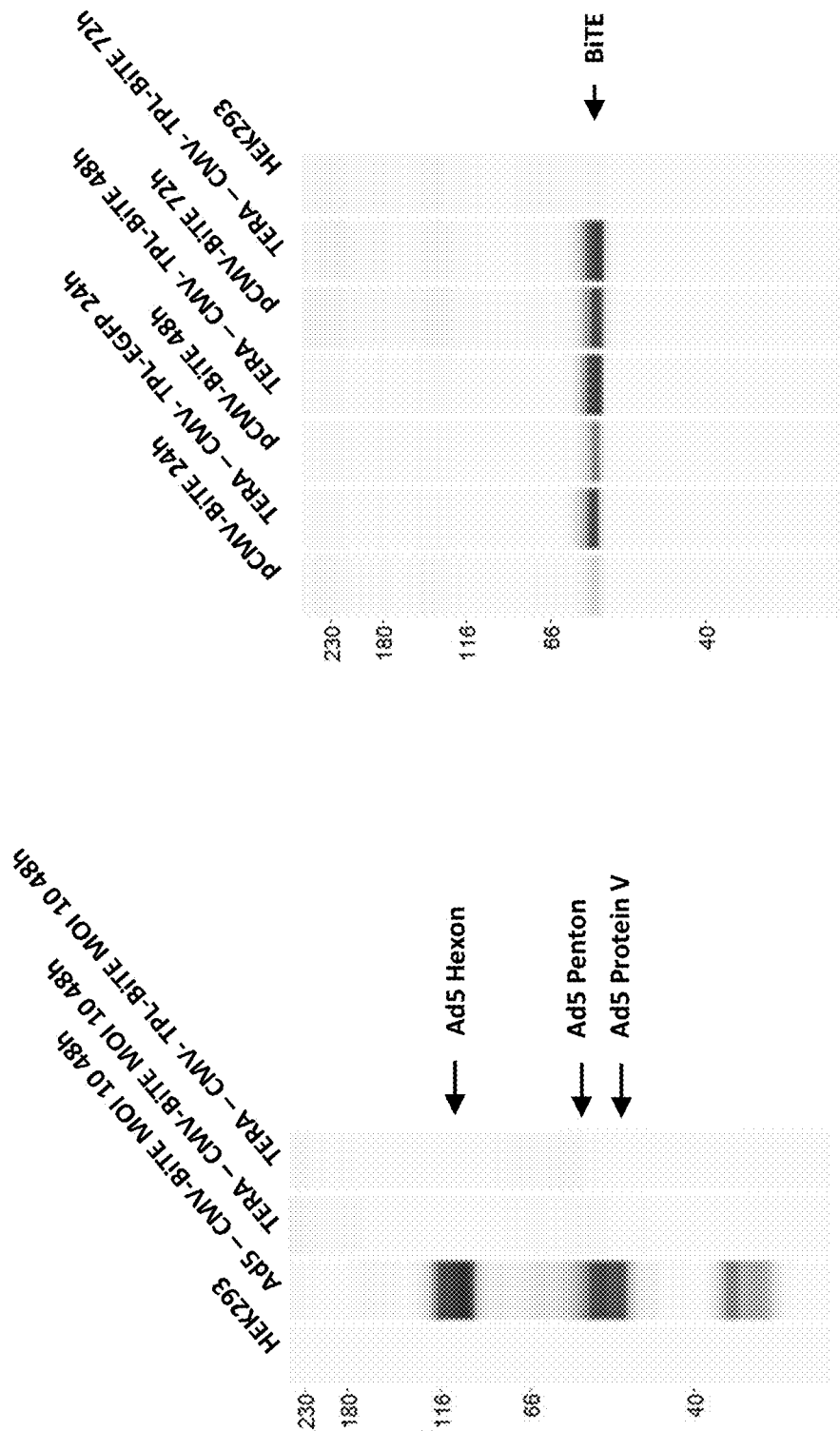

FIG. 15E shows Western blot detection of BiTE® protein expressed from TERA compared to E1/E3 deleted adenovirus. HEK293 cells, cultured in the absence of doxycycline, were infected with adenoviruses E1/E3-deleted or TERA-expressing BiTE® protein under control of the CMV promoter (with and without Ad5 TPL exons) at MOI 10 and BiTE® protein expression was measured at 48-hours post-infection from growth medium. TERA exhibited increase production of BiTE® protein compared to control adenovirus; however, ~2-fold increase in BiTE® protein production was observed from infection with TERA expressing BiTE® protein containing the Ad5 TPL exons. Additionally, while viral structural proteins were detected from infection with the E1/E3 deleted virus control, virus capsid proteins were undetectable following infection by TERA. Amplification of the viral genomic DNA was confirmed to be maintained and comparable to the control virus by qPCR analysis.

Example 13: TERA Enhances Production of rAAV Free of Ad5 Particle Contaminants

To evaluate the use of TERA for delivery of helper-functions and rAAV DNA for the production rAAV viral vectors, E1/E3 deleted control adenovirus and TERA was modified in the virus E1 deleted region to encode an rAAV genome, AAV2 ITRs flanking an EGFP expression cassette under control of the CMV promoter. The results are shown in FIGS. 16A-16G.

rAAV encoding EGFP transgene was produced by an established Helper-free triple transfection method, or via infection with control E1/E3 deleted adenovirus or TERA. HEK293 cells were triple-transfected with plasmid encoding 1) rAAV genome encoding EGFP, 2) AAV2 Rep and Cap, and 3) Ad5 Helper, or transduced with plasmid encoding AAV2 Rep and Cap, and control E1/E3 deleted adenovirus or TERA, in the presence of doxycycline or DMSO. Recombinant viruses were harvested from cellular lysates and growth media 72-hours post transduction and viral genomes, from encapsulated adenovirus and rAAV, were quantified by qPCR using primer and probe sets directed against adenovirus DNA encoding Fibre, or CMV promoter encoded by both rAAV and adenoviruses.

Figure 16B:
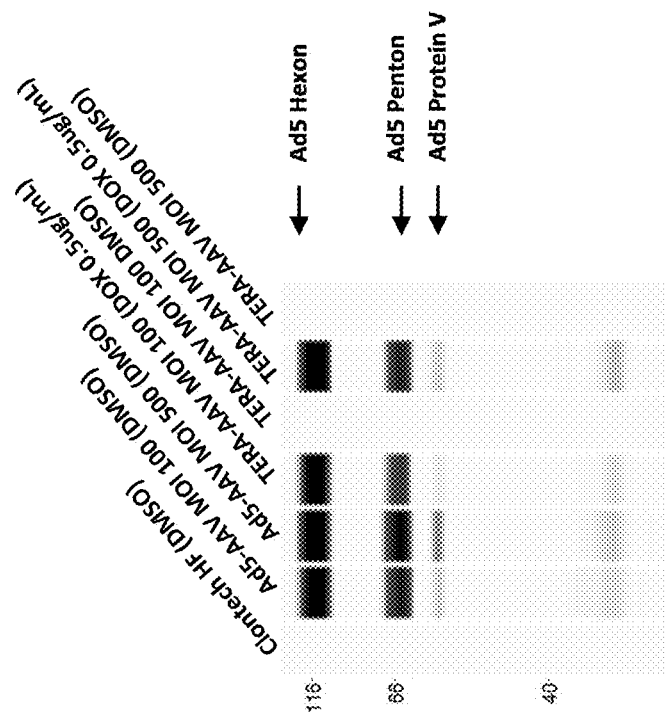
FIGS. 16A to 16H show rAAV vector production in HEK293 cells with TERA.
Figure 16A:
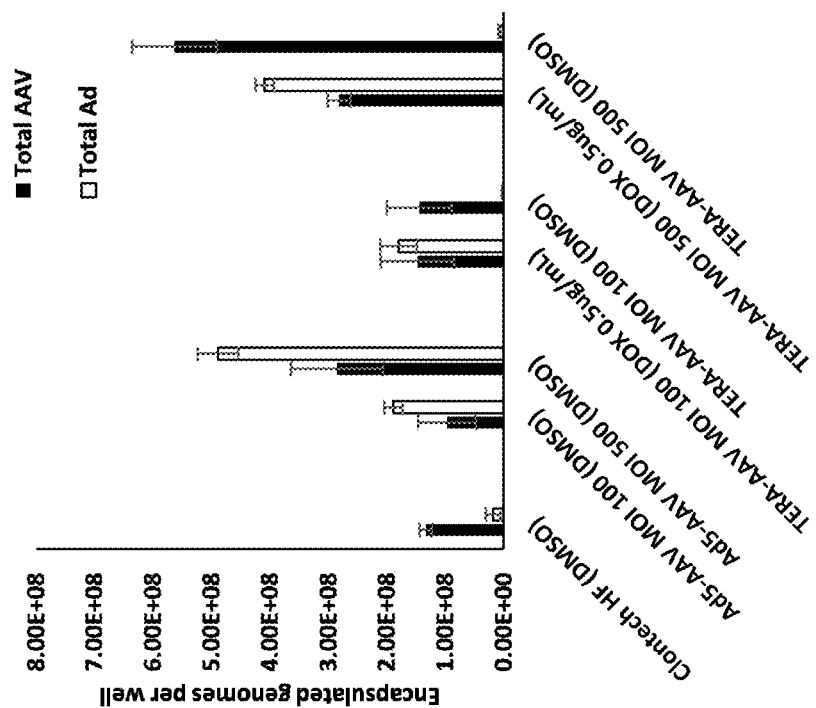
Figure 16C:
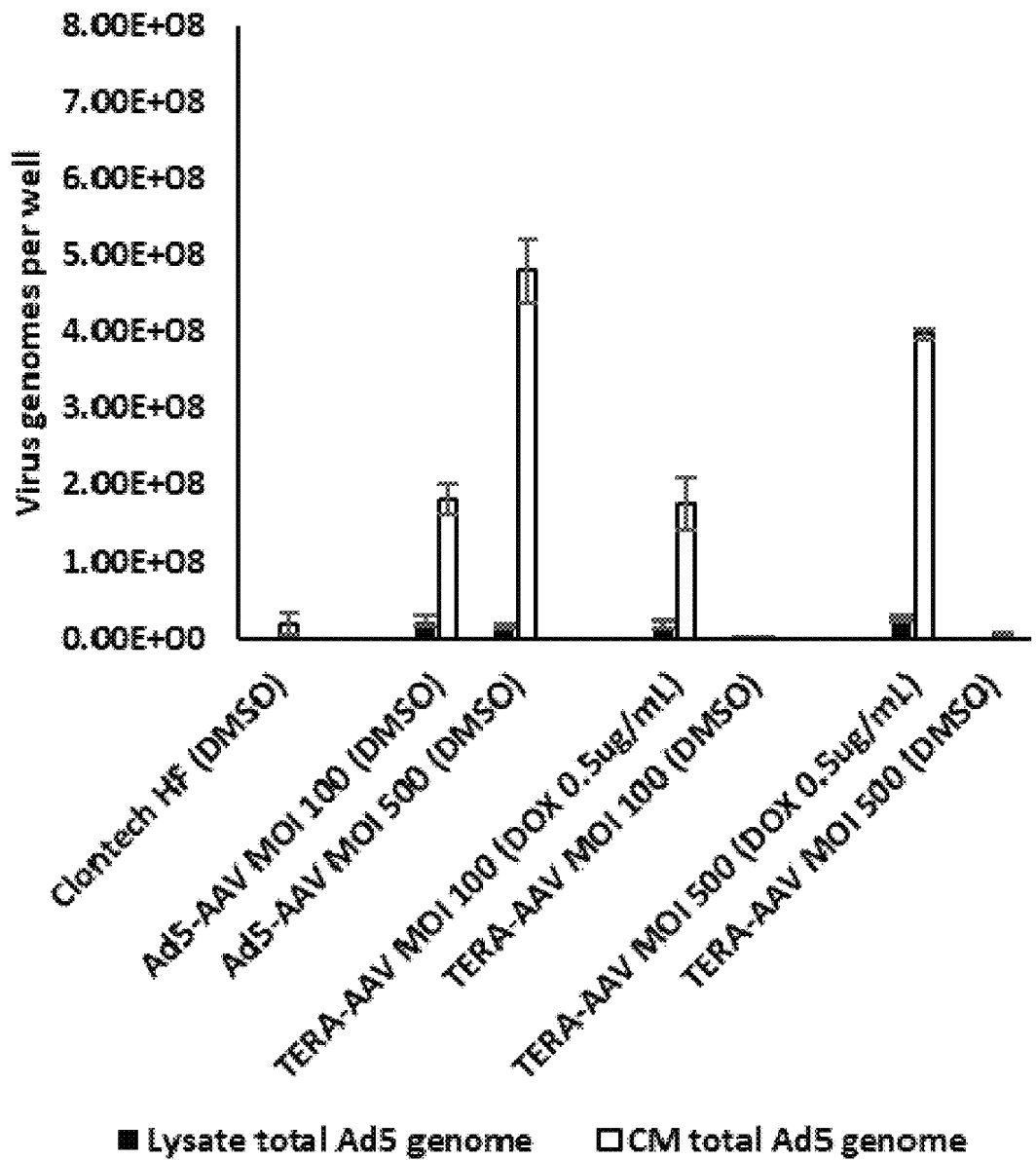
Figure 16D:
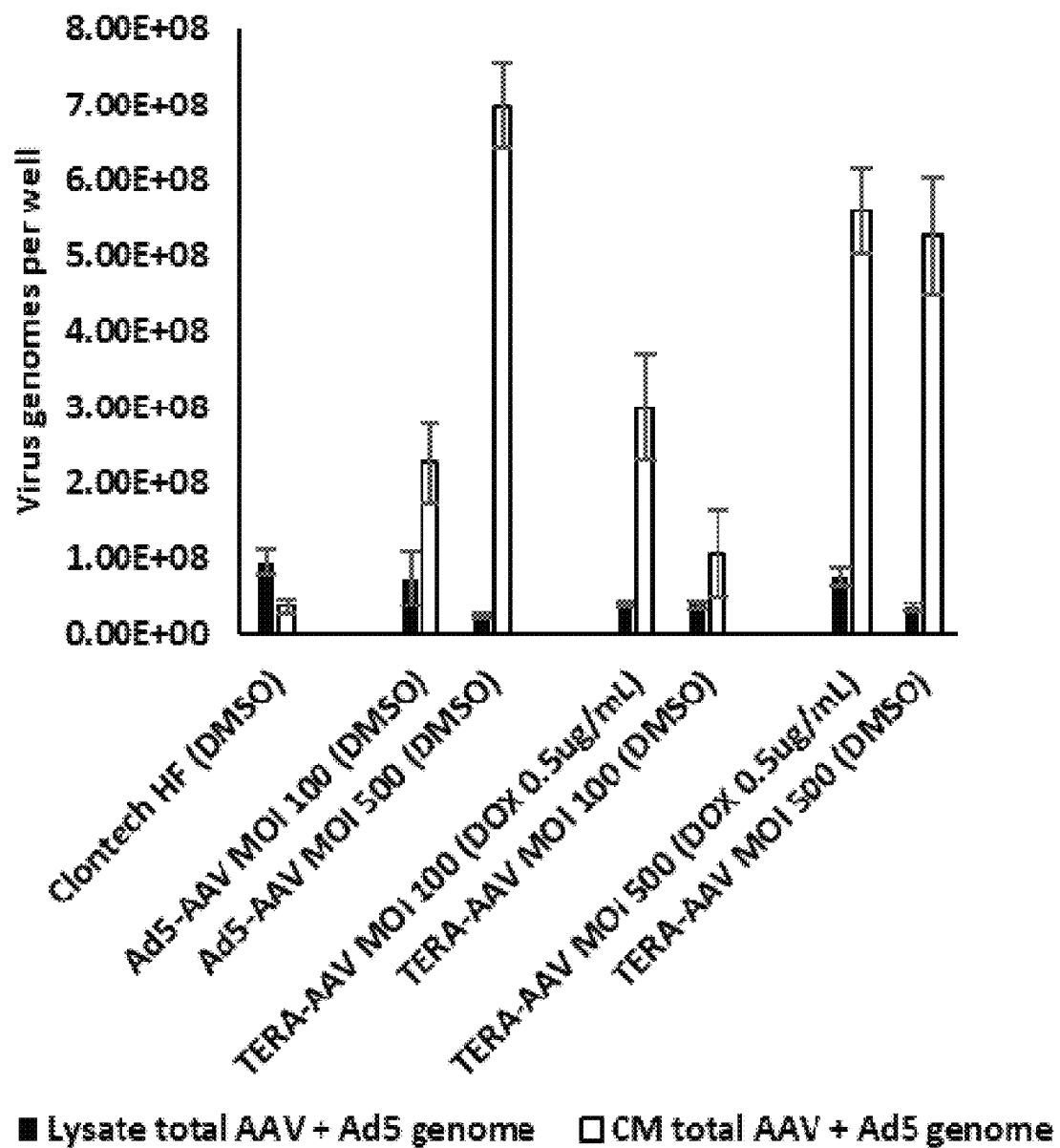

FIG. 16C, shows quantification of encapsulated adenovirus genomes from cellular lysate and growth medium. While significant levels of adenoviruses were detected following infection with the control adenovirus and TERA in HEK293 cells treated with DMSO and doxycycline, respectively, presence of adenoviruses were below the lowest standard and detection range of the assay from HEK293 cells, absent of doxycycline, when transduced with TERA or Helper-free production method. In contrast, significant levels of recombinant viruses from all samples were detected by qPCR assay using primer and probe sets directed against the encoded CMV promoter, present in both adenoviruses and rAAVs (FIG. 16D).

Since virus quantification used qPCR primers and probe directed against the encoded CMV promoter detected both rAAV and the adenoviral delivery vectors, total rAAV from each production method and conditions were determined by subtraction of overall adenovirus particles contamination detected (FIG. 16A). E1/E3 deleted adenovirus produced rAAV that were comparable or above the Helper-free production system by triple transfection, which was also accompanied with significant levels of adenovirus contamination. In contrast, HEK293 cells infected with TERA-AAV, in the absence of doxycycline, yielded ~5-fold increase in rAAV compared to Helper-free plasmid transfections with adenovirus contamination beyond the limit of the qPCR detection. (FIG. 16B) Adenovirus particles contamination in growth medium was further confirmed by Western blot using antibodies directed against Ad5 capsid protein. In line with results from qPCR analysis, adenovirus structural proteins were undetectable from Helper-free production method or infection with TERA (MOI 100 and 500) in HEK293 cells absent of doxycycline, while adenovirus proteins were readily detected from TERA infection in the presence of doxycycline, enabling active MLP, and from the E1/E3 control virus.

Figure 16E:
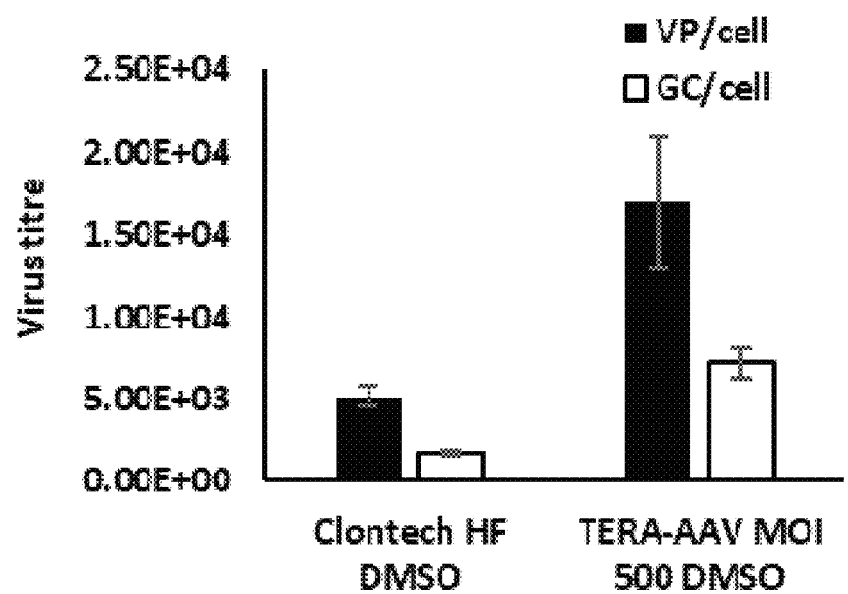
Figure 16F:
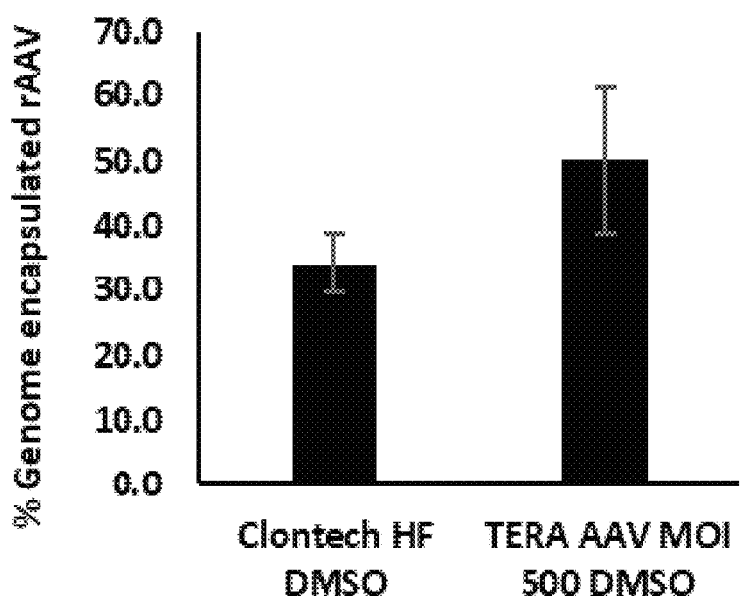

To determine rAAV particles with an encapsulated rAAV genome, rAAV capsids produced from methods of Helper-free plasmid transfection, or via TERA infection into plasmid Rep and Cap transfected HEK293 cells, were quantified. FIG. 16E shows total rAAV2 capsids and DNase-I resistant genome encapsulated particles determined by ELISA directed toward formed-AAV2 viral capsids and quantification of rAAV genome by qPCR, respectively. FIG. 16F shows per cell basis, TERA MOI 500 infection produced significantly higher amounts of rAAV2 capsids and DNase-I resistant genome encapsulated rAAVs, compared to Helper-free production method. Overall, Helper-free rAAV2 production and TERA produced genome encapsulated particles accounting to ~30% and ~50% of total rAAV2 capsid particles, respectively.

Figure 16G:
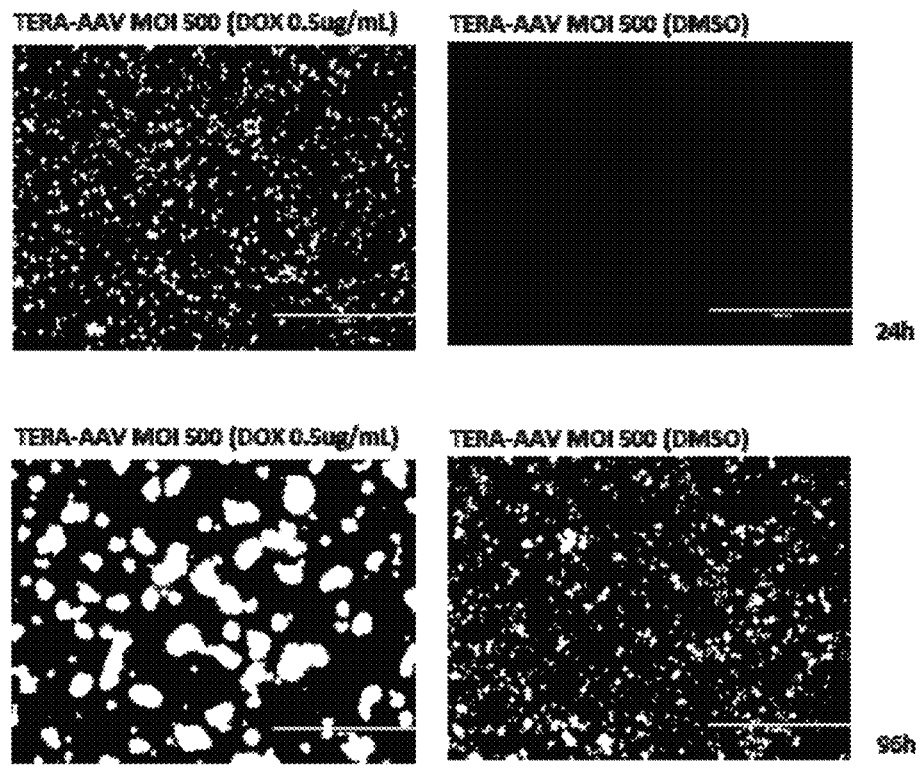
Figure 16H:
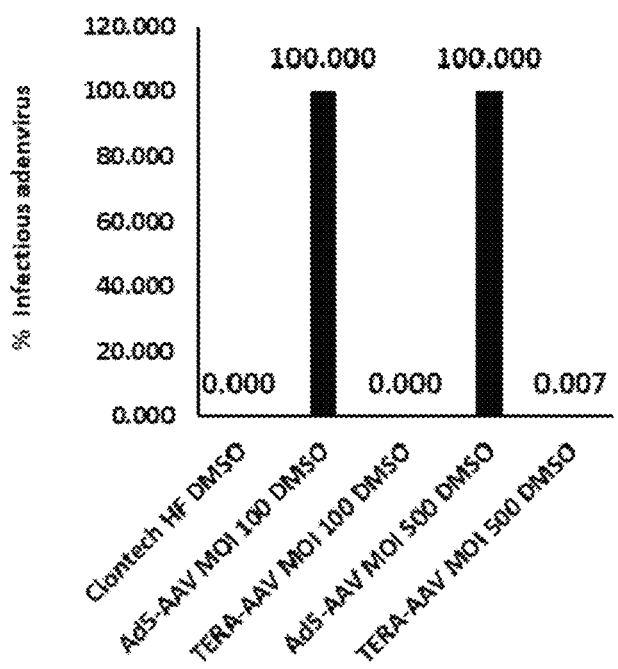

Contaminating adenovirus particles from the use of TERA in the production rAAV in HEK293 cells, cultured in the absence of doxycycline, were undetectable via Western blot and qPCR. FIG. 16H shows contaminating infectious adenovirus following production of rAAV by method of Helper-free, and infection by control E1/E3 adenovirus or TERA was determine by Tissue Culture Infectious Dose 50 assay (TCID50) in HEK293 cells. As shown in FIG. 16G transduction of HEK293 cells with crude rAAV produced by method of TERA infection in the presence of doxycycline results in early EGFP expression and adenovirus CPE cell morphology. In stark contrast, the absence of doxycycline enables MLP and adenovirus self-repression as seen from the delayed expression of EGFP reporter and an intact cell monolayer, presumably expressed from rAAV and the time required for second-strand DNA synthesis of rAAV genome. Additionally, while infectious adenoviruses were undetected by rAAV2 Helper-free production method lacking adenovirus, rAAV production by TERA infection at MOI 100 and 500, exhibit contaminating infectious adenovirus at levels of 0.0003% (>2e6 fold repression) and 0.007% compared to rAAV2 production using the control E1/E3 adenovirus, respectively. Overall, in the absence of doxycycline to enable MLP self-repression, TERA infection in HEK293 cells at MOI 100 and 500 reduced contaminating adenoviruses by ~3×10$^6$ and ~1.5×10$^4$ folds, respectively, compared to infection with E1/E3 deleted control adenovirus.

REFERENCES

Babiss L E, Ginsberg H S. Adenovirus type 5 early region 1b gene product is required for efficient shutoff of host protein synthesis. J Virol. 1984 April; 50(1):202-12.

Beaton, A., Palumbo, P., Berns, K. I. Expression from the adeno-associated virus p5 and p19 promoters is negatively regulated in trans by the rep protein. J Virol. 1989. 63(10):4450-4454.

Concino M, Goldman R A, Caruthers M H, Weinmann R. Point mutations of the adenovirus major late promoter with different transcriptional efficiencies in vitro. J Biol Chem. 1983 Jul. 10; 258(13):8493-6.

Concino M F, Lee R F, Merryweather J P, Weinmann R. The adenovirus major late promoter TATA box and initiation site are both necessary for transcription in vitro. Nucleic Acids Res. 1984 Oct. 11; 12(19):7423-33.

El-Mogy, M and Haj-Ahmad, Y. Transgene Expression under the Adenoviral Major Late Promoter, Tripartite Leader Sequence and E1 Genes in Absence and Presence of Adenovirus Infection. Journal of Molecular Biology Research; 2012, Vol. 2, No. 1

Garnier, A, Johanne, C. Nadeau, I. Kamen, A. and Massie. B. Scale-up of the adenovirus expression system for the production of recombinant protein in human 293S cells. Cytotechnology 15: 145-155, 1994. 145

Green, N. K., C. W. Herbert, et al. (2004). "Extended plasma circulation time and decreased toxicity of polymer-coated adenovirus." Gene Therapy 11(16): 1256-1263.

Honda, T., H. Saitoh, et al. (2000). "The coxsackievirus-adenovirus receptor protein as a cell adhesion molecule in the developing mouse brain." Molecular Brain Research 77(1): 19-28.

Karber, G. (1931). "50% end-point calculation." Arch Exp Pathol Pharmak 162: 480-483.

Kelkar, S. A., K. K. Pfister, et al. (2004). "Cytoplasmic dynein mediates adenovirus binding to microtubules." Journal of Virology 78(18): 10122-10132.

Li, J., Samulski, R. K., Xiao, X. Role for highly regulated rep gene expression in adeno-associated virus vector production. J. Virol. 1997. 71:5236-5243.

McConnell, M. J. and M. J. Imperiale (2004). "Biology of adenovirus and its use as a vector for gene therapy." Human Gene Therapy 15(11): 1022-1033.

Molin M, Shoshan M C, Ohman-Forslund K, Linder S, Akusjärvi G. Two novel adenovirus vector systems permitting regulated protein expression in gene transfer experiments. J Virol. 1998 October; 72(10):8358-61.

Ogasawara, Y., Mizukami, H., Masashi, U., Kume, A., Kanegae, Y., Saito, I., Monahan, J., Ozawa, K. Highly regulated expression of adeno-associated virus large Rep proteins in stable 293 cell lines using the cre/loxp switching system. J. Virol. 1999. 80: 2477-2480.

Rowe, W. P., R. J. Huebner, et al. (1953). "Isolation of a Cytopathogenic Agent from Human Adenoids Undergoing Spontaneous Degeneration in Tissue Culture." Proceedings of the Society for Experimental Biology and Medicine 84(3): 570-573.

Tollefson, A. E., J. S. Ryerse, et al. (1996). "The E3-11.6-kDa adenovirus death protein (ADP) is required for efficient cell death: Characterization of cells infected with adp mutants." Virology 220(1): 152-162.

Tomko, R. P., R. L. Xu, et al. (1997). "HCAR and MCAR: The human and mouse cellular receptors for subgroup C adenoviruses and group B coxsackieviruses." Proceedings of the National Academy of Sciences of the United States of America 94(7): 3352-3356.

Trotman, L. C., N. Mosberger, et al. (2001). "Import of adenovirus DNA involves the nuclear pore complex receptor CAN/Nup214 and histone H1." Nature Cell Biology 3(12): 1092-1100.

Wickham, T. J., P. Mathias, et al. (1993). "Integrin-Alpha-V-Beta-3 and Integrin-Alpha-V-Beta-5 Promote Adenovirus Internalization but Not Virus Attachment." Cell 73(2): 309-319.

Yang, Q., Chen, F., Trempe, J. P. Characterization of cell lines that inducibly express the adeno-associated virus rep proteins. J. Virol. 1994. 68(8): 4847-4856.

Zhang, H-G., Wang, Y. M., Xie, J. F., Liang, X., Hsu, H-C., Zhang, X., Douglas, J., Cruiel, D. T., Mountz, J. D. Recombinant adenovirus expressing adeno-associated virus cap and rep proteins supports production of high-titer recombinant adeno-associated virus. Gene. Ther. 2001. 8(9): 704-712.

The invention claimed is:

1. An adenoviral vector comprising a repressible Major Late Promoter (MLP) and a plurality of adenoviral late genes, wherein the MLP comprises one or more repressor elements which are capable of regulating or controlling transcription of the adenoviral late genes, and wherein the nucleotide sequence of the MLP consists of the nucleotide sequence set forth in SEQ ID NO: 6 or 7.

2. The adenoviral vector as claimed in claim 1, additionally comprising a plurality of adenoviral early genes and a transgene.

3. The adenoviral vector as claimed in claim 2, wherein the transgene comprises a Tripartite Leader (TPL) in its 5'-UTR.

4. The adenoviral vector as claimed in claim 2, wherein the transgene encodes a therapeutic polypeptide.

5. The adenoviral vector as claimed in claim 2, wherein the transgene encodes a virus protein, or a protein that is capable of assembly in or outside of a cell to produce a virus-like particle.

6. The adenoviral vector as claimed in claim 5, wherein the transgene encodes Norovirus VP1 or Hepatitis B HBSAG.

7. The adenoviral vector as claimed in claim 2, wherein the transgene encodes an AAV Rep polypeptide, an AAV Cap polypeptide, an AAV Rep-Cap polypeptide and/or the transgene encodes an AAV genome.

8. A process for producing a transgene product, the process comprising the steps:
  (a) infecting mammalian cells with an adenoviral vector as claimed in claim 2;
  (b) culturing the infected mammalian cells in a culture medium under conditions such that a product of the transgene is expressed; and
  (c) isolating or purifying the transgene product from the cells or from the cell culture medium.

9. The adenoviral vector as claimed in claim 1, wherein a gene encoding a repressor protein which is capable of binding to the one or more repressor elements is encoded within the adenoviral vector.

10. The adenoviral vector as claimed in claim 9, wherein the gene encoding the repressor protein is transcribed under the control of the MLP.

11. The adenoviral vector as claimed in claim 1, wherein the adenoviral vector further encodes an adenovirus L4 100K protein and wherein the L4 100K protein is not under control of the MLP.

12. The adenoviral vector as claimed in claim 1, wherein a transgene is inserted within an adenoviral early region, or within an adenoviral E1 region.

13. A composition comprising an adenovirus particle comprising an adenoviral vector as claimed in claim 1, together with one or more physiologically-acceptable carriers, excipients or diluents.

14. A kit comprising an adenoviral vector as claimed in claim 1, wherein the kit additionally comprises:
  (i) a cell line that allows the adenoviral vector to infect the cells and replicate the adenoviruses' genome, wherein the cell line represses the adenoviral vector's MLP; and/or
  (ii) one or more DNA plasmids for aiding in the construction of the adenoviral vector.

15. A mammalian cell comprising an adenoviral vector as claimed in claim 1.

16. A process for producing a modified mammalian cell, the process comprising the step:
  (a) infecting a mammalian cell with an adenoviral vector as claimed in claim 1, whereby the mammalian cell then comprises the adenoviral vector.

* * * * *